(12) United States Patent
Newton

(10) Patent No.: US 12,245,966 B2
(45) Date of Patent: Mar. 11, 2025

(54) FLUID COLLECTION DEVICES HAVING A SUMP BETWEEN A TUBE OPENING AND A BARRIER, AND RELATED SYSTEMS AND METHODS

(71) Applicant: PUREWICK CORPORATION, Covington, GA (US)

(72) Inventor: Camille Rose Newton, Bonsall, CA (US)

(73) Assignee: PUREWICK CORPORATION, Covington, GA (US)

( * ) Notice: Subject to any disclaimer, the term of this patent is extended or adjusted under 35 U.S.C. 154(b) by 0 days.

(21) Appl. No.: 18/426,795

(22) Filed: Jan. 30, 2024

(65) Prior Publication Data
US 2024/0164935 A1    May 23, 2024

Related U.S. Application Data

(63) Continuation of application No. 18/299,788, filed on Apr. 13, 2023, now Pat. No. 11,925,575, which is a
(Continued)

(51) Int. Cl.
*A61F 5/453*    (2006.01)
*A61F 5/44*    (2006.01)
(Continued)

(52) U.S. Cl.
CPC .......... *A61F 5/453* (2013.01); *A61F 5/4404* (2013.01); *A61F 5/4401* (2013.01); *A61F 5/443* (2013.01); *A61F 5/451* (2013.01)

(58) Field of Classification Search
CPC ...... A61F 5/451; A61F 5/4401; A61F 5/4408; A61F 5/443
See application file for complete search history.

(56) References Cited

U.S. PATENT DOCUMENTS

| 737,443 A | 8/1903 | Mooers |
| 1,015,905 A | 1/1912 | Northrop |

(Continued)

FOREIGN PATENT DOCUMENTS

| AU | 2018216821 A1 | 8/2019 |
| AU | 2021299304 A1 | 2/2023 |

(Continued)

OTHER PUBLICATIONS

US 9,908,683 B2, 03/2018, Sandhausen et al. (withdrawn)
(Continued)

*Primary Examiner* — Guy K Townsend
(74) *Attorney, Agent, or Firm* — Dorsey & Whitney LLP

(57) ABSTRACT

Examples relate to fluid collection devices, and related systems and methods. A fluid collection device includes a fluid impermeable barrier, a fluid permeable body, a tube, and a sump. The fluid impermeable barrier has a distal end region and defines an opening and a chamber in fluid communication with the opening. The fluid permeable body is positioned within the chamber at least partially at the distal end region. The tube extends into the chamber and has an end positioned proximate to the distal end region of the fluid impermeable barrier. The tube includes a tube opening at least proximate to the end of the tube and oriented to face at least a portion of the fluid permeable body. The sump is positioned in the area between the tube opening and the distal end region.

20 Claims, 9 Drawing Sheets

Related U.S. Application Data continuation of application No. PCT/US2021/043893, filed on Jul. 30, 2021.

(60) Provisional application No. 63/154,248, filed on Feb. 26, 2021.

(51) Int. Cl.
*A61F 5/443* (2006.01)
*A61F 5/451* (2006.01)

(56) References Cited

U.S. PATENT DOCUMENTS

| | | |
|---|---|---|
| 1,032,841 A | 7/1912 | Koenig |
| 1,178,644 A | 4/1916 | Johnson |
| 1,387,726 A | 8/1921 | Karge |
| 1,742,080 A | 12/1929 | Jones |
| 1,979,899 A | 11/1934 | Obrien et al. |
| 2,241,010 A | 5/1941 | Chipley |
| 2,262,772 A | 11/1941 | Peder |
| 2,326,881 A | 8/1943 | Packer |
| 2,379,346 A | 6/1945 | Farrell |
| 2,485,555 A | 10/1949 | Bester |
| 2,571,357 A | 10/1951 | Charles |
| 2,613,670 A | 10/1952 | Edward |
| 2,616,426 A | 11/1952 | Adele |
| 2,644,234 A | 7/1953 | Earl |
| 2,648,335 A | 8/1953 | Chambers |
| 2,859,786 A | 11/1958 | Tupper |
| 2,944,551 A | 7/1960 | Carl |
| 2,968,046 A * | 1/1961 | Duke ............. A61G 9/006 604/149 |
| 2,971,512 A | 2/1961 | Reinhardt |
| 3,032,038 A | 5/1962 | Swinn |
| 3,077,883 A | 2/1963 | Hill |
| 3,087,938 A | 4/1963 | Hans et al. |
| 3,169,528 A | 2/1965 | Knox et al. |
| 3,171,506 A | 3/1965 | Therkel |
| 3,194,238 A | 7/1965 | Breece |
| 3,198,994 A | 8/1965 | Hildebrandt et al. |
| 3,221,742 A | 12/1965 | Egon |
| 3,312,221 A | 4/1967 | Overment |
| 3,312,981 A | 4/1967 | Mcguire et al. |
| 3,349,768 A | 10/1967 | Keane |
| 3,362,590 A | 1/1968 | Gene |
| 3,366,116 A | 1/1968 | Huck |
| 3,398,848 A | 8/1968 | Donovan |
| 3,400,717 A | 9/1968 | Bruce et al. |
| 3,406,688 A | 10/1968 | Bruce |
| 3,424,163 A | 1/1969 | Gravdahl |
| 3,425,471 A | 2/1969 | Yates |
| 3,511,241 A | 5/1970 | Lee |
| 3,512,185 A | 5/1970 | Ellis |
| 3,520,300 A | 7/1970 | Flower |
| 3,528,423 A | 9/1970 | Lee |
| 3,613,123 A | 10/1971 | Langstrom |
| 3,648,700 A | 3/1972 | Warner |
| 3,651,810 A | 3/1972 | Ormerod |
| 3,661,155 A | 5/1972 | Lindan |
| 3,683,918 A | 8/1972 | Pizzella |
| 3,699,815 A | 10/1972 | Holbrook |
| 3,726,277 A | 4/1973 | Hirschman |
| 3,742,952 A | 7/1973 | Magers et al. |
| 3,757,355 A | 9/1973 | Allen et al. |
| 3,788,324 A | 1/1974 | Lim |
| 3,843,016 A | 10/1974 | Bornhorst et al. |
| 3,863,638 A | 2/1975 | Rogers et al. |
| 3,863,798 A | 2/1975 | Kurihara et al. |
| 3,864,759 A | 2/1975 | Horiuchi |
| 3,865,109 A | 2/1975 | Elmore et al. |
| 3,881,486 A | 5/1975 | Fenton |
| 3,881,489 A | 5/1975 | Hartwell |
| 3,915,189 A | 10/1975 | Holbrook et al. |
| 3,998,228 A | 12/1976 | Poidomani |
| 3,999,550 A | 12/1976 | Martin |
| 4,015,604 A | 4/1977 | Csillag |
| 4,020,843 A * | 5/1977 | Kanall ............. A61F 5/453 604/351 |
| 4,022,213 A | 5/1977 | Stein |
| 4,027,776 A | 6/1977 | Douglas |
| 4,064,962 A | 12/1977 | Hunt |
| 4,096,897 A | 6/1978 | Cammarata |
| 4,116,197 A | 9/1978 | Bermingham |
| 4,180,178 A | 12/1979 | Turner |
| 4,187,953 A | 2/1980 | Turner |
| 4,194,508 A | 3/1980 | Anderson |
| 4,200,102 A * | 4/1980 | Duhamel ............. A61F 5/451 604/353 |
| 4,202,058 A | 5/1980 | Anderson |
| 4,203,503 A | 5/1980 | Bertotti et al. |
| 4,209,076 A | 6/1980 | Bertotti et al. |
| 4,223,677 A | 9/1980 | Anderson |
| 4,233,025 A | 11/1980 | Larson et al. |
| 4,233,978 A | 11/1980 | Hickey |
| 4,246,901 A | 1/1981 | Frosch et al. |
| 4,253,542 A | 3/1981 | Ruspa et al. |
| 4,257,418 A | 3/1981 | Hessner |
| 4,270,539 A | 6/1981 | Frosch et al. |
| 4,281,655 A | 8/1981 | Terauchi |
| 4,292,916 A | 10/1981 | Bradley et al. |
| 4,330,239 A | 5/1982 | Gannaway |
| 4,352,356 A | 10/1982 | Tong |
| 4,360,933 A | 11/1982 | Kimura et al. |
| 4,365,363 A | 12/1982 | Windauer |
| 4,375,841 A | 3/1983 | Vielbig |
| 4,387,726 A * | 6/1983 | Denard ............. A61F 5/453 604/350 |
| 4,403,991 A | 9/1983 | Hill |
| 4,425,130 A | 1/1984 | Desmarais |
| 4,446,986 A | 5/1984 | Bowen et al. |
| 4,453,938 A | 6/1984 | Brendling |
| 4,457,314 A | 7/1984 | Knowles |
| 4,476,879 A | 10/1984 | Jackson |
| 4,526,688 A | 7/1985 | Schmidt et al. |
| 4,528,703 A | 7/1985 | Kraus |
| D280,438 S | 9/1985 | Wendt |
| 4,551,141 A | 11/1985 | Mcneil |
| 4,553,968 A | 11/1985 | Komis |
| 4,581,026 A | 4/1986 | Schneider |
| 4,589,516 A | 5/1986 | Inoue et al. |
| 4,601,716 A | 7/1986 | Smith |
| 4,610,675 A | 9/1986 | Triunfol |
| 4,620,333 A | 11/1986 | Ritter |
| 4,626,250 A | 12/1986 | Schneider |
| 4,627,846 A | 12/1986 | Ternstroem |
| 4,631,061 A | 12/1986 | Martin |
| 4,650,477 A | 3/1987 | Johnson |
| 4,655,754 A | 4/1987 | Richmond et al. |
| 4,656,675 A | 4/1987 | Fajnsztajn |
| 4,681,570 A | 7/1987 | Dalton |
| 4,681,577 A | 7/1987 | Stern et al. |
| 4,692,160 A | 9/1987 | Nussbaumer |
| 4,707,864 A | 11/1987 | Ikematsu et al. |
| 4,713,065 A | 12/1987 | Koot |
| 4,713,066 A | 12/1987 | Komis |
| 4,723,953 A | 2/1988 | Pratt et al. |
| 4,735,841 A | 4/1988 | Sourdet |
| 4,743,236 A | 5/1988 | Manschot |
| 4,747,166 A * | 5/1988 | Kuntz ............. A61F 5/455 4/144.1 |
| 4,752,944 A | 6/1988 | Conrads et al. |
| 4,769,215 A | 9/1988 | Ehrenkranz |
| 4,771,484 A | 9/1988 | Mozell |
| 4,772,280 A | 9/1988 | Rooyakkers |
| 4,784,654 A | 11/1988 | Beecher |
| 4,790,830 A | 12/1988 | Hamacher |
| 4,790,835 A | 12/1988 | Elias |
| 4,791,686 A | 12/1988 | Taniguchi et al. |
| 4,795,449 A * | 1/1989 | Schneider ............. A61F 5/441 604/326 |
| 4,798,603 A | 1/1989 | Meyer et al. |
| 4,799,928 A | 1/1989 | Crowley |
| 4,804,377 A | 2/1989 | Hanifl et al. |
| 4,812,053 A | 3/1989 | Bhattacharjee |

(56) References Cited

U.S. PATENT DOCUMENTS

| | | | |
|---|---|---|---|
| 4,813,943 A | 3/1989 | Smith | |
| 4,820,297 A | 4/1989 | Kaufman et al. | |
| 4,846,818 A | 7/1989 | Keldahl et al. | |
| 4,846,909 A | 7/1989 | Klug et al. | |
| 4,865,595 A | 9/1989 | Heyden | |
| 4,880,417 A | 11/1989 | Yabrov et al. | |
| 4,882,794 A | 11/1989 | Stewart | |
| 4,883,465 A | 11/1989 | Brennan | |
| 4,886,498 A | 12/1989 | Newton | |
| 4,886,508 A * | 12/1989 | Washington | A61F 5/455 604/347 |
| 4,886,509 A | 12/1989 | Mattsson | |
| 4,889,532 A | 12/1989 | Metz et al. | |
| 4,889,533 A | 12/1989 | Beecher | |
| 4,890,691 A | 1/1990 | Ching-ho | |
| 4,903,254 A | 2/1990 | Haas | |
| 4,904,248 A | 2/1990 | Vaillancourt | |
| 4,905,692 A | 3/1990 | More | |
| 4,936,838 A | 6/1990 | Cross et al. | |
| 4,950,262 A | 8/1990 | Takagi | |
| 4,955,922 A | 9/1990 | Terauchi | |
| 4,957,487 A | 9/1990 | Gerow | |
| 4,965,460 A | 10/1990 | Tanaka et al. | |
| 4,986,823 A * | 1/1991 | Anderson | A61F 5/455 604/329 |
| 4,987,849 A | 1/1991 | Sherman | |
| 5,002,541 A | 3/1991 | Conkling et al. | |
| 5,004,463 A | 4/1991 | Nigay | |
| 5,031,248 A | 7/1991 | Kemper | |
| 5,045,077 A | 9/1991 | Blake | |
| 5,045,283 A | 9/1991 | Patel | |
| 5,049,144 A | 9/1991 | Payton | |
| 5,053,339 A | 10/1991 | Patel | |
| 5,057,092 A | 10/1991 | Webster | |
| 5,058,088 A | 10/1991 | Haas et al. | |
| 5,071,347 A | 12/1991 | Mcguire | |
| 5,078,707 A | 1/1992 | Peter | |
| 5,084,037 A | 1/1992 | Barnett | |
| 5,100,396 A | 3/1992 | Zamierowski | |
| 5,112,324 A | 5/1992 | Wallace | |
| 5,147,301 A | 9/1992 | Ruvio | |
| 5,176,667 A | 1/1993 | Debring | |
| 5,195,997 A | 3/1993 | Carns | |
| 5,196,654 A | 3/1993 | Diflora et al. | |
| 5,203,699 A | 4/1993 | Mcguire | |
| 5,244,458 A | 9/1993 | Takasu | |
| 5,246,454 A | 9/1993 | Peterson | |
| 5,267,988 A | 12/1993 | Farkas | |
| 5,275,307 A | 1/1994 | Freese | |
| 5,282,795 A | 2/1994 | Finney | |
| 5,295,983 A | 3/1994 | Kubo | |
| 5,300,052 A * | 4/1994 | Kubo | A61F 5/453 604/350 |
| 5,304,749 A | 4/1994 | Crandell | |
| 5,312,383 A | 5/1994 | Kubalak | |
| 5,318,550 A | 6/1994 | Cermak et al. | |
| 5,330,459 A | 7/1994 | Lavon et al. | |
| 5,340,840 A | 8/1994 | Park et al. | |
| 5,382,244 A | 1/1995 | Telang | |
| 5,409,014 A | 4/1995 | Napoli et al. | |
| 5,411,495 A | 5/1995 | Willingham | |
| 5,423,784 A | 6/1995 | Metz | |
| 5,456,246 A | 10/1995 | Schmieding et al. | |
| 5,466,229 A | 11/1995 | Elson et al. | |
| 5,478,334 A | 12/1995 | Bernstein | |
| 5,499,977 A | 3/1996 | Marx | |
| 5,543,042 A | 8/1996 | Filan et al. | |
| D373,928 S | 9/1996 | Green | |
| 5,582,604 A | 12/1996 | Ahr et al. | |
| 5,592,950 A | 1/1997 | Kopelowicz | |
| 5,605,161 A | 2/1997 | Cross | |
| 5,618,277 A | 4/1997 | Goulter | |
| 5,628,735 A | 5/1997 | Skow | |
| 5,636,643 A | 6/1997 | Argenta et al. | |
| 5,637,104 A | 6/1997 | Ball et al. | |
| 5,674,212 A | 10/1997 | Osborn et al. | |
| 5,678,564 A | 10/1997 | Lawrence et al. | |
| 5,687,429 A | 11/1997 | Rahlff | |
| 5,695,485 A | 12/1997 | Duperret et al. | |
| 5,700,254 A | 12/1997 | Mcdowall et al. | |
| 5,701,612 A | 12/1997 | Daneshvar | |
| 5,705,777 A | 1/1998 | Flanigan et al. | |
| 5,752,944 A | 5/1998 | Dann et al. | |
| 5,763,333 A * | 6/1998 | Suzuki | B32B 7/12 428/340 |
| 5,772,644 A | 6/1998 | Bark et al. | |
| 5,792,132 A | 8/1998 | Garcia | |
| 5,827,243 A | 10/1998 | Palestrant | |
| 5,827,247 A | 10/1998 | Kay | |
| 5,827,250 A | 10/1998 | Fujioka et al. | |
| 5,827,257 A | 10/1998 | Fujioka et al. | |
| D401,699 S | 11/1998 | Herchenbach et al. | |
| 5,859,393 A | 1/1999 | Cummins et al. | |
| 5,865,378 A | 2/1999 | Hollinshead et al. | |
| 5,876,393 A | 3/1999 | Ahr et al. | |
| 5,887,291 A | 3/1999 | Bellizzi | |
| 5,891,125 A | 4/1999 | Plumley | |
| 5,894,608 A * | 4/1999 | Birbara | A61F 5/4556 604/319 |
| D409,303 S | 5/1999 | Oepping | |
| 5,911,222 A * | 6/1999 | Lawrence | A61F 5/455 600/573 |
| 5,957,904 A | 9/1999 | Holland | |
| 5,968,026 A | 10/1999 | Osborn et al. | |
| 5,972,505 A | 10/1999 | Phillips et al. | |
| 6,007,526 A | 12/1999 | Passalaqua et al. | |
| 6,039,060 A | 3/2000 | Rower | |
| 6,050,983 A | 4/2000 | Moore et al. | |
| 6,059,762 A | 5/2000 | Boyer et al. | |
| 6,063,064 A | 5/2000 | Tuckey et al. | |
| 6,098,625 A | 8/2000 | Winkler | |
| 6,105,174 A | 8/2000 | Karlsten et al. | |
| 6,113,582 A | 9/2000 | Dwork | |
| 6,117,163 A | 9/2000 | Bierman | |
| 6,123,398 A * | 9/2000 | Arai | B60T 8/17552 303/151 |
| 6,129,718 A | 10/2000 | Wada et al. | |
| 6,131,964 A | 10/2000 | Sareshwala | |
| 6,152,902 A | 11/2000 | Christian et al. | |
| 6,164,569 A | 12/2000 | Hollinshead et al. | |
| 6,177,606 B1 | 1/2001 | Etheredge et al. | |
| 6,209,142 B1 | 4/2001 | Mattsson et al. | |
| 6,220,050 B1 | 4/2001 | Cooksey | |
| 6,244,311 B1 | 6/2001 | Hand et al. | |
| 6,248,096 B1 | 6/2001 | Dwork et al. | |
| 6,263,887 B1 | 7/2001 | Dunn | |
| 6,283,246 B1 | 9/2001 | Nishikawa | |
| 6,311,339 B1 * | 11/2001 | Kraus | A61F 5/451 4/144.1 |
| 6,336,919 B1 | 1/2002 | Davis et al. | |
| 6,338,729 B1 | 1/2002 | Wada et al. | |
| 6,352,525 B1 | 3/2002 | Wakabayashi | |
| 6,394,988 B1 | 5/2002 | Hashimoto | |
| 6,398,742 B1 | 6/2002 | Kim | |
| 6,406,463 B1 | 6/2002 | Brown | |
| 6,409,712 B1 | 6/2002 | Dutari et al. | |
| 6,416,500 B1 | 7/2002 | Wada et al. | |
| 6,423,045 B1 | 7/2002 | Wise et al. | |
| 6,428,521 B1 | 8/2002 | Droll | |
| 6,428,522 B1 | 8/2002 | Dipalma et al. | |
| 6,446,454 B1 | 9/2002 | Lee et al. | |
| 6,475,198 B1 | 11/2002 | Lipman et al. | |
| 6,479,726 B1 | 11/2002 | Cole et al. | |
| 6,491,673 B1 | 12/2002 | Palumbo et al. | |
| 6,508,794 B1 | 1/2003 | Palumbo et al. | |
| 6,524,292 B1 | 2/2003 | Dipalma et al. | |
| 6,540,729 B1 | 4/2003 | Wada et al. | |
| 6,547,771 B2 | 4/2003 | Robertson et al. | |
| 6,569,133 B2 | 5/2003 | Cheng et al. | |
| D476,518 S | 7/2003 | Doppelt | |
| 6,592,560 B2 | 7/2003 | Snyder et al. | |
| 6,610,038 B1 | 8/2003 | Dipalma et al. | |
| 6,618,868 B2 | 9/2003 | Minnick | |
| 6,620,142 B1 | 9/2003 | Flueckiger | |

(56) References Cited

U.S. PATENT DOCUMENTS

| | | | |
|---|---|---|---|
| 6,629,651 B1 | 10/2003 | Male et al. | |
| 6,635,038 B2 | 10/2003 | Scovel | |
| 6,652,495 B1 | 11/2003 | Walker | |
| 6,666,850 B1 | 12/2003 | Ahr et al. | |
| 6,685,684 B1 | 2/2004 | Falconer | |
| 6,695,828 B1 | 2/2004 | Dipalma et al. | |
| 6,699,174 B1 | 3/2004 | Bennett | |
| 6,700,034 B1 | 3/2004 | Lindsay et al. | |
| 6,702,793 B1 | 3/2004 | Sweetser et al. | |
| 6,706,027 B2* | 3/2004 | Harvie | A61F 5/453 604/326 |
| 6,732,384 B2* | 5/2004 | Scott | A47K 11/12 4/144.1 |
| 6,736,977 B1 | 5/2004 | Hall et al. | |
| 6,740,066 B2* | 5/2004 | Wolff | A61F 5/451 604/323 |
| 6,764,477 B1 | 7/2004 | Chen et al. | |
| 6,783,519 B2 | 8/2004 | Samuelsson | |
| 6,796,974 B2 | 9/2004 | Palumbo et al. | |
| 6,814,547 B2 | 11/2004 | Childers et al. | |
| 6,849,065 B2 | 2/2005 | Schmidt et al. | |
| 6,857,137 B2 | 2/2005 | Otto | |
| 6,885,690 B2 | 4/2005 | Aggerstam et al. | |
| 6,888,044 B2 | 5/2005 | Fell et al. | |
| 6,893,425 B2 | 5/2005 | Dunn et al. | |
| 6,912,737 B2 | 7/2005 | Ernest et al. | |
| 6,918,899 B2* | 7/2005 | Harvie | A61F 5/451 604/326 |
| 6,979,324 B2 | 12/2005 | Bybordi et al. | |
| 7,018,366 B2* | 3/2006 | Easter | A61F 5/451 604/327 |
| 7,066,411 B2 | 6/2006 | Male et al. | |
| 7,122,023 B1 | 10/2006 | Hinoki | |
| 7,125,399 B2 | 10/2006 | Miskie | |
| 7,131,964 B2* | 11/2006 | Harvie | A61F 5/455 604/326 |
| 7,135,012 B2* | 11/2006 | Harvie | A61F 5/453 604/326 |
| 7,141,043 B2* | 11/2006 | Harvie | A61F 5/451 604/326 |
| D533,972 S | 12/2006 | La | |
| 7,160,273 B2 | 1/2007 | Greter et al. | |
| 7,171,699 B2 | 2/2007 | Ernest et al. | |
| 7,171,871 B2 | 2/2007 | Kozak | |
| 7,179,951 B2 | 2/2007 | Krishnaswamy-mirle et al. | |
| 7,181,781 B1* | 2/2007 | Trabold | A61F 5/455 4/144.1 |
| 7,186,245 B1 | 3/2007 | Cheng et al. | |
| 7,192,424 B2 | 3/2007 | Cooper | |
| 7,219,764 B1 | 5/2007 | Forbes | |
| 7,220,250 B2* | 5/2007 | Suzuki | A61F 5/451 604/328 |
| D562,975 S | 2/2008 | Otto | |
| 7,335,189 B2* | 2/2008 | Harvie | A61F 5/451 604/326 |
| 7,358,282 B2 | 4/2008 | Krueger et al. | |
| 7,390,320 B2* | 6/2008 | Machida | A61F 5/455 4/144.1 |
| 7,438,706 B2 | 10/2008 | Koizumi et al. | |
| 7,488,310 B2 | 2/2009 | Yang | |
| 7,491,194 B1 | 2/2009 | Oliwa | |
| D591,106 S | 4/2009 | Dominique et al. | |
| 7,513,381 B2 | 4/2009 | Heng et al. | |
| 7,520,872 B2 | 4/2009 | Biggie et al. | |
| D593,801 S | 6/2009 | Wilson et al. | |
| 7,540,364 B2 | 6/2009 | Sanderson | |
| 7,549,511 B2 | 6/2009 | Marocco | |
| 7,549,512 B2 | 6/2009 | Newberry | |
| 7,585,293 B2 | 9/2009 | Vermaak | |
| 7,588,560 B1 | 9/2009 | Dunlop | |
| 7,637,905 B2 | 12/2009 | Saadat et al. | |
| 7,665,359 B2 | 2/2010 | Barber | |
| 7,682,347 B2 | 3/2010 | Parks et al. | |
| 7,687,004 B2 | 3/2010 | Allen | |
| 7,695,459 B2 | 4/2010 | Gilbert et al. | |
| 7,695,460 B2 | 4/2010 | Wada et al. | |
| 7,699,818 B2 | 4/2010 | Gilbert | |
| 7,699,831 B2* | 4/2010 | Bengtson | A61M 27/00 604/313 |
| 7,722,584 B2 | 5/2010 | Tanaka et al. | |
| 7,727,206 B2 | 6/2010 | Gorres | |
| 7,740,620 B2 | 6/2010 | Gilbert et al. | |
| 7,749,205 B2* | 7/2010 | Tazoe | A61F 5/451 604/320 |
| 7,755,497 B2* | 7/2010 | Wada | A61F 5/451 340/604 |
| 7,766,887 B2 | 8/2010 | Burns et al. | |
| D625,407 S | 10/2010 | Koizumi et al. | |
| 7,806,879 B2 | 10/2010 | Brooks et al. | |
| 7,811,272 B2 | 10/2010 | Lindsay et al. | |
| 7,815,067 B2 | 10/2010 | Matsumoto et al. | |
| 7,833,169 B2 | 11/2010 | Hannon | |
| 7,857,806 B2 | 12/2010 | Karpowicz et al. | |
| 7,866,942 B2 | 1/2011 | Harvie | |
| 7,871,385 B2 | 1/2011 | Levinson et al. | |
| 7,875,010 B2 | 1/2011 | Frazier et al. | |
| 7,901,389 B2 | 3/2011 | Mombrinie | |
| 7,927,320 B2 | 4/2011 | Goldwasser et al. | |
| 7,927,321 B2 | 4/2011 | Marland | |
| 7,931,634 B2 | 4/2011 | Swiecicki et al. | |
| 7,939,706 B2 | 5/2011 | Okabe et al. | |
| 7,946,443 B2 | 5/2011 | Stull et al. | |
| 7,947,025 B2 | 5/2011 | Buglino et al. | |
| 7,963,419 B2 | 6/2011 | Burney et al. | |
| 7,976,519 B2 | 7/2011 | Bubb et al. | |
| 7,993,318 B2 | 8/2011 | Olsson et al. | |
| 8,015,627 B2 | 9/2011 | Baker et al. | |
| 8,016,071 B1 | 9/2011 | Martinus et al. | |
| 8,028,460 B2 | 10/2011 | Williams | |
| 8,047,398 B2 | 11/2011 | Dimartino et al. | |
| 8,083,094 B2 | 12/2011 | Caulfield et al. | |
| 8,128,608 B2* | 3/2012 | Thevenin | A61F 13/84 604/347 |
| 8,181,651 B2 | 5/2012 | Pinel | |
| 8,181,819 B2 | 5/2012 | Burney et al. | |
| 8,211,063 B2* | 7/2012 | Bierman | A61M 25/02 604/179 |
| 8,221,369 B2 | 7/2012 | Parks et al. | |
| 8,241,262 B2 | 8/2012 | Mahnensmith | |
| 8,277,426 B2 | 10/2012 | Wilcox et al. | |
| 8,287,508 B1* | 10/2012 | Sanchez | A61F 5/4404 604/326 |
| 8,303,554 B2 | 11/2012 | Tsai et al. | |
| 8,322,565 B2 | 12/2012 | Caulfield et al. | |
| 8,337,477 B2 | 12/2012 | Parks et al. | |
| D674,241 S | 1/2013 | Bickert et al. | |
| 8,343,122 B2 | 1/2013 | Gorres | |
| 8,343,125 B2 | 1/2013 | Kawazoe et al. | |
| 8,353,074 B2 | 1/2013 | Krebs | |
| 8,353,886 B2 | 1/2013 | Bester et al. | |
| D676,241 S | 2/2013 | Merrill | |
| 8,388,588 B2 | 3/2013 | Wada et al. | |
| D679,807 S | 4/2013 | Burgess et al. | |
| 8,425,482 B2 | 4/2013 | Khoubnazar | |
| 8,434,586 B2 | 5/2013 | Pawelski et al. | |
| 8,449,510 B2 | 5/2013 | Martini et al. | |
| D684,260 S | 6/2013 | Lund et al. | |
| 8,470,230 B2 | 6/2013 | Caulfield et al. | |
| 8,479,941 B2 | 7/2013 | Matsumoto et al. | |
| 8,479,949 B2 | 7/2013 | Henkel | |
| 8,500,719 B1 | 8/2013 | Simpson et al. | |
| 8,512,301 B2 | 8/2013 | Ma | |
| 8,529,530 B2 | 9/2013 | Koch et al. | |
| 8,535,284 B2 | 9/2013 | Joder et al. | |
| 8,546,639 B2* | 10/2013 | Wada | A61F 5/4401 604/361 |
| 8,551,075 B2* | 10/2013 | Bengtson | A61M 1/84 604/543 |
| 8,568,376 B2* | 10/2013 | Delattre | A61F 13/471 604/385.01 |
| D694,404 S | 11/2013 | Burgess et al. | |

(56) References Cited

U.S. PATENT DOCUMENTS

| | | |
|---|---|---|
| 8,585,683 B2 * | 11/2013 | Bengtson ............ A61M 1/985 |
| | | 604/543 |
| 8,652,112 B2 | 2/2014 | Johannison et al. |
| 8,669,412 B2 | 3/2014 | Fernkvist et al. |
| D702,973 S | 4/2014 | Norland et al. |
| 8,703,032 B2 | 4/2014 | Menon et al. |
| D704,330 S | 5/2014 | Cicatelli |
| D704,510 S | 5/2014 | Mason et al. |
| D705,423 S | 5/2014 | Walsh Cutler |
| D705,926 S | 5/2014 | Burgess et al. |
| 8,714,394 B2 | 5/2014 | Wulf |
| 8,715,267 B2 | 5/2014 | Bengtson et al. |
| 8,757,425 B2 | 6/2014 | Copeland |
| 8,777,032 B2 | 7/2014 | Biesecker et al. |
| 8,808,260 B2 | 8/2014 | Koch et al. |
| 8,864,730 B2 * | 10/2014 | Conway ............... A61F 5/4401 |
| | | 604/346 |
| 8,881,923 B2 | 11/2014 | Higginson |
| 8,882,731 B2 * | 11/2014 | Suzuki ................. A61F 5/451 |
| | | 604/327 |
| 8,936,585 B2 | 1/2015 | Carson et al. |
| D729,581 S | 5/2015 | Boroski |
| 9,028,460 B2 * | 5/2015 | Medeiros ............. A61F 5/451 |
| | | 604/347 |
| 9,056,698 B2 | 6/2015 | Noer |
| 9,078,792 B2 | 7/2015 | Ruiz |
| 9,145,879 B2 | 9/2015 | Pirovano et al. |
| 9,173,602 B2 | 11/2015 | Gilbert |
| 9,173,799 B2 * | 11/2015 | Tanimoto ............. A61F 5/453 |
| 9,187,220 B2 | 11/2015 | Biesecker et al. |
| 9,199,772 B2 | 12/2015 | Krippendorf |
| 9,233,020 B2 | 1/2016 | Matsumiya |
| 9,248,058 B2 | 2/2016 | Conway et al. |
| 9,308,118 B1 | 4/2016 | Dupree et al. |
| 9,309,029 B2 | 4/2016 | Incorvia et al. |
| 9,333,281 B2 | 5/2016 | Giezendanner et al. |
| 9,381,108 B2 | 7/2016 | Longoni et al. |
| 9,382,047 B2 | 7/2016 | Schmidtner et al. |
| 9,402,424 B2 | 8/2016 | Roy |
| 9,456,937 B2 | 10/2016 | Ellis |
| 9,480,595 B2 | 11/2016 | Baham et al. |
| 9,517,865 B2 | 12/2016 | Albers et al. |
| D777,941 S | 1/2017 | Piramoon |
| 9,533,806 B2 | 1/2017 | Ding et al. |
| 9,550,611 B2 | 1/2017 | Hodge |
| 9,555,930 B2 | 1/2017 | Campbell et al. |
| 9,623,159 B2 | 4/2017 | Locke |
| D789,522 S | 6/2017 | Burgess et al. |
| 9,687,849 B2 | 6/2017 | Bruno et al. |
| 9,694,949 B2 | 7/2017 | Hendricks et al. |
| 9,709,048 B2 | 7/2017 | Kinjo |
| 9,713,547 B2 | 7/2017 | Lee et al. |
| 9,732,754 B2 | 8/2017 | Huang et al. |
| 9,752,564 B2 | 9/2017 | Arceno et al. |
| 9,788,992 B2 | 10/2017 | Harvie |
| D804,907 S | 12/2017 | Sandoval |
| 9,868,564 B2 | 1/2018 | Mcgirr et al. |
| D814,239 S | 4/2018 | Arora |
| D817,484 S | 5/2018 | Lafond |
| 10,037,640 B2 | 7/2018 | Gordon |
| 10,058,470 B2 | 8/2018 | Phillips |
| 10,098,990 B2 | 10/2018 | Koch et al. |
| D835,264 S | 12/2018 | Mozzicato et al. |
| D835,779 S | 12/2018 | Mozzicato et al. |
| D840,533 S | 2/2019 | Mozzicato et al. |
| D840,534 S | 2/2019 | Mozzicato et al. |
| 10,225,376 B2 | 3/2019 | Perez Martinez |
| 10,226,376 B2 * | 3/2019 | Sanchez ................ A61F 5/443 |
| 10,258,517 B1 | 4/2019 | Maschino et al. |
| D848,612 S | 5/2019 | Mozzicato et al. |
| 10,307,305 B1 | 6/2019 | Hodges |
| 10,335,121 B2 | 7/2019 | Desai |
| D856,512 S | 8/2019 | Cowart et al. |
| 10,376,406 B2 * | 8/2019 | Newton ................. A61F 5/453 |
| 10,376,407 B2 | 8/2019 | Newton |
| 10,390,989 B2 * | 8/2019 | Sanchez ................. A61F 5/453 |
| D858,144 S | 9/2019 | Fu |
| 10,406,039 B2 | 9/2019 | Villarreal |
| 10,407,222 B2 | 9/2019 | Allen |
| 10,478,356 B2 | 11/2019 | Griffin |
| 10,500,108 B1 | 12/2019 | Maschino et al. |
| 10,538,366 B2 | 1/2020 | Pentelovitch et al. |
| 10,569,938 B2 | 2/2020 | Zhao et al. |
| 10,577,156 B2 | 3/2020 | Dagnelie et al. |
| RE47,930 E | 4/2020 | Cho |
| 10,618,721 B2 | 4/2020 | Vazin |
| D884,390 S | 5/2020 | Wang |
| 10,669,079 B2 | 6/2020 | Freedman et al. |
| D892,315 S | 8/2020 | Airy |
| 10,730,672 B2 | 8/2020 | Bertram et al. |
| 10,737,848 B2 | 8/2020 | Philip et al. |
| 10,765,854 B2 | 9/2020 | Law et al. |
| 10,766,670 B2 | 9/2020 | Kittmann |
| 10,799,386 B1 * | 10/2020 | Harrison, Sr. .......... A61F 5/441 |
| 10,806,642 B2 | 10/2020 | Tagomori et al. |
| D901,214 S | 11/2020 | Hu |
| 10,849,799 B2 | 12/2020 | Nishikawa et al. |
| 10,857,025 B2 * | 12/2020 | Davis .................... A61F 5/451 |
| 10,865,017 B1 | 12/2020 | Cowart et al. |
| 10,889,412 B2 | 1/2021 | West et al. |
| 10,913,581 B2 | 2/2021 | Stahlecker |
| D912,244 S | 3/2021 | Rehm et al. |
| 10,952,889 B2 * | 3/2021 | Newton ................. A61F 5/4404 |
| 10,973,378 B2 | 4/2021 | Ryu et al. |
| 10,973,678 B2 * | 4/2021 | Newton ................. A61F 5/453 |
| 10,974,874 B2 | 4/2021 | Ragias et al. |
| 11,000,401 B2 | 5/2021 | Ecklund et al. |
| D923,365 S | 6/2021 | Wang |
| 11,026,829 B2 * | 6/2021 | Harvie .............. A61M 25/0017 |
| 11,027,900 B2 | 6/2021 | Liu |
| 11,045,346 B2 | 6/2021 | Argent et al. |
| D928,946 S * | 8/2021 | Sanchez ...................... D24/122 |
| 11,090,183 B2 | 8/2021 | Sanchez et al. |
| 11,160,695 B2 | 11/2021 | Febo et al. |
| 11,160,697 B2 | 11/2021 | Maschino et al. |
| 11,168,420 B2 | 11/2021 | Kinugasa et al. |
| 11,179,506 B2 | 11/2021 | Barr et al. |
| 11,207,206 B2 | 12/2021 | Sharma et al. |
| 11,226,376 B2 | 1/2022 | Yamauchi et al. |
| 11,253,389 B2 | 2/2022 | Sharma et al. |
| 11,253,407 B2 | 2/2022 | Miao et al. |
| 11,326,586 B2 | 5/2022 | Milner et al. |
| 11,369,508 B2 | 6/2022 | Ecklund et al. |
| 11,369,524 B2 | 6/2022 | Hubbard et al. |
| 11,376,152 B2 * | 7/2022 | Sanchez ................. A61F 5/453 |
| 11,382,786 B2 * | 7/2022 | Sanchez ................. A61F 5/4404 |
| 11,382,788 B2 | 7/2022 | Hjorth et al. |
| 11,389,318 B2 | 7/2022 | Radl et al. |
| 11,395,871 B2 | 7/2022 | Radl et al. |
| 11,399,990 B2 | 8/2022 | Suyama |
| 11,426,303 B2 * | 8/2022 | Davis ..................... A61B 5/208 |
| 11,504,265 B2 | 11/2022 | Godinez et al. |
| 11,529,252 B2 * | 12/2022 | Glithero ................. A61F 5/455 |
| 11,547,788 B2 | 1/2023 | Radl et al. |
| 11,806,266 B2 | 11/2023 | Sanchez et al. |
| 11,839,567 B2 | 12/2023 | Davis et al. |
| D1,010,109 S | 1/2024 | Ecklund et al. |
| 11,857,716 B2 | 1/2024 | Lee et al. |
| 11,865,030 B2 | 1/2024 | Davis et al. |
| 11,890,221 B2 | 2/2024 | Ulreich et al. |
| 11,925,575 B2 * | 3/2024 | Newton ................. A61F 5/4404 |
| 11,938,053 B2 | 3/2024 | Austermann et al. |
| 11,944,740 B2 | 4/2024 | Hughett et al. |
| 12,023,457 B2 | 7/2024 | Mann et al. |
| 12,042,422 B2 | 7/2024 | Davis et al. |
| D1,038,385 S | 8/2024 | Ecklund et al. |
| 12,090,083 B2 | 9/2024 | Ecklund et al. |
| 2001/0037097 A1 | 11/2001 | Cheng et al. |
| 2001/0054426 A1 | 12/2001 | Knudson et al. |
| 2002/0019614 A1 * | 2/2002 | Woon ................ A61F 13/53747 |
| | | 604/378 |
| 2002/0026161 A1 | 2/2002 | Grundke |
| 2002/0087131 A1 | 7/2002 | Wolff et al. |
| 2002/0091364 A1 | 7/2002 | Prabhakar |

(56) References Cited

U.S. PATENT DOCUMENTS

| | | |
|---|---|---|
| 2002/0189992 A1 | 12/2002 | Schmidt et al. |
| 2002/0193760 A1 | 12/2002 | Thompson |
| 2003/0004436 A1 | 1/2003 | Schmidt et al. |
| 2003/0032931 A1* | 2/2003 | Grundke ............... A61F 5/453 604/347 |
| 2003/0032944 A1 | 2/2003 | Cawood |
| 2003/0073964 A1 | 4/2003 | Palumbo et al. |
| 2003/0120178 A1 | 6/2003 | Heki |
| 2003/0157859 A1 | 8/2003 | Ishikawa |
| 2003/0181880 A1 | 9/2003 | Schwartz |
| 2003/0195484 A1 | 10/2003 | Harvie |
| 2003/0204173 A1 | 10/2003 | Burns et al. |
| 2003/0233079 A1 | 12/2003 | Parks et al. |
| 2004/0006321 A1 | 1/2004 | Cheng et al. |
| 2004/0015141 A1 | 1/2004 | Cheng et al. |
| 2004/0056122 A1 | 3/2004 | Male et al. |
| 2004/0084465 A1 | 5/2004 | Luburic |
| 2004/0127872 A1 | 7/2004 | Petryk et al. |
| 2004/0128749 A1 | 7/2004 | Scott |
| 2004/0143229 A1* | 7/2004 | Easter ............... A61F 5/451 604/322 |
| 2004/0147863 A1 | 7/2004 | Diaz et al. |
| 2004/0147894 A1 | 7/2004 | Mizutani et al. |
| 2004/0158221 A1 | 8/2004 | Mizutani et al. |
| 2004/0176731 A1 | 9/2004 | Cheng et al. |
| 2004/0176746 A1* | 9/2004 | Forral ............... A61F 5/453 604/544 |
| 2004/0191919 A1 | 9/2004 | Unger et al. |
| 2004/0200936 A1 | 10/2004 | Opperthauser |
| 2004/0207530 A1* | 10/2004 | Nielsen ............... A61F 13/42 340/573.5 |
| 2004/0236292 A1* | 11/2004 | Tazoe ............... A61F 5/451 604/317 |
| 2004/0243075 A1 | 12/2004 | Harvie |
| 2004/0254547 A1* | 12/2004 | Okabe ............... A61F 5/455 604/317 |
| 2005/0010182 A1 | 1/2005 | Parks et al. |
| 2005/0010197 A1 | 1/2005 | Lau et al. |
| 2005/0033248 A1* | 2/2005 | Machida ............... A61F 5/455 604/327 |
| 2005/0065471 A1 | 3/2005 | Kuntz |
| 2005/0070861 A1* | 3/2005 | Okabe ............... A61F 5/4404 604/327 |
| 2005/0070862 A1* | 3/2005 | Tazoe ............... A61F 5/455 604/327 |
| 2005/0082300 A1 | 4/2005 | Modrell et al. |
| 2005/0097662 A1 | 5/2005 | Leimkuhler et al. |
| 2005/0101924 A1 | 5/2005 | Elson et al. |
| 2005/0119630 A1 | 6/2005 | Harvie |
| 2005/0137557 A1 | 6/2005 | Swiecicki et al. |
| 2005/0154360 A1 | 7/2005 | Harvie |
| 2005/0177070 A1 | 8/2005 | Levinson et al. |
| 2005/0273920 A1 | 12/2005 | Marinas |
| 2005/0277904 A1 | 12/2005 | Chase et al. |
| 2005/0279359 A1 | 12/2005 | LeBlanc et al. |
| 2006/0004332 A1 | 1/2006 | Marx |
| 2006/0015080 A1 | 1/2006 | Mahnensmith |
| 2006/0015081 A1* | 1/2006 | Suzuki ............... A61F 5/451 604/329 |
| 2006/0016778 A1 | 1/2006 | Park |
| 2006/0069359 A1 | 3/2006 | Dipalma et al. |
| 2006/0079854 A1 | 4/2006 | Kay et al. |
| 2006/0111648 A1* | 5/2006 | Vermaak ............... A61B 10/007 604/355 |
| 2006/0155214 A1* | 7/2006 | Wightman ............... A61F 5/455 600/574 |
| 2006/0171997 A1 | 8/2006 | Gruenbacher et al. |
| 2006/0200102 A1 | 9/2006 | Cooper |
| 2006/0229575 A1 | 10/2006 | Boiarski |
| 2006/0229576 A1 | 10/2006 | Conway et al. |
| 2006/0231648 A1 | 10/2006 | Male et al. |
| 2006/0235266 A1 | 10/2006 | Nan |
| 2006/0235359 A1 | 10/2006 | Marland |
| 2006/0241553 A1 | 10/2006 | Harvie |
| 2006/0269439 A1 | 11/2006 | White |
| 2006/0277670 A1 | 12/2006 | Baker et al. |
| 2007/0006368 A1 | 1/2007 | Key et al. |
| 2007/0010797 A1 | 1/2007 | Nishtala et al. |
| 2007/0016152 A1 | 1/2007 | Karpowicz et al. |
| 2007/0038194 A1* | 2/2007 | Wada ............... A61F 5/451 604/347 |
| 2007/0055209 A1 | 3/2007 | Patel et al. |
| 2007/0073252 A1 | 3/2007 | Forgrave |
| 2007/0117880 A1 | 5/2007 | Elson et al. |
| 2007/0118993 A1 | 5/2007 | Bates |
| 2007/0135786 A1 | 6/2007 | Schmidt et al. |
| 2007/0137718 A1 | 6/2007 | Rushlander et al. |
| 2007/0149935 A1 | 6/2007 | Dirico |
| 2007/0191804 A1 | 8/2007 | Coley |
| 2007/0203464 A1 | 8/2007 | Green et al. |
| 2007/0214553 A1* | 9/2007 | Carromba ............... A47K 11/12 4/144.4 |
| 2007/0225663 A1 | 9/2007 | Watt et al. |
| 2007/0225666 A1 | 9/2007 | Otto |
| 2007/0225668 A1 | 9/2007 | Otto |
| 2007/0266486 A1 | 11/2007 | Ramirez |
| 2007/0282309 A1 | 12/2007 | Bengtson et al. |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1* | 2/2008 | Okabe ............... A61F 5/4404 604/378 |
| 2008/0041869 A1 | 2/2008 | Backaert |
| 2008/0091153 A1* | 4/2008 | Harvie ............... A61F 5/451 604/318 |
| 2008/0091158 A1 | 4/2008 | Yang |
| 2008/0114327 A1 | 5/2008 | Barge |
| 2008/0167634 A1 | 7/2008 | Kouta et al. |
| 2008/0183157 A1 | 7/2008 | Walters |
| 2008/0215031 A1 | 9/2008 | Belfort et al. |
| 2008/0234642 A1 | 9/2008 | Patterson et al. |
| 2008/0269703 A1 | 10/2008 | Collins et al. |
| 2008/0281282 A1 | 11/2008 | Finger et al. |
| 2008/0287894 A1* | 11/2008 | Van Den Heuvel .... A61F 5/455 604/327 |
| 2008/0312550 A1 | 12/2008 | Nishtala et al. |
| 2009/0025717 A1 | 1/2009 | Pinel |
| 2009/0048570 A1 | 2/2009 | Jensen |
| 2009/0056003 A1 | 3/2009 | Ivie et al. |
| 2009/0069761 A1 | 3/2009 | Vogel |
| 2009/0069765 A1 | 3/2009 | Wortham |
| 2009/0120179 A1 | 5/2009 | Nylander et al. |
| 2009/0192482 A1* | 7/2009 | Dodge, II ......... A61F 13/53708 524/436 |
| 2009/0234312 A1 | 9/2009 | Otoole et al. |
| 2009/0251510 A1 | 10/2009 | Noro et al. |
| 2009/0264840 A1 | 10/2009 | Virginio |
| 2009/0270822 A1* | 10/2009 | Medeiros ............... A61F 5/451 604/347 |
| 2009/0281510 A1 | 11/2009 | Fisher |
| 2009/0283982 A1 | 11/2009 | Thomas |
| 2010/0004612 A1* | 1/2010 | Thevenin ............... A61F 13/84 4/443 |
| 2010/0058660 A1 | 3/2010 | Williams |
| 2010/0121289 A1 | 5/2010 | Parks et al. |
| 2010/0158168 A1 | 6/2010 | Murthy et al. |
| 2010/0160882 A1 | 6/2010 | Lowe |
| 2010/0174250 A1 | 7/2010 | Hu et al. |
| 2010/0179493 A1 | 7/2010 | Heagle et al. |
| 2010/0185168 A1* | 7/2010 | Graauw ............... A61F 5/4556 604/347 |
| 2010/0198172 A1 | 8/2010 | Wada et al. |
| 2010/0211032 A1* | 8/2010 | Tsai ............... A61F 5/453 604/319 |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028920 A1 | 2/2011 | Johannison |
| 2011/0028922 A1 | 2/2011 | Kay et al. |
| 2011/0034889 A1 | 2/2011 | Smith |
| 2011/0036837 A1 | 2/2011 | Shang |

(56) References Cited

U.S. PATENT DOCUMENTS

| | | | |
|---|---|---|---|
| 2011/0040267 A1* | 2/2011 | Wada | A61F 5/4401 604/318 |
| 2011/0040271 A1* | 2/2011 | Rogers | A61F 5/4556 604/346 |
| 2011/0054426 A1 | 3/2011 | Stewart et al. | |
| 2011/0060299 A1 | 3/2011 | Wada et al. | |
| 2011/0060300 A1* | 3/2011 | Weig | A61F 5/451 604/319 |
| 2011/0077495 A1 | 3/2011 | Gilbert | |
| 2011/0077606 A1 | 3/2011 | Wilcox et al. | |
| 2011/0087337 A1 | 4/2011 | Forsell | |
| 2011/0145993 A1 | 6/2011 | Rader et al. | |
| 2011/0152802 A1 | 6/2011 | Dicamillo et al. | |
| 2011/0164147 A1 | 7/2011 | Takahashi et al. | |
| 2011/0172620 A1 | 7/2011 | Khambatta | |
| 2011/0172625 A1* | 7/2011 | Wada | A61F 13/42 604/385.01 |
| 2011/0202024 A1 | 8/2011 | Cozzens | |
| 2011/0238023 A1 | 9/2011 | Slayton | |
| 2011/0240648 A1 | 10/2011 | Tucker | |
| 2011/0251572 A1 | 10/2011 | Nishtala et al. | |
| 2011/0265889 A1 | 11/2011 | Tanaka et al. | |
| 2011/0276020 A1 | 11/2011 | Mitsui | |
| 2012/0029452 A1* | 2/2012 | Rodsten | A61F 5/453 604/327 |
| 2012/0035577 A1 | 2/2012 | Tomes et al. | |
| 2012/0041400 A1 | 2/2012 | Christensen | |
| 2012/0059328 A1 | 3/2012 | Dikeman et al. | |
| 2012/0066825 A1 | 3/2012 | Birbara et al. | |
| 2012/0103347 A1* | 5/2012 | Wheaton | A61F 5/453 128/885 |
| 2012/0116336 A1 | 5/2012 | Sharma et al. | |
| 2012/0137420 A1 | 6/2012 | Gordon et al. | |
| 2012/0165768 A1 | 6/2012 | Sekiyama et al. | |
| 2012/0209216 A1 | 8/2012 | Jensen et al. | |
| 2012/0210503 A1* | 8/2012 | Anzivino, Sr. | A61F 5/4556 4/144.3 |
| 2012/0233761 A1 | 9/2012 | Huang | |
| 2012/0245541 A1* | 9/2012 | Suzuki | A61F 13/42 604/319 |
| 2012/0245542 A1* | 9/2012 | Suzuki | A61F 13/84 374/45 |
| 2012/0245547 A1 | 9/2012 | Wilcox et al. | |
| 2012/0253303 A1* | 10/2012 | Suzuki | A61F 13/42 374/45 |
| 2012/0271259 A1 | 10/2012 | Ulert | |
| 2012/0296305 A1 | 11/2012 | Barraza Khaled et al. | |
| 2012/0316522 A1 | 12/2012 | Carter et al. | |
| 2012/0330256 A1 | 12/2012 | Wilcox et al. | |
| 2013/0006206 A1* | 1/2013 | Wada | A61F 13/535 604/385.01 |
| 2013/0045651 A1 | 2/2013 | Esteves et al. | |
| 2013/0053804 A1 | 2/2013 | Soerensen et al. | |
| 2013/0096523 A1 | 4/2013 | Chang et al. | |
| 2013/0110059 A1 | 5/2013 | Kossow et al. | |
| 2013/0138064 A1 | 5/2013 | Stroebech et al. | |
| 2013/0150813 A1 | 6/2013 | Gordon et al. | |
| 2013/0218112 A1 | 8/2013 | Thompson | |
| 2013/0245496 A1 | 9/2013 | Wells et al. | |
| 2013/0245586 A1 | 9/2013 | Jha | |
| 2013/0292537 A1 | 11/2013 | Dirico | |
| 2013/0330501 A1 | 12/2013 | Aizenberg et al. | |
| 2014/0005647 A1 | 1/2014 | Shuffler et al. | |
| 2014/0031774 A1* | 1/2014 | Bengtson | A61M 1/90 604/319 |
| 2014/0039432 A1 | 2/2014 | Dunbar et al. | |
| 2014/0107599 A1 | 4/2014 | Fink et al. | |
| 2014/0157499 A1 | 6/2014 | Suzuki et al. | |
| 2014/0171889 A1 | 6/2014 | Hopman et al. | |
| 2014/0182051 A1* | 7/2014 | Tanimoto | A61G 9/006 4/144.3 |
| 2014/0196189 A1 | 7/2014 | Lee et al. | |
| 2014/0303582 A1 | 10/2014 | Wright et al. | |
| 2014/0316381 A1 | 10/2014 | Reglin | |
| 2014/0325746 A1 | 11/2014 | Block | |
| 2014/0348139 A1 | 11/2014 | Gomez Martinez | |
| 2014/0352050 A1 | 12/2014 | Yao et al. | |
| 2014/0371628 A1 | 12/2014 | Desai | |
| 2015/0045757 A1 | 2/2015 | Lee et al. | |
| 2015/0047114 A1 | 2/2015 | Ramirez | |
| 2015/0048089 A1 | 2/2015 | Robertson | |
| 2015/0135423 A1 | 5/2015 | Sharpe et al. | |
| 2015/0157300 A1 | 6/2015 | Ealovega et al. | |
| 2015/0209194 A1 | 7/2015 | Heyman | |
| 2015/0290425 A1 | 10/2015 | Macy et al. | |
| 2015/0320583 A1 | 11/2015 | Harvie | |
| 2015/0329255 A1 | 11/2015 | Rzepecki | |
| 2015/0342799 A1 | 12/2015 | Michiels et al. | |
| 2015/0359660 A1* | 12/2015 | Harvie | A61F 5/441 604/351 |
| 2015/0366699 A1 | 12/2015 | Nelson | |
| 2016/0029998 A1 | 2/2016 | Brister et al. | |
| 2016/0030228 A1 | 2/2016 | Jones | |
| 2016/0038356 A1 | 2/2016 | Yao et al. | |
| 2016/0058322 A1 | 3/2016 | Brister et al. | |
| 2016/0060001 A1 | 3/2016 | Wada et al. | |
| 2016/0100976 A1 | 4/2016 | Conway et al. | |
| 2016/0106604 A1* | 4/2016 | Timm | A61F 13/84 604/385.01 |
| 2016/0113809 A1 | 4/2016 | Kim | |
| 2016/0183689 A1 | 6/2016 | Miner | |
| 2016/0256022 A1 | 9/2016 | Le | |
| 2016/0270982 A1 | 9/2016 | Raycheck et al. | |
| 2016/0278662 A1 | 9/2016 | Brister et al. | |
| 2016/0357400 A1 | 12/2016 | Penha et al. | |
| 2016/0366699 A1 | 12/2016 | Zhang et al. | |
| 2016/0367226 A1* | 12/2016 | Newton | A01K 23/005 |
| 2016/0367411 A1 | 12/2016 | Justiz et al. | |
| 2016/0374848 A1* | 12/2016 | Sanchez | A61F 5/453 604/319 |
| 2017/0007438 A1* | 1/2017 | Harvie | A61F 5/453 |
| 2017/0014560 A1 | 1/2017 | Minskoff et al. | |
| 2017/0100276 A1 | 4/2017 | Joh | |
| 2017/0128638 A1 | 5/2017 | Giezendanner et al. | |
| 2017/0136209 A1 | 5/2017 | Burnett et al. | |
| 2017/0143534 A1 | 5/2017 | Sanchez | |
| 2017/0165100 A1 | 6/2017 | Jackson et al. | |
| 2017/0165405 A1 | 6/2017 | Muser et al. | |
| 2017/0189225 A1 | 7/2017 | Voorhees et al. | |
| 2017/0202692 A1 | 7/2017 | Laniado | |
| 2017/0216081 A1 | 8/2017 | Accosta | |
| 2017/0246026 A1 | 8/2017 | Laniado | |
| 2017/0252014 A1 | 9/2017 | Siller Gonzalez et al. | |
| 2017/0252202 A9 | 9/2017 | Sanchez et al. | |
| 2017/0266031 A1* | 9/2017 | Sanchez | A61F 5/443 |
| 2017/0266658 A1 | 9/2017 | Bruno et al. | |
| 2017/0281399 A1* | 10/2017 | VanMiddendorp | A61M 1/80 |
| 2017/0312116 A1 | 11/2017 | Laniado | |
| 2017/0325788 A1 | 11/2017 | Ealovega et al. | |
| 2017/0333244 A1 | 11/2017 | Laniado | |
| 2017/0042748 A1 | 12/2017 | Griffin | |
| 2017/0348139 A1* | 12/2017 | Newton | A61F 5/4404 |
| 2017/0354532 A1 | 12/2017 | Holt | |
| 2017/0354551 A1 | 12/2017 | Gawley et al. | |
| 2017/0367873 A1 | 12/2017 | Grannum | |
| 2018/0002075 A1 | 1/2018 | Lee | |
| 2018/0008451 A1 | 1/2018 | Stroebech | |
| 2018/0008804 A1 | 1/2018 | Laniado | |
| 2018/0021218 A1 | 1/2018 | Brosch et al. | |
| 2018/0028349 A1* | 2/2018 | Newton | A61M 1/88 |
| 2018/0037384 A1 | 2/2018 | Archeny et al. | |
| 2018/0049910 A1 | 2/2018 | Newton | |
| 2018/0064572 A1 | 3/2018 | Wiltshire | |
| 2018/0104131 A1 | 4/2018 | Killian | |
| 2018/0127187 A1 | 5/2018 | Sewell | |
| 2018/0193215 A1 | 7/2018 | Davies et al. | |
| 2018/0200101 A1 | 7/2018 | Su | |
| 2018/0228642 A1* | 8/2018 | Davis | A61F 5/455 |
| 2018/0256384 A1 | 9/2018 | Kasirye | |
| 2018/0271694 A1 | 9/2018 | Fernandez et al. | |
| 2018/0317892 A1 | 11/2018 | Catlin | |
| 2018/0325748 A1 | 11/2018 | Sharma et al. | |
| 2019/0001030 A1 | 1/2019 | Braga et al. | |

(56) References Cited

U.S. PATENT DOCUMENTS

| | | |
|---|---|---|
| 2019/0021899 A1 | 1/2019 | Met |
| 2019/0038451 A1* | 2/2019 | Harvie .................. A61F 5/441 |
| 2019/0046102 A1 | 2/2019 | Kushnir et al. |
| 2019/0059938 A1 | 2/2019 | Holsten |
| 2019/0091059 A1 | 3/2019 | Gabriel |
| 2019/0100362 A1 | 4/2019 | Meyers et al. |
| 2019/0133814 A1 | 5/2019 | Tammen et al. |
| 2019/0142624 A1* | 5/2019 | Sanchez .................. A61F 5/453 604/319 |
| 2019/0224036 A1* | 7/2019 | Sanchez .................. A61F 5/455 |
| 2019/0247222 A1 | 8/2019 | Ecklund et al. |
| 2019/0247223 A1 | 8/2019 | Brun et al. |
| 2019/0282391 A1 | 9/2019 | Johannes et al. |
| 2019/0314189 A1 | 10/2019 | Acosta |
| 2019/0314190 A1* | 10/2019 | Sanchez .................. A61F 5/453 |
| 2019/0321587 A1 | 10/2019 | Mcmenamin et al. |
| 2019/0344934 A1 | 11/2019 | Faerber et al. |
| 2019/0365307 A1 | 12/2019 | Laing et al. |
| 2019/0365561 A1 | 12/2019 | Newton et al. |
| 2019/0374373 A1 | 12/2019 | Joh |
| 2020/0008985 A1 | 1/2020 | Nguyen et al. |
| 2020/0016012 A1 | 1/2020 | Dutkiewicz |
| 2020/0030595 A1 | 1/2020 | Boukidjian et al. |
| 2020/0046544 A1* | 2/2020 | Godinez .................. A61F 5/455 |
| 2020/0055638 A1 | 2/2020 | Lau et al. |
| 2020/0070392 A1 | 3/2020 | Huber et al. |
| 2020/0085609 A1 | 3/2020 | Schelch et al. |
| 2020/0085610 A1 | 3/2020 | Cohn et al. |
| 2020/0086090 A1 | 3/2020 | Von Weymarn-schärli et al. |
| 2020/0107518 A1 | 4/2020 | Hiroshima et al. |
| 2020/0129322 A1 | 4/2020 | Leuckel |
| 2020/0171217 A9 | 6/2020 | Braga et al. |
| 2020/0206015 A1 | 7/2020 | Langer |
| 2020/0206039 A1 | 7/2020 | Mclain |
| 2020/0214910 A1 | 7/2020 | Varona et al. |
| 2020/0216898 A1 | 7/2020 | Hubbell |
| 2020/0216989 A1 | 7/2020 | Kinugasa et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0246172 A1 | 8/2020 | Ho |
| 2020/0246203 A1 | 8/2020 | Tulk et al. |
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1* | 10/2020 | Newton .................. A61M 1/88 |
| 2020/0315837 A1 | 10/2020 | Radl et al. |
| 2020/0315838 A1 | 10/2020 | Eckert |
| 2020/0315872 A1 | 10/2020 | Viens et al. |
| 2020/0315874 A1 | 10/2020 | Viens et al. |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0375781 A1* | 12/2020 | Staali .................. A61M 1/71 |
| 2020/0375810 A1 | 12/2020 | Carlin et al. |
| 2020/0385179 A1 | 12/2020 | Mccourt |
| 2020/0390591 A1* | 12/2020 | Glithero ................ A61F 5/4401 |
| 2020/0390592 A1 | 12/2020 | Merrill |
| 2020/0405521 A1 | 12/2020 | Glasroe |
| 2021/0008771 A1 | 1/2021 | Huber et al. |
| 2021/0009323 A1 | 1/2021 | Markarian et al. |
| 2021/0020072 A1 | 1/2021 | Moehring et al. |
| 2021/0023279 A1 | 1/2021 | Radl et al. |
| 2021/0059853 A1* | 3/2021 | Davis .................. A61F 5/4408 |
| 2021/0061523 A1 | 3/2021 | Bytheway |
| 2021/0069005 A1* | 3/2021 | Sanchez .................. A61F 5/453 |
| 2021/0069008 A1* | 3/2021 | Blabas .................. A61F 5/455 |
| 2021/0069009 A1 | 3/2021 | Im |
| 2021/0069030 A1 | 3/2021 | Nishikawa et al. |
| 2021/0077993 A1 | 3/2021 | Nazareth et al. |
| 2021/0113749 A1 | 4/2021 | Radl et al. |
| 2021/0121318 A1 | 4/2021 | Pinlac |
| 2021/0137724 A1 | 5/2021 | Ecklund et al. |
| 2021/0138190 A1 | 5/2021 | Erbey et al. |
| 2021/0154055 A1 | 5/2021 | Villarreal |
| 2021/0170079 A1 | 6/2021 | Radl et al. |
| 2021/0178390 A1 | 6/2021 | Oueslati et al. |
| 2021/0186742 A1 | 6/2021 | Newton et al. |
| 2021/0212865 A1 | 7/2021 | Wallajapet et al. |
| 2021/0220162 A1* | 7/2021 | Jamison .................. A61F 5/453 |
| 2021/0220163 A1 | 7/2021 | Mayrand |
| 2021/0228400 A1 | 7/2021 | Glithero |
| 2021/0228401 A1 | 7/2021 | Becker et al. |
| 2021/0228795 A1* | 7/2021 | Hughett .................. A61F 5/451 |
| 2021/0229877 A1 | 7/2021 | Ragias et al. |
| 2021/0236323 A1* | 8/2021 | Austermann .......... A61F 5/455 |
| 2021/0236324 A1 | 8/2021 | Sweeney |
| 2021/0251814 A1 | 8/2021 | Jönegren et al. |
| 2021/0267787 A1 | 9/2021 | Nazemi |
| 2021/0275343 A1* | 9/2021 | Sanchez .................. A61F 5/4404 |
| 2021/0275344 A1 | 9/2021 | Wing |
| 2021/0290454 A1 | 9/2021 | Yamada |
| 2021/0315727 A1 | 10/2021 | Jiang |
| 2021/0353450 A1* | 11/2021 | Sharma .................. A61F 5/453 |
| 2021/0361469 A1 | 11/2021 | Liu et al. |
| 2021/0369495 A1* | 12/2021 | Cheng .................. A61M 1/80 |
| 2021/0386925 A1 | 12/2021 | Hartwell et al. |
| 2021/0393433 A1 | 12/2021 | Godinez et al. |
| 2022/0023091 A1 | 1/2022 | Ecklund et al. |
| 2022/0031523 A1 | 2/2022 | Pierpoint |
| 2022/0039995 A1 | 2/2022 | Johannes et al. |
| 2022/0047410 A1 | 2/2022 | Walthall |
| 2022/0062027 A1 | 3/2022 | Mitchell et al. |
| 2022/0062028 A1* | 3/2022 | Mitchell ................ A61F 5/4405 |
| 2022/0062029 A1* | 3/2022 | Johannes .............. A61F 5/4401 |
| 2022/0066825 A1 | 3/2022 | Saraf et al. |
| 2022/0071811 A1* | 3/2022 | Cheng .................. A61F 5/453 |
| 2022/0071826 A1 | 3/2022 | Kulkarni et al. |
| 2022/0104965 A1 | 4/2022 | Vaninetti et al. |
| 2022/0104976 A1 | 4/2022 | Hoeger et al. |
| 2022/0104981 A1 | 4/2022 | Jones |
| 2022/0117773 A1 | 4/2022 | Davis et al. |
| 2022/0117774 A1* | 4/2022 | Meyer .................. A61F 5/455 |
| 2022/0117775 A1* | 4/2022 | Jones .................. A61L 26/0009 |
| 2022/0133524 A1* | 5/2022 | Davis .................. A61M 1/80 604/319 |
| 2022/0151817 A1* | 5/2022 | Mann .................. A61F 5/451 |
| 2022/0160949 A1 | 5/2022 | Simiele et al. |
| 2022/0168159 A1 | 6/2022 | Triado et al. |
| 2022/0193312 A1 | 6/2022 | Lee et al. |
| 2022/0211536 A1 | 7/2022 | Johannes et al. |
| 2022/0218510 A1 | 7/2022 | Metzger et al. |
| 2022/0229053 A1 | 7/2022 | Levin et al. |
| 2022/0241106 A1 | 8/2022 | Johannes et al. |
| 2022/0247407 A1 | 8/2022 | Yamamoto et al. |
| 2022/0248836 A1 | 8/2022 | Cagle et al. |
| 2022/0257407 A1* | 8/2022 | Johannes .............. A61F 5/453 |
| 2022/0265460 A1 | 8/2022 | Coker |
| 2022/0265462 A1* | 8/2022 | Alder .................. A61F 5/4404 |
| 2022/0270711 A1 | 8/2022 | Feala et al. |
| 2022/0273482 A1 | 9/2022 | Johannes et al. |
| 2022/0280357 A1* | 9/2022 | Jagannathan .......... A61F 13/84 |
| 2022/0287689 A1 | 9/2022 | Johannes |
| 2022/0287867 A1* | 9/2022 | Jones .................. A61F 5/4405 |
| 2022/0287868 A1 | 9/2022 | Garvey et al. |
| 2022/0296408 A1 | 9/2022 | Evans et al. |
| 2022/0305191 A1 | 9/2022 | Joseph et al. |
| 2022/0313222 A1* | 10/2022 | Austermann .......... A61B 10/007 |
| 2022/0313474 A1 | 10/2022 | Kriscovich et al. |
| 2022/0331170 A1 | 10/2022 | Erdem et al. |
| 2022/0339024 A1 | 10/2022 | Johannes et al. |
| 2022/0354685 A1* | 11/2022 | Davis .................. A61B 5/208 |
| 2022/0362049 A1 | 11/2022 | Austermann et al. |
| 2022/0370231 A1 | 11/2022 | Wang et al. |
| 2022/0370234 A1* | 11/2022 | Hughett .................. A61F 5/451 |
| 2022/0370235 A1* | 11/2022 | Johannes .............. A61F 5/453 |
| 2022/0370237 A1 | 11/2022 | Parmar et al. |
| 2022/0387001 A1* | 12/2022 | Askenazi .............. A61F 5/455 |
| 2022/0395390 A1 | 12/2022 | Brooks |
| 2022/0395391 A1* | 12/2022 | Saunders .............. A61F 5/4404 |
| 2022/0409422 A1 | 12/2022 | Schneider et al. |
| 2023/0018845 A1 | 1/2023 | Lee |

(56) References Cited

U.S. PATENT DOCUMENTS

| | | |
|---|---|---|
| 2023/0020563 A1* | 1/2023 | Sharma .............. A61F 5/443 |
| 2023/0031640 A1 | 2/2023 | Hughett et al. |
| 2023/0037159 A1 | 2/2023 | Brennan et al. |
| 2023/0052238 A1 | 2/2023 | Oluwasogo |
| 2023/0062994 A1* | 3/2023 | Ecklund .............. A61F 5/453 |
| 2023/0070347 A1 | 3/2023 | Watson et al. |
| 2023/0073708 A1 | 3/2023 | Xu et al. |
| 2023/0089032 A1* | 3/2023 | Hughett .............. A61F 5/451 |
| | | 604/319 |
| 2023/0099821 A1 | 3/2023 | Radl et al. |
| 2023/0099991 A1 | 3/2023 | Bianchi et al. |
| 2023/0105001 A1 | 4/2023 | Whittome et al. |
| 2023/0110577 A1 | 4/2023 | Choi |
| 2023/0138269 A1* | 5/2023 | Abdelal .............. A61F 5/451 |
| | | 604/347 |
| 2023/0145365 A1 | 5/2023 | Martin et al. |
| 2023/0155253 A1 | 5/2023 | Yin et al. |
| 2023/0210504 A1 | 7/2023 | Kuroda et al. |
| 2023/0210685 A1 | 7/2023 | Fallows et al. |
| 2023/0218426 A1 | 7/2023 | Hughett |
| 2023/0240884 A1 | 8/2023 | Davis et al. |
| 2023/0248562 A1 | 8/2023 | Sanchez et al. |
| 2023/0248564 A1* | 8/2023 | Mann .............. A61F 5/443 |
| | | 604/349 |
| 2023/0255812 A1 | 8/2023 | Sanchez et al. |
| 2023/0255813 A1 | 8/2023 | Sanchez et al. |
| 2023/0255815 A1 | 8/2023 | Newton |
| 2023/0263650 A1 | 8/2023 | Sanchez et al. |
| 2023/0263655 A1* | 8/2023 | Johannes .............. A61F 5/455 |
| | | 604/347 |
| 2023/0277362 A1* | 9/2023 | Davis .............. A61B 5/208 |
| | | 604/319 |
| 2023/0285178 A1 | 9/2023 | Sanchez et al. |
| 2023/0293339 A1 | 9/2023 | James |
| 2023/0301846 A1 | 9/2023 | Greenwood |
| 2023/0355423 A1 | 11/2023 | Stevenson et al. |
| 2023/0404791 A1 | 12/2023 | Ecklund et al. |
| 2024/0008444 A1 | 1/2024 | Su et al. |
| 2024/0009023 A1 | 1/2024 | Johannes et al. |
| 2024/0024170 A1 | 1/2024 | Scott |
| 2024/0041638 A1 | 2/2024 | Johannes et al. |
| 2024/0058161 A1 | 2/2024 | Ulreich et al. |
| 2024/0065881 A1 | 2/2024 | Kuroda et al. |
| 2024/0099874 A1 | 3/2024 | Sanchez et al. |
| 2024/0110318 A1 | 4/2024 | Bendt et al. |
| 2024/0123134 A1 | 4/2024 | Kharkar et al. |
| 2024/0261131 A1 | 8/2024 | Garvey et al. |

FOREIGN PATENT DOCUMENTS

| | | |
|---|---|---|
| CA | 2165286 C | 9/1999 |
| CA | 2354132 A1 | 6/2000 |
| CA | 2359091 C | 9/2003 |
| CA | 2488867 C | 8/2007 |
| CA | 3050918 A1 | 8/2018 |
| CA | 3098571 A1 | 11/2019 |
| CN | 2269203 Y | 12/1997 |
| CN | 1332620 A | 1/2002 |
| CN | 1434693 A | 8/2003 |
| CN | 1533755 A | 10/2004 |
| CN | 1602825 A | 4/2005 |
| CN | 1720888 A | 1/2006 |
| CN | 2936204 Y | 8/2007 |
| CN | 101262836 A | 9/2008 |
| CN | 101522148 A | 9/2009 |
| CN | 102159159 A | 8/2011 |
| CN | 202184840 U | 4/2012 |
| CN | 102481441 A | 5/2012 |
| CN | 202463712 U | 10/2012 |
| CN | 202950810 U | 5/2013 |
| CN | 103533968 A | 1/2014 |
| CN | 103717180 A | 4/2014 |
| CN | 204562697 U | 8/2015 |
| CN | 105411783 A | 3/2016 |
| CN | 105451693 A | 3/2016 |
| CN | 105534632 A | 5/2016 |
| CN | 106132360 A | 11/2016 |
| CN | 205849719 U | 1/2017 |
| CN | 106726089 A | 5/2017 |
| CN | 107847384 A | 3/2018 |
| CN | 107920912 A | 4/2018 |
| CN | 108420590 A | 8/2018 |
| CN | 209285902 U | 8/2019 |
| CN | 110381883 A | 10/2019 |
| CN | 211198839 U | 8/2020 |
| CN | 112566550 A | 3/2021 |
| CN | 112603184 A | 4/2021 |
| CN | 114007493 A | 2/2022 |
| CN | 114375187 A | 4/2022 |
| CN | 116096332 A | 5/2023 |
| DE | 1516466 A1 | 6/1969 |
| DE | 2721330 A1 | 11/1977 |
| DE | 2742298 A1 | 3/1978 |
| DE | 9407554.9 U1 | 5/1995 |
| DE | 4443710 A1 | 6/1995 |
| DE | 4416094 A1 | 11/1995 |
| DE | 4236097 C2 | 10/1996 |
| DE | 19619597 A1 | 11/1997 |
| DE | 102005037762 B3 | 9/2006 |
| DE | 102011103783 A1 | 12/2012 |
| DE | 102012112818 A1 | 6/2014 |
| DE | 202015104597 U1 | 7/2016 |
| DK | 9600118 | 11/1996 |
| EP | 0032138 A2 | 7/1981 |
| EP | 0066070 B1 | 12/1982 |
| EP | 0068712 A1 | 1/1983 |
| EP | 0140470 A1 | 5/1985 |
| EP | 0140471 B1 | 5/1988 |
| EP | 0274753 A2 | 7/1988 |
| EP | 0119143 B1 | 11/1988 |
| EP | 0483592 A1 | 5/1992 |
| EP | 0610638 A1 | 8/1994 |
| EP | 0613355 A1 | 9/1994 |
| EP | 0613355 B1 | 1/1997 |
| EP | 0787472 A1 | 8/1997 |
| EP | 0966936 A1 | 12/1999 |
| EP | 0987293 A1 | 3/2000 |
| EP | 1063953 A1 | 1/2001 |
| EP | 0653928 B1 | 10/2002 |
| EP | 1332738 A1 | 8/2003 |
| EP | 1382318 A1 | 1/2004 |
| EP | 1089684 B1 | 10/2004 |
| EP | 1616542 A1 | 1/2006 |
| EP | 1382318 B1 | 5/2006 |
| EP | 1063953 B1 | 1/2007 |
| EP | 1872752 A1 | 1/2008 |
| EP | 2180907 A1 | 5/2010 |
| EP | 2380532 A1 | 10/2011 |
| EP | 2389908 A1 | 11/2011 |
| EP | 2601916 A1 | 6/2013 |
| EP | 2676643 A1 | 12/2013 |
| EP | 2997950 A2 | 3/2016 |
| EP | 2879534 B1 | 3/2017 |
| EP | 3424471 A1 | 1/2019 |
| EP | 3169292 B1 | 11/2019 |
| EP | 3753492 A1 | 12/2020 |
| EP | 3788992 A1 | 3/2021 |
| EP | 3576689 B1 | 3/2022 |
| EP | 3752110 B1 | 3/2022 |
| EP | 3787570 B1 | 3/2022 |
| EP | 4025163 A1 | 7/2022 |
| EP | 3463180 B1 | 3/2023 |
| EP | 3569205 B1 | 6/2023 |
| EP | 4382082 A2 | 6/2024 |
| EP | 4445881 A2 | 10/2024 |
| GB | 871820 A | 7/1961 |
| GB | 1011517 A | 12/1965 |
| GB | 1467144 A | 3/1977 |
| GB | 2106395 A | 4/1983 |
| GB | 2106784 A | 4/1983 |
| GB | 2148126 A | 5/1985 |
| GB | 2171315 A | 8/1986 |
| GB | 2181953 A | 5/1987 |

(56) References Cited

FOREIGN PATENT DOCUMENTS

| | | | |
|---|---|---|---|
| GB | 2148126 B | 7/1987 |
| GB | 2191095 A | 12/1987 |
| GB | 2199750 A | 7/1988 |
| GB | 2260907 A | 5/1993 |
| GB | 2462267 A | 2/2010 |
| GB | 2469496 A | 10/2010 |
| GB | 2490327 A | 10/2012 |
| GB | 2507318 A | 4/2014 |
| GB | 2612752 A | 5/2023 |
| IT | 201800009129 A1 | 4/2020 |
| JP | S498638 U | 1/1974 |
| JP | S5410596 A | 1/1979 |
| JP | S5410596 Y2 | 5/1979 |
| JP | S54155729 U | 10/1979 |
| JP | S55155618 A | 12/1980 |
| JP | S57142534 U | 9/1982 |
| JP | S5888596 U | 6/1983 |
| JP | S58188016 U | 12/1983 |
| JP | S63107780 U | 7/1988 |
| JP | H0267530 A | 3/1990 |
| JP | H02103871 A | 4/1990 |
| JP | H02131422 A | 5/1990 |
| JP | H02131422 U | 11/1990 |
| JP | H0460220 A | 2/1992 |
| JP | H05123349 A | 5/1993 |
| JP | H05123350 A | 5/1993 |
| JP | H0626264 U | 4/1994 |
| JP | 3087938 B2 | 10/1995 |
| JP | H085630 A | 1/1996 |
| JP | H1040141 A | 2/1998 |
| JP | H10225430 A | 8/1998 |
| JP | H11113946 A | 4/1999 |
| JP | H11290365 A | 10/1999 |
| JP | 2000116690 A | 4/2000 |
| JP | 2000185068 A | 7/2000 |
| JP | 2001054531 A | 2/2001 |
| JP | 2001070331 A | 3/2001 |
| JP | 2001224616 A | 8/2001 |
| JP | 2001276107 A | 10/2001 |
| JP | 2001276108 A | 10/2001 |
| JP | 2002028173 A | 1/2002 |
| JP | 2003038563 A | 2/2003 |
| JP | 2003505152 A | 2/2003 |
| JP | 2003126242 A | 5/2003 |
| JP | 2003180722 A | 7/2003 |
| JP | 2003528691 A | 9/2003 |
| JP | 2004057578 A | 2/2004 |
| JP | 2004130056 A | 4/2004 |
| JP | 2004267530 A | 9/2004 |
| JP | 2005052219 A | 3/2005 |
| JP | 2005066011 A | 3/2005 |
| JP | 2005066325 A | 3/2005 |
| JP | 2005102978 A | 4/2005 |
| JP | 2005518237 A | 6/2005 |
| JP | 3749097 B2 | 12/2005 |
| JP | 2006026108 A | 2/2006 |
| JP | 3123547 B2 | 6/2006 |
| JP | 2006136492 A | 6/2006 |
| JP | 2006204868 A | 8/2006 |
| JP | 2007044494 A | 2/2007 |
| JP | 3132659 B2 | 5/2007 |
| JP | 2007209687 A | 8/2007 |
| JP | 4039641 B2 | 11/2007 |
| JP | 2008005975 A | 1/2008 |
| JP | 2009509570 A | 3/2009 |
| JP | 2009165887 A | 7/2009 |
| JP | 2009525776 A | 7/2009 |
| JP | 2010504150 A | 2/2010 |
| JP | 2010081981 A | 4/2010 |
| JP | 4640772 B2 | 12/2010 |
| JP | 2010536439 A | 12/2010 |
| JP | 2011500225 A | 1/2011 |
| JP | 2011030962 A | 2/2011 |
| JP | 4747166 B2 | 5/2011 |
| JP | 2011087823 A | 5/2011 |
| JP | 4801218 B1 | 8/2011 |
| JP | 2011218130 A | 11/2011 |
| JP | 2011224070 A | 11/2011 |
| JP | 3175719 U | 4/2012 |
| JP | 2012523869 A | 10/2012 |
| JP | 2013238608 A | 11/2013 |
| JP | 2014521960 A | 8/2014 |
| JP | 2015092945 A | 5/2015 |
| JP | 3198994 B2 | 7/2015 |
| JP | 2016521191 A | 7/2016 |
| JP | 2017014698 A | 1/2017 |
| JP | 2019076342 A | 5/2019 |
| JP | 2019525811 A | 9/2019 |
| JP | 2019170942 A | 10/2019 |
| JP | 2019533492 A | 11/2019 |
| JP | 2020520775 A | 7/2020 |
| JP | 2021120686 A | 8/2021 |
| JP | 2021522009 A | 8/2021 |
| JP | 2021522013 A | 8/2021 |
| JP | 7129493 B2 | 8/2022 |
| JP | 2023532132 A | 7/2023 |
| KR | 200290061 Y1 | 9/2002 |
| KR | 20030047451 A | 6/2003 |
| KR | 20140039485 A | 4/2014 |
| KR | 101432639 B1 | 8/2014 |
| KR | 20180106659 A | 10/2018 |
| KR | 20180108774 A | 10/2018 |
| PT | 2068717 E | 6/2013 |
| SE | 505542 C2 | 9/1997 |
| WO | 8101957 A1 | 7/1981 |
| WO | 8804558 A1 | 6/1988 |
| WO | 9104714 A2 | 4/1991 |
| WO | 9104714 A3 | 6/1991 |
| WO | 9220299 A1 | 2/1993 |
| WO | 9303690 A1 | 3/1993 |
| WO | 9307839 A1 | 4/1993 |
| WO | 9309736 A2 | 5/1993 |
| WO | 9309736 A3 | 6/1993 |
| WO | 9514448 A2 | 6/1995 |
| WO | 9600096 A1 | 1/1996 |
| WO | 9634636 A1 | 11/1996 |
| WO | 9817211 A1 | 4/1998 |
| WO | 9830336 A1 | 7/1998 |
| WO | 0000112 A1 | 1/2000 |
| WO | 0000113 A1 | 1/2000 |
| WO | 0025651 A1 | 5/2000 |
| WO | 0033773 A1 | 6/2000 |
| WO | 0057784 A1 | 10/2000 |
| WO | 0069377 A1 | 11/2000 |
| WO | 0079497 A1 | 12/2000 |
| WO | 0145618 A1 | 6/2001 |
| WO | 0145621 A1 | 6/2001 |
| WO | 02094160 A1 | 11/2002 |
| WO | 03013967 A1 | 2/2003 |
| WO | 03024824 A1 | 3/2003 |
| WO | 03055423 A1 | 7/2003 |
| WO | 03071931 A2 | 9/2003 |
| WO | 03079942 A1 | 10/2003 |
| WO | 03071931 A3 | 2/2004 |
| WO | 2004019836 A1 | 3/2004 |
| WO | 2004024046 A1 | 3/2004 |
| WO | 2004026195 A1 | 4/2004 |
| WO | 2005051252 A1 | 6/2005 |
| WO | 2005074571 A3 | 9/2005 |
| WO | 2005089687 A2 | 9/2005 |
| WO | 2005107661 A2 | 11/2005 |
| WO | 2006021220 A1 | 3/2006 |
| WO | 2006037140 A2 | 4/2006 |
| WO | 2007005851 A2 | 1/2007 |
| WO | 2007007845 A1 | 1/2007 |
| WO | 2007042823 A2 | 4/2007 |
| WO | 2007055651 A1 | 5/2007 |
| WO | 2006098950 A3 | 11/2007 |
| WO | 2007128156 A3 | 2/2008 |
| WO | 2008026106 A2 | 3/2008 |
| WO | 2008078117 A1 | 7/2008 |
| WO | 2008104019 A1 | 9/2008 |
| WO | 2008141471 A1 | 11/2008 |
| WO | 2009004368 A1 | 1/2009 |

(56) References Cited

FOREIGN PATENT DOCUMENTS

| | | |
|---|---|---|
| WO | 2009004369 A1 | 1/2009 |
| WO | 2009052496 A1 | 4/2009 |
| WO | 2009052502 A1 | 4/2009 |
| WO | 2009007702 A4 | 7/2009 |
| WO | 2009101738 A1 | 8/2009 |
| WO | 2010058192 A1 | 5/2010 |
| WO | 2010030122 A3 | 7/2010 |
| WO | 2010101915 A3 | 1/2011 |
| WO | 2011018132 A1 | 2/2011 |
| WO | 2011018133 A1 | 2/2011 |
| WO | 2011024864 A1 | 3/2011 |
| WO | 2011054118 A1 | 5/2011 |
| WO | 2011079132 A1 | 6/2011 |
| WO | 2011107972 A1 | 9/2011 |
| WO | 2011108972 A1 | 9/2011 |
| WO | 2011117292 A1 | 9/2011 |
| WO | 2011123219 A1 | 10/2011 |
| WO | 2011132043 A1 | 10/2011 |
| WO | 2012012908 A1 | 2/2012 |
| WO | 2012065274 A1 | 5/2012 |
| WO | 2012097462 A1 | 7/2012 |
| WO | 2012098796 A1 | 7/2012 |
| WO | 2012101288 A1 | 8/2012 |
| WO | 2012175916 A1 | 12/2012 |
| WO | 2013018435 A1 | 2/2013 |
| WO | 2013033429 A1 | 3/2013 |
| WO | 2013055434 A1 | 4/2013 |
| WO | 2013082397 A1 | 6/2013 |
| WO | 2013103291 A2 | 7/2013 |
| WO | 2013131109 A1 | 9/2013 |
| WO | 2013167478 A1 | 11/2013 |
| WO | 2013177716 A1 | 12/2013 |
| WO | 2014041534 A1 | 3/2014 |
| WO | 2014046420 A1 | 3/2014 |
| WO | 2014118518 A1 | 8/2014 |
| WO | 2014160852 A1 | 10/2014 |
| WO | 2015023599 A1 | 2/2015 |
| WO | 2015052348 A1 | 4/2015 |
| WO | 2015068384 A1 | 5/2015 |
| WO | 2015169403 A1 | 11/2015 |
| WO | 2015170307 A1 | 11/2015 |
| WO | 2015197462 A1 | 12/2015 |
| WO | 2016051385 A1 | 4/2016 |
| WO | 2016055989 A1 | 4/2016 |
| WO | 2016071894 A1 | 5/2016 |
| WO | 2016103242 A1 | 6/2016 |
| WO | 2016116915 A1 | 7/2016 |
| WO | 2016124203 A1 | 8/2016 |
| WO | 2016139448 A1 | 9/2016 |
| WO | 2016166562 A1 | 10/2016 |
| WO | 2016167535 A1 | 10/2016 |
| WO | 2016191574 A1 | 12/2016 |
| WO | 2016200088 A1 | 12/2016 |
| WO | 2016200361 A1 | 12/2016 |
| WO | 2016204731 A1 | 12/2016 |
| WO | 2017001532 A2 | 1/2017 |
| WO | 2017075226 A1 | 5/2017 |
| WO | 2017152198 A1 | 9/2017 |
| WO | 2017153357 A1 | 9/2017 |
| WO | 2017162559 A1 | 9/2017 |
| WO | 2017205446 A1 | 11/2017 |
| WO | 2017209779 A1 | 12/2017 |
| WO | 2017210524 A1 | 12/2017 |
| WO | 2018022414 A1 | 2/2018 |
| WO | 2018044781 A1 | 3/2018 |
| WO | 2018056953 A1 | 3/2018 |
| WO | 2018090550 A1 | 5/2018 |
| WO | 2018138513 A1 | 8/2018 |
| WO | 2018144318 A1 | 8/2018 |
| WO | 2018144463 A1 | 8/2018 |
| WO | 2018150263 A1 | 8/2018 |
| WO | 2018150268 A1 | 8/2018 |
| WO | 2018152156 A1 | 8/2018 |
| WO | 2018183791 A1 | 10/2018 |
| WO | 2018150267 A3 | 11/2018 |
| WO | 2018235026 A1 | 12/2018 |
| WO | 2018235065 A1 | 12/2018 |
| WO | 2019004404 A1 | 1/2019 |
| WO | 2019041005 A1 | 3/2019 |
| WO | 2019044217 A1 | 3/2019 |
| WO | 2019044218 A1 | 3/2019 |
| WO | 2019044219 A1 | 3/2019 |
| WO | 2019050959 A1 | 3/2019 |
| WO | 2019065541 A1 | 4/2019 |
| WO | 2019096845 A1 | 5/2019 |
| WO | 2019150385 A1 | 8/2019 |
| WO | 2019161094 A1 | 8/2019 |
| WO | 2019188566 A1 | 10/2019 |
| WO | 2019190593 A1 | 10/2019 |
| WO | 2019212949 A1 | 11/2019 |
| WO | 2019212950 A1 | 11/2019 |
| WO | 2019212951 A1 | 11/2019 |
| WO | 2019212952 A1 | 11/2019 |
| WO | 2019212954 A1 | 11/2019 |
| WO | 2019212955 A1 | 11/2019 |
| WO | 2019212956 A1 | 11/2019 |
| WO | 2019214787 A1 | 11/2019 |
| WO | 2019214788 A1 | 11/2019 |
| WO | 2019226826 A1 | 11/2019 |
| WO | 2019239433 A1 | 12/2019 |
| WO | 2020000994 A1 | 1/2020 |
| WO | 2020020618 A1 | 1/2020 |
| WO | 2020038822 A1 | 2/2020 |
| WO | 2020088409 A1 | 5/2020 |
| WO | 2020049394 A3 | 6/2020 |
| WO | 2020120657 A1 | 6/2020 |
| WO | 2020152575 A1 | 7/2020 |
| WO | 2020182923 A1 | 9/2020 |
| WO | 2020204967 A1 | 10/2020 |
| WO | 2020205939 A1 | 10/2020 |
| WO | 2020209898 A1 | 10/2020 |
| WO | 2020242790 A1 | 12/2020 |
| WO | 2020251893 A1 | 12/2020 |
| WO | 2020256865 A1 | 12/2020 |
| WO | 2021007144 A1 | 1/2021 |
| WO | 2021007345 A1 | 1/2021 |
| WO | 2021010844 A1 | 1/2021 |
| WO | 2021016026 A1 | 1/2021 |
| WO | 2021016300 A1 | 1/2021 |
| WO | 2021025919 A1 | 2/2021 |
| WO | 2021034886 A1 | 2/2021 |
| WO | 2021041123 A1 | 3/2021 |
| WO | 2021046501 A1 | 3/2021 |
| WO | 2021086868 A1 | 5/2021 |
| WO | 2021094352 A1 | 5/2021 |
| WO | 2021094639 A1 | 5/2021 |
| WO | 2021097067 A1 | 5/2021 |
| WO | 2021102296 A1 | 5/2021 |
| WO | 2021107025 A1 | 6/2021 |
| WO | 2021138411 A1 | 7/2021 |
| WO | 2021138414 A1 | 7/2021 |
| WO | 2021154686 A1 | 8/2021 |
| WO | 2021155206 A1 | 8/2021 |
| WO | 2021170075 A1 | 9/2021 |
| WO | 2021173436 A1 | 9/2021 |
| WO | 2021188817 A1 | 9/2021 |
| WO | 2021195384 A1 | 9/2021 |
| WO | 2021205995 A1 | 10/2021 |
| WO | 2021207621 A1 | 10/2021 |
| WO | 2021211568 A1 | 10/2021 |
| WO | 2021211801 A1 | 10/2021 |
| WO | 2021211914 A1 | 10/2021 |
| WO | 2021216419 A1 | 10/2021 |
| WO | 2021216422 A1 | 10/2021 |
| WO | 2021231532 A1 | 11/2021 |
| WO | 2021247523 A1 | 12/2021 |
| WO | 2021257202 A1 | 12/2021 |
| WO | 2022006256 A1 | 1/2022 |
| WO | 2022031943 A1 | 2/2022 |
| WO | 2022035745 A1 | 2/2022 |
| WO | 2022051360 A1 | 3/2022 |
| WO | 2022054613 A1 | 3/2022 |
| WO | 2022066704 A1 | 3/2022 |
| WO | 2022067392 A1 | 4/2022 |

(56) References Cited

FOREIGN PATENT DOCUMENTS

| | | | |
|---|---|---|---|
| WO | 2022069950 A1 | 4/2022 |
| WO | 2022071429 A1 | 4/2022 |
| WO | 2022076322 A1 | 4/2022 |
| WO | 2022076427 A2 | 4/2022 |
| WO | 2022086898 A1 | 4/2022 |
| WO | 2022090199 A1 | 5/2022 |
| WO | 2022098536 A1 | 5/2022 |
| WO | 2022099087 A1 | 5/2022 |
| WO | 2022101999 A1 | 5/2022 |
| WO | 2022115692 A1 | 6/2022 |
| WO | 2022125685 A1 | 6/2022 |
| WO | 2022140545 A1 | 6/2022 |
| WO | 2022145231 A1 | 7/2022 |
| WO | 2022150360 A1 | 7/2022 |
| WO | 2022150463 A1 | 7/2022 |
| WO | 2022159392 A1 | 7/2022 |
| WO | 2022170182 A1 | 8/2022 |
| WO | 2022182385 A1 | 9/2022 |
| WO | 2022187152 A1 | 9/2022 |
| WO | 2022192188 A1 | 9/2022 |
| WO | 2022192347 A1 | 9/2022 |
| WO | 2022204000 A1 | 9/2022 |
| WO | 2022216507 A1 | 10/2022 |
| WO | 2022216776 A1 | 10/2022 |
| WO | 2022222030 A1 | 10/2022 |
| WO | 2023286058 A1 | 1/2023 |
| WO | 2023014639 A1 | 2/2023 |
| WO | 2023014641 A1 | 2/2023 |
| WO | 2023018475 A2 | 2/2023 |
| WO | 2023023777 A1 | 3/2023 |
| WO | 2023034453 A1 | 3/2023 |
| WO | 2023038945 A1 | 3/2023 |
| WO | 2023038950 A1 | 3/2023 |
| WO | 2023049109 A1 | 3/2023 |
| WO | 2023049175 A1 | 3/2023 |
| WO | 2023086394 A1 | 5/2023 |
| WO | 2023149884 A1 | 8/2023 |
| WO | 2023149902 A1 | 8/2023 |
| WO | 2023149903 A1 | 8/2023 |
| WO | 2023154390 A1 | 8/2023 |
| WO | 2023191764 A1 | 10/2023 |
| WO | 2023244238 A1 | 12/2023 |
| WO | 2024058788 A1 | 3/2024 |

OTHER PUBLICATIONS

Advisory Action for U.S. Appl. No. 14/952,591 mailed Jun. 1, 2018.
Advisory Action for U.S. Appl. No. 15/238,427 mailed Apr. 10, 2019.
Advisory Action for U.S. Appl. No. 16/245,726 mailed Apr. 19, 2023.
Advisory Action for U.S. Appl. No. 16/369,676 mailed Mar. 24, 2023.
Advisory Action for U.S. Appl. No. 16/433,773 mailed Dec. 29, 2023.
Advisory Action for U.S. Appl. No. 16/433,773 mailed Feb. 15, 2023.
Advisory Action for U.S. Appl. No. 16/449,039 mailed Jan. 25, 2024.
Advisory Action for U.S. Appl. No. 16/452,258 mailed Oct. 26, 2022.
Advisory Action for U.S. Appl. No. 16/478,180 mailed Sep. 21, 2022.
Advisory Action for U.S. Appl. No. 16/478,180 mailed Sep. 7, 2023.
Advisory Action for U.S. Appl. No. 16/899,956 mailed Jul. 9, 2021.
Advisory Action for U.S. Appl. No. 16/904,868 mailed Jan. 2, 2024.
Advisory Action for U.S. Appl. No. 16/904,868 mailed Jul. 2, 2021.
Advisory Action for U.S. Appl. No. 16/904,868 mailed Jun. 15, 2022.
Advisory Action for U.S. Appl. No. 16/905,400 mailed Feb. 16, 2022.
Advisory Action for U.S. Appl. No. 16/905,400 mailed Jun. 9, 2021.
Advisory Action for U.S. Appl. No. 17/051,550 mailed Sep. 8, 2023.
Advisory Action for U.S. Appl. No. 17/051,585 mailed Oct. 17, 2023.
Advisory Action for U.S. Appl. No. 17/179,116 mailed Jan. 8, 2024.
Advisory Action for U.S. Appl. No. 17/444,792 mailed Aug. 25, 2023.
Advisory Action for U.S. Appl. No. 17/446,256 mailed Dec. 8, 2023.
Advisory Action for U.S. Appl. No. 17/448,811 mailed Nov. 15, 2023.
Advisory Action for U.S. Appl. No. 17/451,345 mailed Oct. 20, 2023.
Advisory Action for U.S. Appl. No. 17/453,260 mailed Dec. 22, 2023.
Advisory Action for U.S. Appl. No. 17/653,137 mailed Dec. 1, 2023.
Advisory Action for U.S. Appl. No. 17/655,464 mailed Dec. 13, 2023.
Advisory Action for U.S. Appl. No. 17/662,700 mailed Jan. 30, 2023.
Communication of Notice of Opposition of European Application No. 17807547.9 mailed Jan. 5, 2024.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Corrected Notice of Allowability for U.S. Appl. No. 16/369,676 mailed Dec. 7, 2023.
Corrected Notice of Allowability for U.S. Appl. No. 17/330,657 mailed Dec. 9, 2021.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/245,726 mailed Nov. 25, 2022.
Final Office Action for U.S. Appl. No. 16/369,676 mailed Aug. 31, 2023.
Final Office Action for U.S. Appl. No. 16/369,676 mailed Dec. 5, 2022.
Final Office Action for U.S. Appl. No. 16/433,773 mailed Oct. 10, 2023.
Final Office Action for U.S. Appl. No. 16/433,773 mailed Oct. 25, 2022.
Final Office Action for U.S. Appl. No. 16/449,039 mailed Aug. 1, 2022.
Final Office Action for U.S. Appl. No. 16/449,039 mailed Nov. 21, 2023.
Final Office Action for U.S. Appl. No. 16/452,145 mailed Mar. 25, 2022.
Final Office Action for U.S. Appl. No. 16/452,258 mailed Dec. 21, 2023.
Final Office Action for U.S. Appl. No. 16/452,258 mailed Jun. 14, 2022.

(56) References Cited

OTHER PUBLICATIONS

Final Office Action for U.S. Appl. No. 16/478,180 mailed Jun. 22, 2022.
Final Office Action for U.S. Appl. No. 16/478,180 mailed May 31, 2023.
Final Office Action for U.S. Appl. No. 16/899,956 mailed Apr. 19, 2021.
Final Office Action for U.S. Appl. No. 16/904,868 mailed Mar. 10, 2022.
Final Office Action for U.S. Appl. No. 16/904,868 mailed Mar. 26, 2021.
Final Office Action for U.S. Appl. No. 16/904,868 mailed Nov. 2, 2023.
Final Office Action for U.S. Appl. No. 16/905,400 mailed Apr. 6, 2021.
Final Office Action for U.S. Appl. No. 16/905,400 mailed Dec. 9, 2021.
Final Office Action for U.S. Appl. No. 17/051,399 mailed Jan. 8, 2024.
Final Office Action for U.S. Appl. No. 17/051,399 mailed Mar. 9, 2023.
Final Office Action for U.S. Appl. No. 17/051,550 mailed May 23, 2023.
Final Office Action for U.S. Appl. No. 17/051,585 mailed Jul. 27, 2023.
Final Office Action for U.S. Appl. No. 17/088,272 mailed May 25, 2021.
Final Office Action for U.S. Appl. No. 17/179,116 mailed Oct. 31, 2023.
Final Office Action for U.S. Appl. No. 17/444,792 mailed Jun. 15, 2023.
Final Office Action for U.S. Appl. No. 17/446,256 mailed Sep. 19, 2023.
Final Office Action for U.S. Appl. No. 17/448,811 mailed Aug. 3, 2023.
Final Office Action for U.S. Appl. No. 17/450,864 mailed Dec. 28, 2023.
Final Office Action for U.S. Appl. No. 17/451,345 mailed May 3, 2023.
Final Office Action for U.S. Appl. No. 17/451,354 mailed Oct. 30, 2023.
Final Office Action for U.S. Appl. No. 17/453,260 mailed Oct. 5, 2023.
Final Office Action for U.S. Appl. No. 17/501,591 mailed Nov. 14, 2023.
Final Office Action for U.S. Appl. No. 17/646,771 mailed Dec. 21, 2023.
Final Office Action for U.S. Appl. No. 17/653,137 mailed Sep. 21, 2023.
Final Office Action for U.S. Appl. No. 17/655,464 mailed Sep. 1, 2023.
Final Office Action for U.S. Appl. No. 17/661,090 mailed Dec. 11, 2023.
Final Office Action for U.S. Appl. No. 17/662,700 mailed Sep. 30, 2022.
Final Office Action for U.S. Appl. No. 17/663,330 mailed Dec. 12, 2023.
Final Office Action for U.S. Appl. No. 17/664,487 mailed Jan. 4, 2024.
Final Office Action for U.S. Appl. No. 18/139,523 mailed Dec. 22, 2023.
Final Office Action for U.S. Appl. No. 18/140,751 mailed Jan. 17, 2024.
Final Office Action for U.S. Appl. No. 18/164,800 mailed Dec. 6, 2023.
Final Office Action for U.S. Appl. No. 29/624,661 mailed Feb. 18, 2020.
International Search Report and Written Opinion from International Application No. PCT/IB2021/057173 mailed Nov. 5, 2021.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/057562 mailed Jan. 27, 2021.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/024162 mailed Jul. 8, 2021.
International Search Report and Written Opinion from International Application No. PCT/US2021/026607 mailed Jul. 29, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.

(56) References Cited

OTHER PUBLICATIONS

International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/039866 mailed Oct. 7, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
International Search Report and Written Opinion from International Application No. PCT/US2021/048661 mailed Feb. 14, 2022.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/055515 mailed Jan. 28, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.
International Search Report and Written Opinion from International Application No. PCT/US2021/062440 mailed Mar. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.
International Search Report and Written Opinion from International Application No. PCT/US2022/012794 mailed May 3, 2022.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
International Search Report and Written Opinion from International Application No. PCT/US2022/015418 mailed Nov. 11, 2022.
International Search Report and Written Opinion from International Application No. PCT/US2022/015420 mailed Nov. 18, 2022.
International Search Report and Written Opinion from International Application No. PCT/US2022/015471 mailed May 16, 2022.
International Search Report and Written Opinion from International Application No. PCT/US2022/015492 mailed Apr. 26, 2022.
International Search Report and Written Opinion from International Application No. PCT/US2022/015781 mailed May 6, 2022.
International Search Report and Written Opinion from International Application No. PCT/US2022/016942 mailed Jun. 8, 2022.
International Search Report and Written Opinion from International Application No. PCT/US2022/018159 mailed Dec. 12, 2022.
International Search Report and Written Opinion from International Application No. PCT/US2022/018170 mailed May 31, 2022.
International Search Report and Written Opinion from International Application No. PCT/US2022/019254 mailed Jun. 7, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.
International Search Report and Written Opinion from International Application No. PCT/US2022/022111 mailed Oct. 26, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
International Search Report and Written Opinion from International Application No. PCT/US2022/039018 mailed Jan. 10, 2023.
International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/039714 mailed Nov. 22, 2022.
International Search Report and Written Opinion from International Application No. PCT/US2022/041085 mailed Mar. 16, 2023.
International Search Report and Written Opinion from International Application No. PCT/US2022/041688 mailed Nov. 21, 2022.
International Search Report and Written Opinion from International Application No. PCT/US2022/042719 mailed Dec. 5, 2022.
International Search Report and Written Opinion from International Application No. PCT/US2022/042725 mailed Dec. 19, 2022.
International Search Report and Written Opinion from International Application No. PCT/US2022/043818 mailed Mar. 24, 2023.
International Search Report and Written Opinion from International Application No. PCT/US2022/044107 mailed Dec. 23, 2022.
International Search Report and Written Opinion from International Application No. PCT/US2022/044208 mailed May 8, 2023.
International Search Report and Written Opinion from International Application No. PCT/US2022/044212 mailed Jan. 20, 2023.
International Search Report and Written Opinion from International Application No. PCT/US2022/044243 mailed Feb. 24, 2023.
International Search Report and Written Opinion from International Application No. PCT/US2022/049300 mailed Jun. 6, 2023.
International Search Report and Written Opinion from International Application No. PCT/US2022/050909 mailed Jul. 24, 2023.
International Search Report and Written Opinion from International Application No. PCT/US2023/012696 mailed Jul. 6, 2023.
International Search Report and Written Opinion from International Application No. PCT/US2023/018474 mailed Sep. 11, 2023.
International Search Report and Written Opinion from International Application No. PCT/US2023/024805 mailed Dec. 14, 2023.
Issue Notification for U.S. Appl. No. 14/952,591 mailed Jul. 28, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.

(56) References Cited

OTHER PUBLICATIONS

Issue Notification for U.S. Appl. No. 15/611,587 mailed Feb. 20, 2019.
Issue Notification for U.S. Appl. No. 15/612,325 mailed Mar. 24, 2021.
Issue Notification for U.S. Appl. No. 16/245,726 mailed Oct. 18, 2023.
Issue Notification for U.S. Appl. No. 16/899,956 mailed Mar. 29, 2023.
Issue Notification for U.S. Appl. No. 16/905,400 mailed Nov. 30, 2022.
Issue Notification for U.S. Appl. No. 17/088,272 mailed Jun. 15, 2022.
Issue Notification for U.S. Appl. No. 17/330,657 mailed Jun. 22, 2022.
Issue Notification for U.S. Appl. No. 17/461,036 mailed Oct. 11, 2023.
Issue Notification for U.S. Appl. No. 17/663,046 mailed Dec. 20, 2023.
Issue Notification for U.S. Appl. No. 29/624,661 mailed Aug. 4, 2021.
Non-Final Office Action for U.S. Appl. No. 14/947,759 mailed Mar. 17, 2016.
Non-Final Office Action for U.S. Appl. No. 14/952,591 mailed Aug. 1, 2017.
Non-Final Office Action for U.S. Appl. No. 14/952,591 mailed Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.
Non-Final Office Action for U.S. Appl. No. 15/171,968 mailed May 11, 2020.
Non-Final Office Action for U.S. Appl. No. 15/171,968 mailed Aug. 20, 2019.
Non-Final Office Action for U.S. Appl. No. 15/171,968 mailed Jun. 12, 2018.
Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.
Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.
Non-Final Office Action for U.S. Appl. No. 16/245,726 mailed Jan. 21, 2022.
Non-Final Office Action for U.S. Appl. No. 16/369,676 mailed Mar. 31, 2022.
Non-Final Office Action for U.S. Appl. No. 16/433,773 mailed Apr. 11, 2023.
Non-Final Office Action for U.S. Appl. No. 16/433,773 mailed Apr. 21, 2022.
Non-Final Office Action for U.S. Appl. No. 16/449,039 mailed Apr. 27, 2023.
Non-Final Office Action for U.S. Appl. No. 16/449,039 mailed Dec. 8, 2021.
Non-Final Office Action for U.S. Appl. No. 16/452,145 mailed Mar. 28, 2023.
Non-Final Office Action for U.S. Appl. No. 16/452,145 mailed Nov. 2, 2023.
Non-Final Office Action for U.S. Appl. No. 16/452,145 mailed Sep. 28, 2021.
Non-Final Office Action for U.S. Appl. No. 16/452,258 mailed Apr. 26, 2023.
Non-Final Office Action for U.S. Appl. No. 16/452,258 mailed Sep. 28, 2021.
Non-Final Office Action for U.S. Appl. No. 16/478,180 mailed Dec. 20, 2022.
Non-Final Office Action for U.S. Appl. No. 16/478,180 mailed Nov. 7, 2023.
Non-Final Office Action for U.S. Appl. No. 16/478,180 mailed Oct. 22, 2021.
Non-Final Office Action for U.S. Appl. No. 16/899,956 mailed Oct. 16, 2020.
Non-Final Office Action for U.S. Appl. No. 16/899,956 mailed Sep. 2, 2021.
Non-Final Office Action for U.S. Appl. No. 16/904,868 mailed Mar. 15, 2023.
Non-Final Office Action for U.S. Appl. No. 16/904,868 mailed Nov. 25, 2020.
Non-Final Office Action for U.S. Appl. No. 16/904,868 mailed Oct. 5, 2021.
Non-Final Office Action for U.S. Appl. No. 16/905,400 mailed Apr. 27, 2022.
Non-Final Office Action for U.S. Appl. No. 16/905,400 mailed Dec. 2, 2020.
Non-Final Office Action for U.S. Appl. No. 16/905,400 mailed Jul. 22, 2021.
Non-Final Office Action for U.S. Appl. No. 17/051,399 mailed Aug. 18, 2023.
Non-Final Office Action for U.S. Appl. No. 17/051,550 mailed Dec. 15, 2022.
Non-Final Office Action for U.S. Appl. No. 17/051,550 mailed Oct. 24, 2023.
Non-Final Office Action for U.S. Appl. No. 17/051,585 mailed Jan. 8, 2024.
Non-Final Office Action for U.S. Appl. No. 17/051,585 mailed Mar. 29, 2023.
Non-Final Office Action for U.S. Appl. No. 17/051,600 mailed Jan. 17, 2024.
Non-Final Office Action for U.S. Appl. No. 17/088,272 mailed Jan. 25, 2021.
Non-Final Office Action for U.S. Appl. No. 17/179,116 mailed Mar. 24, 2023.
Non-Final Office Action for U.S. Appl. No. 17/326,980 mailed Jul. 11, 2023.
Non-Final Office Action for U.S. Appl. No. 17/330,657 mailed Aug. 11, 2021.
Non-Final Office Action for U.S. Appl. No. 17/444,792 mailed Feb. 10, 2023.
Non-Final Office Action for U.S. Appl. No. 17/444,792 mailed Nov. 17, 2023.
Non-Final Office Action for U.S. Appl. No. 17/446,256 mailed Apr. 13, 2023.
Non-Final Office Action for U.S. Appl. No. 17/446,654 mailed Sep. 8, 2023.
Non-Final Office Action for U.S. Appl. No. 17/447,123 mailed Jan. 24, 2024.
Non-Final Office Action for U.S. Appl. No. 17/448,811 mailed Jan. 17, 2024.
Non-Final Office Action for U.S. Appl. No. 17/448,811 mailed Mar. 1, 2023.
Non-Final Office Action for U.S. Appl. No. 17/450,864 mailed May 10, 2023.
Non-Final Office Action for U.S. Appl. No. 17/451,345 mailed Dec. 7, 2022.
Non-Final Office Action for U.S. Appl. No. 17/451,345 mailed Jan. 17, 2024.
Non-Final Office Action for U.S. Appl. No. 17/451,354 mailed May 3, 2023.
Non-Final Office Action for U.S. Appl. No. 17/453,260 mailed Mar. 14, 2023.
Non-Final Office Action for U.S. Appl. No. 17/453,560 mailed Oct. 16, 2023.
Non-Final Office Action for U.S. Appl. No. 17/501,591 mailed Apr. 25, 2023.

(56) References Cited

OTHER PUBLICATIONS

Non-Final Office Action for U.S. Appl. No. 17/645,821 mailed Oct. 25, 2023.
Non-Final Office Action for U.S. Appl. No. 17/646,771 mailed Jul. 5, 2023.
Non-Final Office Action for U.S. Appl. No. 17/653,137 mailed Apr. 7, 2023.
Non-Final Office Action for U.S. Appl. No. 17/653,137 mailed Jan. 18, 2024.
Non-Final Office Action for U.S. Appl. No. 17/655,464 mailed Mar. 14, 2023.
Non-Final Office Action for U.S. Appl. No. 17/657,474 mailed Sep. 12, 2023.
Non-Final Office Action for U.S. Appl. No. 17/661,090 mailed Jul. 6, 2023.
Non-Final Office Action for U.S. Appl. No. 17/662,700 mailed Jul. 22, 2022.
Non-Final Office Action for U.S. Appl. No. 17/663,330 mailed Jun. 29, 2023.
Non-Final Office Action for U.S. Appl. No. 17/664,487 mailed Jun. 8, 2023.
Non-Final Office Action for U.S. Appl. No. 17/808,354 mailed Nov. 28, 2023.
Non-Final Office Action for U.S. Appl. No. 18/134,857 mailed Jan. 25, 2024.
Non-Final Office Action for U.S. Appl. No. 18/139,523 mailed Aug. 17, 2023.
Non-Final Office Action for U.S. Appl. No. 18/140,163 mailed Nov. 9, 2023.
Non-Final Office Action for U.S. Appl. No. 18/140,751 mailed Sep. 14, 2023.
Non-Final Office Action for U.S. Appl. No. 18/198,464 mailed Dec. 7, 2023.
Non-Final Office Action for U.S. Appl. No. 29/624,661 mailed Jul. 18, 2019.
Non-Final Office Action for U.S. Appl. No. 29/694,002 mailed Jun. 24, 2020.
Non-Final Office Action for U.S. Appl. No. 29/741,751 mailed Jan. 18, 2022.
Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019.
Notice of Allowance for U.S. Appl. No. 15/238,427 mailed May 23, 2019.
Notice of Allowance for U.S. Appl. No. 15/260,103 mailed Jun. 7, 2019.
Notice of Allowance for U.S. Appl. No. 15/611,587 mailed Dec. 21, 2018.
Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 16/245,726 mailed Jul. 6, 2023.
Notice of Allowance for U.S. Appl. No. 16/369,676 mailed Nov. 14, 2023.
Notice of Allowance for U.S. Appl. No. 16/449,039 mailed Dec. 15, 2022.
Notice of Allowance for U.S. Appl. No. 16/899,956 mailed Apr. 19, 2022.
Notice of Allowance for U.S. Appl. No. 16/899,956 mailed Aug. 10, 2022.
Notice of Allowance for U.S. Appl. No. 16/899,956 mailed Dec. 1, 2022.
Notice of Allowance for U.S. Appl. No. 16/899,956 mailed Dec. 29, 2021.
Notice of Allowance for U.S. Appl. No. 16/905,400 mailed Aug. 17, 2022.
Notice of Allowance for U.S. Appl. No. 17/051,554 mailed Jul. 6, 2023.
Notice of Allowance for U.S. Appl. No. 17/051,554 mailed Oct. 18, 2023.
Notice of Allowance for U.S. Appl. No. 17/088,272 mailed Aug. 5, 2021.
Notice of Allowance for U.S. Appl. No. 17/088,272 mailed Mar. 4, 2022.
Notice of Allowance for U.S. Appl. No. 17/088,272 mailed Nov. 24, 2021.
Notice of Allowance for U.S. Appl. No. 17/326,980 mailed Jan. 29, 2024.
Notice of Allowance for U.S. Appl. No. 17/330,657 mailed Mar. 16, 2022.
Notice of Allowance for U.S. Appl. No. 17/330,657 mailed Nov. 26, 2021.
Notice of Allowance for U.S. Appl. No. 17/461,036 mailed Feb. 22, 2023.
Notice of Allowance for U.S. Appl. No. 17/461,036 mailed Jun. 30, 2023.
Notice of Allowance for U.S. Appl. No. 17/461,036 mailed Oct. 6, 2022.
Notice of Allowance for U.S. Appl. No. 17/662,700 mailed Jul. 28, 2023.
Notice of Allowance for U.S. Appl. No. 17/662,700 mailed Mar. 28, 2023.
Notice of Allowance for U.S. Appl. No. 17/662,700 mailed Nov. 15, 2023.
Notice of Allowance for U.S. Appl. No. 17/663,046 mailed Jan. 30, 2023.
Notice of Allowance for U.S. Appl. No. 18/299,788 mailed Jul. 24, 2023.
Notice of Allowance for U.S. Appl. No. 18/299,788 mailed Nov. 6, 2023.
Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice of Allowance for U.S. Appl. No. 29/741,751 mailed Jun. 9, 2022.
Notice to File Missing Parts for U.S. Appl. No. 17/179,116 mailed Mar. 3, 2021.
Restriction Requirement for U.S. Appl. No. 16/433,773 mailed Dec. 7, 2021.
Restriction Requirement for U.S. Appl. No. 16/478,180 mailed May 25, 2021.
Restriction Requirement for U.S. Appl. No. 17/051,600 mailed Sep. 21, 2023.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/645,821 mailed Jul. 12, 2023.
Restriction Requirement for U.S. Appl. No. 17/646,771 mailed Apr. 6, 2023.

(56) References Cited

OTHER PUBLICATIONS

Restriction Requirement for U.S. Appl. No. 17/657,474 mailed Jun. 30, 2023.
Restriction Requirement for U.S. Appl. No. 18/134,857 mailed Oct. 23, 2023.
Submission in Opposition Proceedings for European Application No. 17807547.9 filed Jan. 10, 2024.
Text Messages to Lorena Eckert Re Prototype PureWick Holder dated Apr. 16, 2022.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 15/384,196, filed Dec. 19, 2016.
U.S. Appl. No. 15/611,587, filed Jun. 1, 2017.
U.S. Appl. No. 15/612,325, filed Jun. 2, 2017.
U.S. Appl. No. 16/245,726, filed Jan. 11, 2019.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/394,055, filed Aug. 4, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/451,719, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,487, filed May 23, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/299,788, filed Apr. 13, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/389,009, filed Nov. 13, 2023.
U.S. Appl. No. 18/415,080, filed Jan. 17, 2024.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 29/741,751, filed Jul. 15, 2020.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/452,437, filed Jan. 31, 2017.
U.S. Appl. No. 62/485,578, filed Apr. 14, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.

(56) References Cited

OTHER PUBLICATIONS

U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,158, filed Jan. 26, 2020.
U.S. Appl. No. 62/967,977, filed Jan. 30, 2020.
U.S. Appl. No. 62/991,754, filed Mar. 19, 2020.
U.S. Appl. No. 62/994,912, filed Mar. 26, 2020.
U.S. Appl. No. 63/008,112, filed Apr. 10, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/094,646, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/138,878, filed Jan. 19, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/150,640, filed Feb. 18, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/191,558, filed May 21, 2021.
U.S. Appl. No. 63/192,274, filed May 24, 2021.
U.S. Appl. No. 63/192,289, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/208,262, filed Jun. 8, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/230,897, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,328, filed Sep. 7, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
U.S. Appl. No. 63/308,190, filed Feb. 9, 2022.
U.S. Appl. No. 63/596,012, filed Nov. 3, 2023.
U.S. Appl. No. 63/608,553, filed Dec. 11, 2023.
Defendant and Counterclaim Plaintiff Sage Products, LLC's Answer, Defenses, and Counterclaims to Plaintiff's Amended Complaint, Nov. 1, 2019.
*PureWick Corporation v. Sage Products, LLC* Transcripts vol. 2, Mar. 29, 2022.
*PureWick Corporation v. Sage Products, LLC* Transcripts vol. 3, Mar. 30, 2022.
*PureWick Corporation v. Sage Products, LLC* Transcripts vol. 4, Mar. 31, 2022.
Memorandum Order, Feb. 2021.
Sage's Initial Invalidity Contentions Regarding U.S. Pat. Nos. 8,287,508; 10,226,375; and 10,390,989, May 29, 2020.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020.
Sage's Second Supplemental Invalidity Contentions Regarding U.S. Pat. Nos. 8,287,508, 10,226,375, 10,390,989, and 10,376,407.
Boehringer CareDry System—Second Generation for Non-Invasive Urinary Management for Females, Mar. 2021.
*PureWick Corporation v. Sage Products, LLC* Transcripts vol. 5, Apr. 1, 2022.
Excerpts from the 508 (U.S. Pat. No. 8,278,508) Patent's Prosecution History, 2020.
*PureWick Corporation v. Sage Products, LLC* Transcripts vol. 1, Mar. 28, 2022.
Plaintiff's Opening Claim Construction Brief, Oct. 16, 2020.
Plaintiff's Identification of Claim Terms and Proposed Constructions.
PureWick's Response to Interrogatory No. 9 in *PureWick, LLC* v. *Sage Products, LLC*, Mar. 23, 2020.
Sage's Preliminary Identification of Claim Elements and Proposed Constructions for U.S. Pat. Nos. 8,287,508, 10,226,376, 10,390,989 and 10,376,407.
Decision Granting Institution of Inter Partes Review for U.S. Pat. No. 8,287,508, Feb. 17, 2021.
Corrected Certificate of Service , 2020.
Declaration of Diane K. Newman Curriculum Vitae , 2020.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.

(56) References Cited

OTHER PUBLICATIONS

"AMXD Control Starter Kit", Omni Medical Systems, Inc., 1 page.
"AMXD Control Starter Kit Brochure", https://www.omnimedicalsys.com/index.php?page=products, 8 pages.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"AMXDmax In-Flight Bladder Relief", Omni Medical; Omni Medical Systems, Inc., 2015.
"AMXDX—Advanced Mission Extender Device Brochure", Omni Medical, 2 pages.
"Combat Force Multiplier in Flight Bladder Relief Cockpit Essential Equipment Brochure", Omni Medical, 20 pages.
"External Urine Management for Female Anatomy", https://www.stryker.com/US/en/sage/products/sage-primafit.html, Jul. 2020, 4 pages.
"GSA Price List", Omni Medical, Apr. 2011, 2 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, 14 pages.
"Letter to Mark Harvie of Omni Measurement Systems", Department of Veterans Affairs, Nov. 1, 2007, 11 pages.
"Making Women's Sanitary Products Safer and Cheaper", https://www.elsevier.com/connect/making-womens-sanitary-products-safer-and-cheaper , Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Revised AMXDmax Advanced Mission Extender Device User & Maintenance Guide", Omni Medical Systems, Oct. 8, 2019, 52 pages.
"Rising Warrior Insulated Gallon Jug Cover", https://www.amazon.com/Rising-Warrior-Insulated-Sleeve, 2021, 2 pages.
"Step by Step How Ur24 WorksHome", http://medicalpatentur24.com, Aug. 30, 2017, 4 pages.
"Underwear that absorbs your period", Thinx!, 7 pages.
"Urine Bag Cover—Catheter Bag Cover 2000 ml Volume—Medline Style—Multiple Sclerosis—Spine Injury—Suprapublic Catheter—Bladder Incontinence", https://www.etsy.com/listing/1142934658/urine-bag-cover-caatheter-bag-cover-2000, 2022, 1 page.
"User & Maintenance Guide", Omni Medical , 2007, 16 pages.
"Vinyl Dust Cover, Janome #741811000, Janome, Sewing Parts Online", https://www.sewingpartsonline.com/vinyl-dust-cover-janome-74181000, 2020, 2 pages.
"Winners Announced for Dare-to-Dream Medtech Design Challenge", https://www.mddionline.com/design-engineering/winners-announced-dare-dream-medtech-design-challenge, 2014, 4 pages.
Ali, "Sustainability Assessment: Seventh Generation Diapers versus gDiapers", The University of Vermont, Dec. 6, 2011, pp. 1-31.
Autumn, et al., "Frictional adhesion: a new angle on gecko attachment", The Journal of Experimental Biology, 2006, pp. 3569-3579.
Cañas, et al., "Effect of nano- and micro-roughness on adhesion of bioinspired micropatterned surfaces", Acta Biomaterialia 8, 2012, pp. 282-288.

Chaudhary, et al., "Bioinspired dry adhesive: Poly(dimethylsiloxane) grafted with poly(2-ethylhexyl acrylate) brushes", European Polymer Journal, 2015, pp. 432-440.
Dai, et al., "Non-sticky and Non-slippery Biomimetic Patterned Surfaces", Journal of Bionic Engineering, Mar. 2020, pp. 326-334.
Espinoza-Ramirez , "Nanobiodiversity and Biomimetic Adhesives Development: From Nature to Production and Application", Journal of Biomaterials and Nanobiotechnology, pp. 78-101, 2019.
Hollister, "Female Urinary and Pouch and Male Urinary Pouch Brochure", www.hollister.com, 2011, 1 page.
Hollister, "Male Urinary Pouch External Collection Device", http://www.hollister.com/en/products/Continence-Care-Products/Urine-Collectors/Urine-Collection-Accessories/Male-Urinary-Pouch-External-Collection-Device.
Hollister, Retracted Penis Pouch by Hollister , Vitality Medical.com.
Hwang, et al., "Multifunctional Smart Skin Adhesive Patches for Advanced Health Care", Adv. Healthcare Mater, 2018, pp. 1-20.
Jagota, et al., "Adhesion, friction, and compliance of bio-mimetic and bio-inspired structured interfaces", Materials Science and Engineering, 2011, pp. 253-292.
Jeong, et al., "A nontransferring dry adhesive with hierarchical polymer nanohairs", PNAS, Apr. 7, 2009, pp. 5639-5644.
Jeong, et al., "Nanohairs and nanotubes: Efficient structural elements for gecko-inspired artificial dry adhesives", Science Direct, 2009, pp. 335-346.
Karp, et al., "Dry solution to a sticky problem", Nature., 2011, pp. 42-43.
Lee, et al., "Continuous Fabrication of Wide-Tip Microstructures for Bio-Inspired Dry Adhesives via Tip Inking Process", Journal of Chemistry, Jan. 2, 2019, pp. 1-5.
Macaulay, et al., "A Noninvasive Continence Management System: Development and Evaluation of a Novel Toileting Device for Women", The Wound, Ostomy and Continence Nurses Society, 2007, pp. 641-648.
Merriam-Webster Dictionary, "Embed Definition & Meaning", https://www.merriam-webster.com/dictionary/embed last accessed Aug. 3, 2023, 2003.
Newman, et al., "The Urinary Incontinence Sourcebook", Petition for Interparties Review, 1997, 23 pages.
Newton, et al., "Measuring Safety, Effectiveness and Ease of Use of PureWick in the Management of Urinary Incontinence in Bedbound Women: Case Studies", 11 pages.
Parmar, "10 Finalists Chosen for Dare-to-Dream Medtech Design Challenge (PureWick)", Design Services, Nov. 10, 2014, 3 pages.
Parness, et al., "A microfabricated wedge-shaped adhesive array displaying gecko-like dynamic adhesion, directionality", J.R. Soc. Interface, 2009, pp. 1223-1232.
Pieper, et al., "An external urine-collection device for women: A clinical trial", Journal of ER Nursing, vol. 20, No. 2, Mar./Apr. 1993, pp. 51-55.
PureWick , "Incontinence Relief for Women", Presentation, Sep. 23, 2015, 7 pages.
Pytlik, "Super Absorbent Polymers", University of Buffalo.
Sachtman, "New Relief for Pilots? It Depends", Wired , 2008, 2 pages.
Tsipenyuk, et al., "Use of biomimetic hexagonal surface texture in friction against lubricated skin", Journal of The Royal Society—Interface, 2014, pp. 1-6.
Vinas, "A Solution for an Awkward—but Serious—Subject", http://www.aero-news.net/index.cfm?do=main.textpost&id=69ae2bb1-838b-4098-a7b5-7flbb2505688 last accessed Feb. 8, 2021.
Wikipedia Article, "Zylinder (Geometrie)", https://de.wikipedia.org/w/index.php?title=Zylinder (Geometrie)&oldid=154862081, version of Jun. 1, 2016, 7 pages.
Advisory Action for U.S. Appl. No. 16/452,258 mailed Apr. 8, 2024.
Advisory Action for U.S. Appl. No. 16/478,180 mailed Jun. 7, 2024.
Advisory Action for U.S. Appl. No. 17/051,585 mailed Oct. 8, 2024.
Advisory Action for U.S. Appl. No. 17/444,792 mailed Jul. 8, 2024.
Advisory Action for U.S. Appl. No. 17/446,654 mailed Apr. 15, 2024.
Advisory Action for U.S. Appl. No. 17/450,864 mailed Mar. 21, 2024.

(56) References Cited

OTHER PUBLICATIONS

Advisory Action for U.S. Appl. No. 17/451,345 mailed Jul. 3, 2024.
Advisory Action for U.S. Appl. No. 17/451,354 mailed Jan. 30, 2024.
Advisory Action for U.S. Appl. No. 17/501,591 mailed Feb. 22, 2024.
Advisory Action for U.S. Appl. No. 17/645,821 mailed Jul. 2, 2024.
Advisory Action for U.S. Appl. No. 17/646,771 mailed Feb. 29, 2024.
Advisory Action for U.S. Appl. No. 17/653,920 mailed Oct. 28, 2024.
Advisory Action for U.S. Appl. No. 17/661,090 mailed Feb. 26, 2024.
Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 17/808,354 mailed Jun. 12, 2024.
Advisory Action for U.S. Appl. No. 18/134,857 mailed Oct. 23, 2024.
Advisory Action for U.S. Appl. No. 18/139,523 mailed Apr. 24, 2024.
Advisory Action for U.S. Appl. No. 18/140,163 mailed Jun. 3, 2024.
Advisory Action for U.S. Appl. No. 18/140,751 mailed Apr. 24, 2024.
Advisory Action for U.S. Appl. No. 18/164,800 mailed Feb. 12, 2024.
Corrected Notice of Allowability for U.S. Appl. No. 17/326,980 mailed Feb. 8, 2024.
Corrected Notice of Allowability for U.S. Appl. No. 17/450,864 mailed Oct. 24, 2024.
Corrected Notice of Allowability for U.S. Appl. No. 17/501,591 mailed Aug. 9, 2024.
Corrected Notice of Allowability for U.S. Appl. No. 17/657,474 mailed Mar. 13, 2024.
Corrected Notice of Allowability for U.S. Appl. No. 17/657,474 mailed May 14, 2024.
Corrected Notice of Allowability for U.S. Appl. No. 17/664,914 mailed Aug. 9, 2024.
Final Office Action for U.S. Appl. No. 16/433,773 mailed Sep. 9, 2024.
Final Office Action for U.S. Appl. No. 16/478,180 mailed Feb. 28, 2024.
Final Office Action for U.S. Appl. No. 17/051,585 mailed Jul. 5, 2024.
Final Office Action for U.S. Appl. No. 17/051,600 mailed Jun. 27, 2024.
Final Office Action for U.S. Appl. No. 17/444,792 mailed Apr. 3, 2024.
Final Office Action for U.S. Appl. No. 17/446,256 mailed Aug. 7, 2024.
Final Office Action for U.S. Appl. No. 17/446,654 mailed Jan. 31, 2024.
Final Office Action for U.S. Appl. No. 17/447,123 mailed May 14, 2024.
Final Office Action for U.S. Appl. No. 17/451,345 mailed Apr. 18, 2024.
Final Office Action for U.S. Appl. No. 17/451,354 mailed Oct. 28, 2024.
Final Office Action for U.S. Appl. No. 17/597,673 mailed Oct. 22, 2024.
Final Office Action for U.S. Appl. No. 17/645,821 mailed Apr. 3, 2024.
Final Office Action for U.S. Appl. No. 17/653,137 mailed Aug. 7, 2024.
Final Office Action for U.S. Appl. No. 17/653,920 mailed Aug. 14, 2024.
Final Office Action for U.S. Appl. No. 17/808,354 mailed Apr. 10, 2024.
Final Office Action for U.S. Appl. No. 18/003,029 mailed Oct. 22, 2024.
Final Office Action for U.S. Appl. No. 18/134,857 mailed Jul. 25, 2024.
Final Office Action for U.S. Appl. No. 18/140,163 mailed Mar. 27, 2024.
Final Office Action for U.S. Appl. No. 18/164,800 mailed Oct. 22, 2024.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/030365 mailed Mar. 13, 2024.
International Search Report and Written Opinion from International Application No. PCT/US2023/030373 mailed Mar. 13, 2024.
International Search Report and Written Opinion from International Application No. PCT/US2023/031433 mailed Mar. 4, 2024.
International Search Report and Written Opinion from International Application No. PCT/US2023/031740 mailed Mar. 4, 2024.
International Search Report and Written Opinion from International Application No. PCT/US2023/036238 mailed Jul. 22, 2024.
International Search Report and Written Opinion from International Application No. PCT/US2023/036868 mailed Jun. 5, 2024.
International Search Report and Written Opinion from International Application No. PCT/US2023/075507 mailed Jun. 13, 2024.
International Search Report and Written Opinion from International Application No. PCT/US2023/077168 mailed Jun. 24, 2024.
International Search Report and Written Opinion from International Application No. PCT/US2023/077208 mailed May 10, 2024.
International Search Report and Written Opinion from International Application No. PCT/US2023/080680 mailed Jul. 22, 2024.
International Search Report and Written Opinion from International Application No. PCT/US2023/085516 mailed Aug. 26, 2024.
Issue Notification for U.S. Appl. No. 16/369,676 mailed Oct. 2, 2024.
Issue Notification for U.S. Appl. No. 16/449,039 mailed Jun. 19, 2024.
Issue Notification for U.S. Appl. No. 16/452,145 mailed Oct. 23, 2024.
Issue Notification for U.S. Appl. No. 17/051,550 mailed Mar. 13, 2024.
Issue Notification for U.S. Appl. No. 17/051,554 mailed Mar. 6, 2024.
Issue Notification for U.S. Appl. No. 17/326,980 mailed Jul. 10, 2024.
Issue Notification for U.S. Appl. No. 17/448,811 mailed Jul. 3, 2024.
Issue Notification for U.S. Appl. No. 17/453,260 mailed Jul. 10, 2024.
Issue Notification for U.S. Appl. No. 17/453,560 mailed Aug. 7, 2024.
Issue Notification for U.S. Appl. No. 17/657,474 mailed Jun. 19, 2024.
Issue Notification for U.S. Appl. No. 17/662,700 mailed Oct. 23, 2024.
Issue Notification for U.S. Appl. No. 18/299,788 mailed Feb. 21, 2024.
Non-Final Office Action for U.S. Appl. No. 16/369,676 mailed Feb. 29, 2024.
Non-Final Office Action for U.S. Appl. No. 16/433,773 mailed Feb. 26, 2024.
Non-Final Office Action for U.S. Appl. No. 16/452,258 mailed Jun. 20, 2024.
Non-Final Office Action for U.S. Appl. No. 16/478,180 mailed Aug. 7, 2024.
Non-Final Office Action for U.S. Appl. No. 16/904,868 mailed Mar. 12, 2024.
Non-Final Office Action for U.S. Appl. No. 17/179,116 mailed Feb. 26, 2024.
Non-Final Office Action for U.S. Appl. No. 17/378,015 mailed Jul. 5, 2024.

(56) References Cited

OTHER PUBLICATIONS

Non-Final Office Action for U.S. Appl. No. 17/444,792 mailed Oct. 30, 2024.
Non-Final Office Action for U.S. Appl. No. 17/446,256 mailed Feb. 13, 2024.
Non-Final Office Action for U.S. Appl. No. 17/446,654 mailed Jun. 25, 2024.
Non-Final Office Action for U.S. Appl. No. 17/450,864 mailed May 29, 2024.
Non-Final Office Action for U.S. Appl. No. 17/451,345 mailed Jul. 25, 2024.
Non-Final Office Action for U.S. Appl. No. 17/451,354 mailed Apr. 4, 2024.
Non-Final Office Action for U.S. Appl. No. 17/595,747 mailed Jun. 7, 2024.
Non-Final Office Action for U.S. Appl. No. 17/597,408 mailed Aug. 15, 2024.
Non-Final Office Action for U.S. Appl. No. 17/597,673 mailed Mar. 20, 2024.
Non-Final Office Action for U.S. Appl. No. 17/614,173 mailed Sep. 24, 2024.
Non-Final Office Action for U.S. Appl. No. 17/625,941 mailed Nov. 4, 2024.
Non-Final Office Action for U.S. Appl. No. 17/628,411 mailed Sep. 23, 2024.
Non-Final Office Action for U.S. Appl. No. 17/645,821 mailed Sep. 6, 2024.
Non-Final Office Action for U.S. Appl. No. 17/646,771 mailed Apr. 24, 2024.
Non-Final Office Action for U.S. Appl. No. 17/653,314 mailed Aug. 29, 2024.
Non-Final Office Action for U.S. Appl. No. 17/653,920 mailed Mar. 15, 2024.
Non-Final Office Action for U.S. Appl. No. 17/655,464 mailed Mar. 26, 2024.
Non-Final Office Action for U.S. Appl. No. 17/661,090 mailed May 22, 2024.
Non-Final Office Action for U.S. Appl. No. 17/663,330 mailed Jul. 1, 2024.
Non-Final Office Action for U.S. Appl. No. 17/664,487 mailed Jun. 17, 2024.
Non-Final Office Action for U.S. Appl. No. 17/664,914 mailed Jan. 31, 2024.
Non-Final Office Action for U.S. Appl. No. 17/749,340 mailed Aug. 14, 2024.
Non-Final Office Action for U.S. Appl. No. 17/757,311 mailed Oct. 22, 2024.
Non-Final Office Action for U.S. Appl. No. 17/758,316 mailed Aug. 28, 2024.
Non-Final Office Action for U.S. Appl. No. 18/003,029 mailed Mar. 26, 2024.
Non-Final Office Action for U.S. Appl. No. 18/139,523 mailed Aug. 26, 2024.
Non-Final Office Action for U.S. Appl. No. 18/140,751 mailed Jun. 21, 2024.
Non-Final Office Action for U.S. Appl. No. 18/164,800 mailed Mar. 22, 2024.
Non-Final Office Action for U.S. Appl. No. 18/389,009 mailed May 24, 2024.
Non-Final Office Action for U.S. Appl. No. 18/451,080 mailed Jul. 30, 2024.
Non-Final Office Action for U.S. Appl. No. 18/584,002 mailed Sep. 19, 2024.
Notice of Allowance for U.S. Appl. No. 16/369,676 mailed Jun. 17, 2024.
Notice of Allowance for U.S. Appl. No. 16/449,039 mailed Mar. 28, 2024.
Notice of Allowance for U.S. Appl. No. 16/452,145 mailed Jul. 11, 2024.
Notice of Allowance for U.S. Appl. No. 16/904,868 mailed Sep. 29, 2024.
Notice of Allowance for U.S. Appl. No. 17/051,550 mailed Feb. 7, 2024.
Notice of Allowance for U.S. Appl. No. 17/179,116 mailed Sep. 13, 2024.
Notice of Allowance for U.S. Appl. No. 17/326,980 mailed Apr. 5, 2024.
Notice of Allowance for U.S. Appl. No. 17/447,123 mailed Jul. 26, 2024.
Notice of Allowance for U.S. Appl. No. 17/448,811 mailed Jun. 14, 2024.
Notice of Allowance for U.S. Appl. No. 17/450,864 mailed Sep. 18, 2024.
Notice of Allowance for U.S. Appl. No. 17/453,260 mailed Apr. 8, 2024.
Notice of Allowance for U.S. Appl. No. 17/453,560 mailed Jan. 31, 2024.
Notice of Allowance for U.S. Appl. No. 17/501,591 mailed Jul. 31, 2024.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 17/661,090 mailed Oct. 30, 2024.
Notice of Allowance for U.S. Appl. No. 17/662,700 mailed Jun. 12, 2024.
Notice of Allowance for U.S. Appl. No. 17/662,700 mailed Mar. 6, 2024.
Notice of Allowance for U.S. Appl. No. 17/664,914 mailed Jul. 26, 2024.
Notice of Allowance for U.S. Appl. No. 17/667,097 mailed Aug. 28, 2024.
Notice of Allowance for U.S. Appl. No. 18/140,163 mailed Aug. 21, 2024.
Notice of Allowance for U.S. Appl. No. 18/140,751 mailed Nov. 1, 2024.
Notice of Allowance for U.S. Appl. No. 18/198,464 mailed Apr. 17, 2024.
Notice of Allowance for U.S. Appl. No. 18/198,464 mailed Jul. 30, 2024.
Notice of Allowance for U.S. Appl. No. 18/389,009 mailed Aug. 28, 2024.
Restriction Requirement for U.S. Appl. No. 17/527,769 mailed Jun. 17, 2024.
Restriction Requirement for U.S. Appl. No. 17/596,629 mailed Sep. 19, 2024.
Restriction Requirement for U.S. Appl. No. 17/625,941 mailed Aug. 7, 2024.
Restriction Requirement for U.S. Appl. No. 17/667,097 mailed Mar. 20, 2024.
Restriction Requirement for U.S. Appl. No. 17/756,201 mailed Oct. 4, 2024.
Restriction Requirement for U.S. Appl. No. 17/878,268 mailed Sep. 20, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
U.S. Appl. No. 17/013,822, filed Sep. 7, 2020.
U.S. Appl. No. 17/444,792, filed Aug. 10, 2021.
U.S. Appl. No. 18/249,577, filed Oct. 19, 2021.
U.S. Appl. No. 18/294,370, filed Feb. 1, 2024.
U.S. Appl. No. 18/294,403, filed Feb. 1, 2024.
U.S. Appl. No. 18/584,002, filed Feb. 22, 2024.
U.S. Appl. No. 18/610,523, filed Mar. 20, 2024.
U.S. Appl. No. 18/662,216, filed May 13, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 18/693,638, filed Mar. 20, 2024.

(56) References Cited

OTHER PUBLICATIONS

U.S. Appl. No. 18/694,090, filed Mar. 21, 2024.
U.S. Appl. No. 18/728,604, filed Jul. 12, 2024.
U.S. Appl. No. 18/757,964, filed Jun. 28, 2024.
U.S. Appl. No. 18/758,025, filed Jun. 28, 2024.
U.S. Appl. No. 18/828,559, filed Sep. 9, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 18/841,630, filed Aug. 26, 2024.
U.S. Appl. No. 18/851,197, filed Sep. 26, 2024.
U.S. Appl. No. 18/886,306, filed Sep. 16, 2024.
U.S. Appl. No. 18/903,592, filed Oct. 1, 2024.
U.S. Appl. No. 18/925,921, filed Oct. 24, 2024.
U.S. Appl. No. 18/930,014, filed Oct. 29, 2024.
U.S. Appl. No. 18/931,853, filed Oct. 30, 2024.
U.S. Appl. No. 63/564,696, filed Mar. 13, 2024.
U.S. Appl. No. 63/561,893, filed Dec. 11, 2023.
U.S. Appl. No. 63/568,615, filed Mar. 22, 2024.
U.S. Appl. No. 63/683,428, filed Aug. 15, 2024.
U.S. Appl. No. 63/711,438, filed Oct. 24, 2024.
U.S. Appl. No. 63/711,445, filed Oct. 24, 2024.
"Dictionary.com, Abut Definition and Meaning", Dictionary.com, https://www.dictionary.com/browse/abut, 2024, 1 page.
"Oblong", Cambridge Dictionary, https://dictionary.cambridge.org/dictionary/english/oblong, 2024, 1 page.
Britannica, "Polyolefin", Britannica Online Encyclopedia, T. Editors of Encyclopaedia, https://www.britannica.com/science/polyolefin, Jul. 26, 2012.
Martin, et al., "Chapter 5 Applications of Polyethylene Oxide (POLYOX) in Hydrophilic Matrices", Hydrophilic Matrix Tablets for Oral Controlled Release, AAPS Advances in the Pharmaceutical Sciences vol. 16, 2014, pp. 123-141.
Wikipedia Article, "Decibel", https://web.archive.org/web/20200415219171/https://en.wikipedia.org/wiki/Decibel last accessed Mar. 11, 2024, 21 pages.
Wikipedia Article, "Fiberglass", https://web.archive.org/web/20200309194847/https://en.wikipedia.org/wiki/Fiberglass last accessed Mar. 11, 2024.

* cited by examiner

FLUID COLLECTION DEVICES HAVING A SUMP BETWEEN A TUBE OPENING AND A BARRIER, AND RELATED SYSTEMS AND METHODS

CROSS-REFERENCE TO RELATED APPLICATIONS

This application is a continuation of U.S. application Ser. No. 18/299,788 filed on Apr. 13, 2023, which is a continuation of PCT International Application No. PCT/US2021/043893 filed on Jul. 30, 2021, which claims priority to U.S. Provisional Patent Application No. 63/154,248 filed on Feb. 26, 2021, the disclosure of each of which is incorporated herein, in its entirety, by this reference.

BACKGROUND

An individual may have limited or impaired mobility such that typical urination processes are challenging or impossible. For example, the individual may have surgery or a disability that impairs mobility. In another example, the individual may have restricted travel conditions such as those experienced by pilots, drivers, and workers in hazardous areas. Additionally, fluid collection from the individual may be needed for monitoring purposes or clinical testing.

Bed pans and urinary catheters, such as a Foley catheter, may be used to address some of these circumstances. However, bed pans and urinary catheters have several problems associated therewith. For example, bed pans may be prone to discomfort, spills, and other hygiene issues. Urinary catheters be may be uncomfortable, painful, and may cause urinary tract infections.

Thus, users and manufacturers of fluid collection devices continue to seek new and improved devices, systems, and methods to collect urine.

SUMMARY

Embodiments disclosed herein are related to fluid collection devices having a defined sump, and related systems and methods. In an embodiment, a fluid collection device includes a fluid impermeable barrier, a fluid permeable body, a tube, and a sump. The fluid impermeable barrier at least partially defines an opening and a chamber within the fluid collection device in fluid communication with the opening, and the fluid impermeable barrier having a proximal end region and a distal end region. The fluid permeable body is positioned within the chamber and extends at least partially between the distal end region and the proximal end region. The tube extends into the chamber and has an end positioned proximate to the distal end region of the fluid impermeable barrier. The tube includes a tube opening proximate to the end of the tube and oriented to face at least a portion of the fluid permeable body. The sump is positioned in the area between the tube opening and the distal end region of the fluid impermeable barrier.

In an embodiment, a method of collecting fluid includes positioning a fluid collection device on skin of a user. The fluid collection device includes a fluid impermeable barrier at least partially having a proximal and a distal end region and defining an opening and a chamber within the fluid collection device in fluid communication with the chamber. The fluid collection device also includes a fluid permeable body positioned within the chamber and extending at least partially between the distal end region and the proximal end region. The fluid collection device also includes a tube extending into the chamber and having an end positioned proximate to the distal end region of the chamber. The tube includes a tube opening at least proximate to the end of the tube and oriented to face at least a portion of the fluid permeable body. The method includes collecting fluid discharged from the user in the chamber of the fluid collection device and drawing the fluid from the fluid collection device through the tube.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Figure 1:
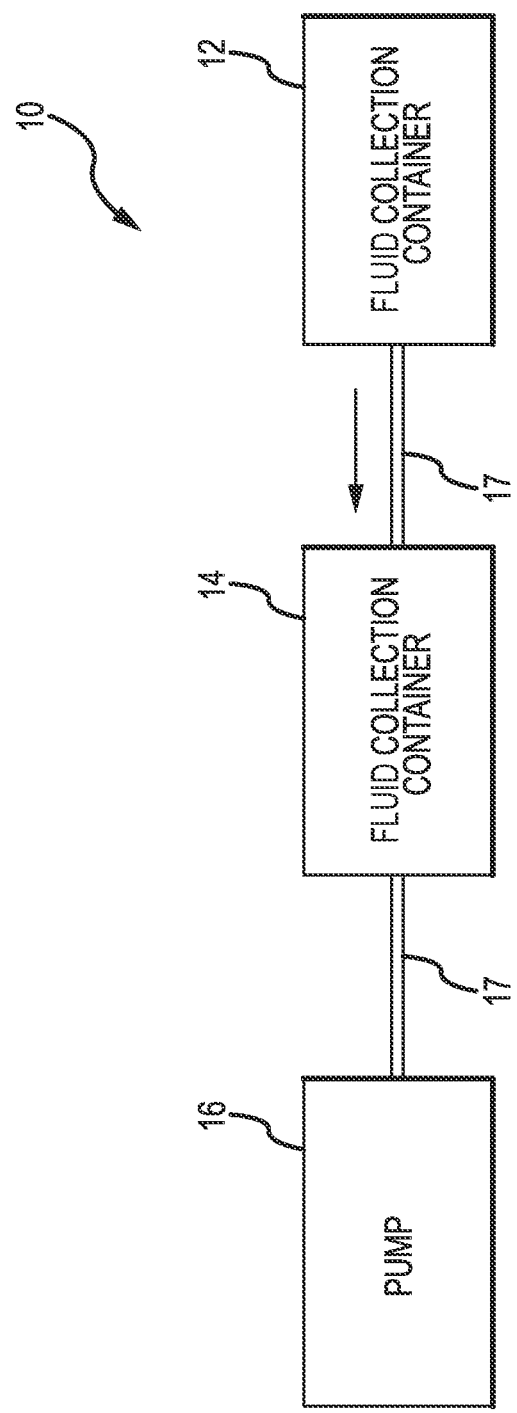
FIG. 1 is a block diagram of a fluid collection system, according to an embodiment.

Embodiments disclosed herein are related to fluid collection devices having a defined sump, and related systems and methods. A fluid collection device may include a fluid impermeable barrier, a fluid permeable body, and a tube. The fluid impermeable barrier at least partially defines an opening and a chamber within the fluid collection device in fluid communication with the chamber, and includes a proximal end region and a distal end region. A fluid permeable body is positioned within the chamber and extends at least partially between the distal end region and the proximal end region. The tube extends into the chamber and has an end positioned in the chamber proximate to the distal end region of the fluid impermeable barrier. The tube also includes a tube opening (e.g., inlet) proximate to the end of the tube and oriented to face at least a portion of the fluid permeable body.

A defined sump of the fluid collection device may include an area or region within the urine collection device where fluid may collect for removal from the fluid collection device. A fluid collection device may include, from top to bottom in use, a top portion of the fluid impermeable barrier, a portion of the fluid permeable body uncovered or spaced from the top portion to allow discharged urine to enter to the fluid permeable body, a tube opening on a vacuum tube, and at least a portion of the fluid permeable body positioned between the tube opening and a bottom layer of the fluid impermeable barrier of the fluid collection device. For example, fluid may be received on or in the fluid permeable body, and be drawn to the defined sump as fluid is drawn from the sump with the tube. In some embodiments, the defined sump may include at least an area or region within the chamber having the tube opening of the tube spaced from the distal end region of the fluid impermeable barrier. Thus, when fluid collects within the sump between the tube opening and the distal end region of the fluid impermeable barrier, the tube may remove the fluid from the sump. In some embodiments, the fluid permeable body extends between the tube opening and the distal end region of the fluid impermeable barrier, resulting in the technical effect of the fluid permeable body providing connections for molecular bonding of water in the fluid. This configuration of the fluid permeable body between the tube opening and the fluid impermeable barrier also results in the fluid being drawn into the tube through the tube opening drawing fluid in other regions of the fluid permeable body to the sump via the molecular bonding of the water in the fluid. A defined sump within embodiments of fluid collection devices described herein also may provide the technical effect of preventing a loss of vacuum on fluid being drawn from the fluid collection device, thereby improving fluid capture from the fluid collection device. A defined sump within embodiments of fluid collection devices described herein also provides for a fluid permeable body that results in the technical effect of a network promoting connection of molecular bonding of the fluid being collected, thereby improving fluid removal from the fluid collection device.

In conventional fluid collection devices, fluid is often difficult or inefficient to remove from the fluid collection device when the fluid collection device is in a substantially horizontal position. In some embodiments of fluid collection devices described herein, the fluid collection devices may include a horizontal sump for a vacuum assisted fluid collection device that results in the technical of effect of efficient operation of the fluid collection devices when in a substantially horizontal position. For example, some embodiments of the fluid collection device may be configured to for use as a skin or wound care fluid collection device that may be placed on skin such as the abdomen, interior thigh, or the chest, where there is typically no lowest point for liquid to pool in the fluid collection device. In some embodiments, the fluid collection device may include a male external catheter that may be generally horizontal during use, such as positioned on the scrotal area or on either side of the penis or above the penis (below the umbilicus). A defined horizontal sump may maximize fluid capture by the fluid collection device by optimizing the location and angle of contact of the tube opening within the sump.

A fluid collection device used in a horizontal position and having a horizontal sump may include, in order from either top to bottom or bottom to top, a portion of the fluid permeable body uncovered to allow fluid to enter to the fluid permeable body, a tube opening on a vacuum tube, and at least a portion of the fluid permeable body positioned between the tube opening and a fluid impermeable barrier of the fluid collection device. In use, the horizontal sump may not be the lowest point of the fluid collection device, but rather the region in the horizontal sump where fluid is collected. For example, when a vacuum is applied to the fluid permeable body, the entire fluid permeable body between the tube opening and the fluid impermeable barrier may be the horizontal sump. For example, in a male external catheter urine collection device, a top side of the fluid permeable body may be generally uncovered (or spaced from a top portion of the fluid impermeable barrier) to receive discharged urine, and the bottom side of the fluid permeable body may be positioned against the bottom portion of the fluid impermeable barrier. The horizontal sump, then, may include the entire region of the fluid permeable body between the opening in the fluid impermeable barrier and the distal end region of the fluid impermeable barrier.

FIG. 1 is a block diagram of a fluid collection system 10, according to an embodiment. The fluid collection system 10 may be included in any of the embodiments of fluid collection systems described herein. The system 10 includes a fluid (e.g., urine) collection device 12 (e.g., any of the fluid collection assemblies disclosed herein), a fluid collection container 14, and a pump 16 (or vacuum). The fluid collection device 12, the fluid collection container 14, and the pump 16 may be fluidly coupled to each other via one or more tubes 17 or conduits. For example, fluid collection device 12 may be operably coupled to one or more of the fluid collection container 14 or the pump 16 via the tube 17. In some embodiments, the pump 16 may be secured directly to the fluid collection container 14. Fluid (e.g., urine or other bodily fluids) collected in the fluid collection device 12 may be removed from the fluid collection device 12 via the tube 17 secured to the fluid collection device 12. Suction force may be introduced into the chamber of the fluid collection device 12 via the inlet of the tube 17 responsive to suction (e.g., vacuum) force applied at the outlet of the tube 17.

The suction force may be applied to the outlet of the tube 17 by the pump 16 either directly or indirectly. The suction force may be applied indirectly via the fluid collection container 14. For example, the outlet of the tube 17 may be disposed within or fluidly coupled to an interior region of the urine collection container 14 and an additional tube 17 may extend from the urine collection container 14 to the pump 16. Accordingly, the pump 16 may apply suction to the fluid collection device 12 via the fluid collection container 14. The suction force may be applied directly via the pump 16. For example, the outlet of the tube 17 may be disposed within the pump 16. An additional tube 17 may extend from the pump 16 to a point outside of the fluid collection device 12, such as to the fluid collection container 14. In such examples, the pump 16 may be disposed between the fluid collection device 12 and the fluid collection container 14.

The fluid collection container 14 is sized and shaped to retain a fluid therein. The fluid collection container 14 may include a bag (e.g., drainage bag), a bottle or cup (e.g., collection jar), or any other enclosed container for storing bodily fluid(s) such as urine. In some examples, the tube 17 may extend from the fluid collection device 12 and attach to the fluid collection container 14 at a first point therein. An additional tube 17 may attach to the urine collection container 14 at a second point thereon and may extend and attach to the pump 16. Accordingly, a vacuum (e.g., suction)

may be drawn through fluid collection device 12 via the fluid collection container 14. Fluid, such as urine, may be drained from the fluid collection device 12 using the pump 16.

The pump 16 may include one or more of a manual vacuum pump, and electric vacuum pump, a diaphragm pump, a centrifugal pump, a displacement pump, a magnetically driven pump, a peristaltic pump, or any pump configured to produce a vacuum. The pump 16 may provide a vacuum or suction to remove fluid from the fluid collection device 12. In some examples, the pump 16 may be powered by one or more of a power cord (e.g., connected to a power socket), one or more batteries, or even manual power (e.g., a hand operated vacuum pump). In some examples, the pump 16 may be sized and shaped to fit outside of, on, or within the fluid collection device 12. For example, the pump 16 may include one or more miniaturized pumps or one or more micro pumps. The vacuum sources disclosed herein may include one or more of a switch, a button, a plug, a remote, or any other device suitable to activate the pump 16.

Figure 2A:
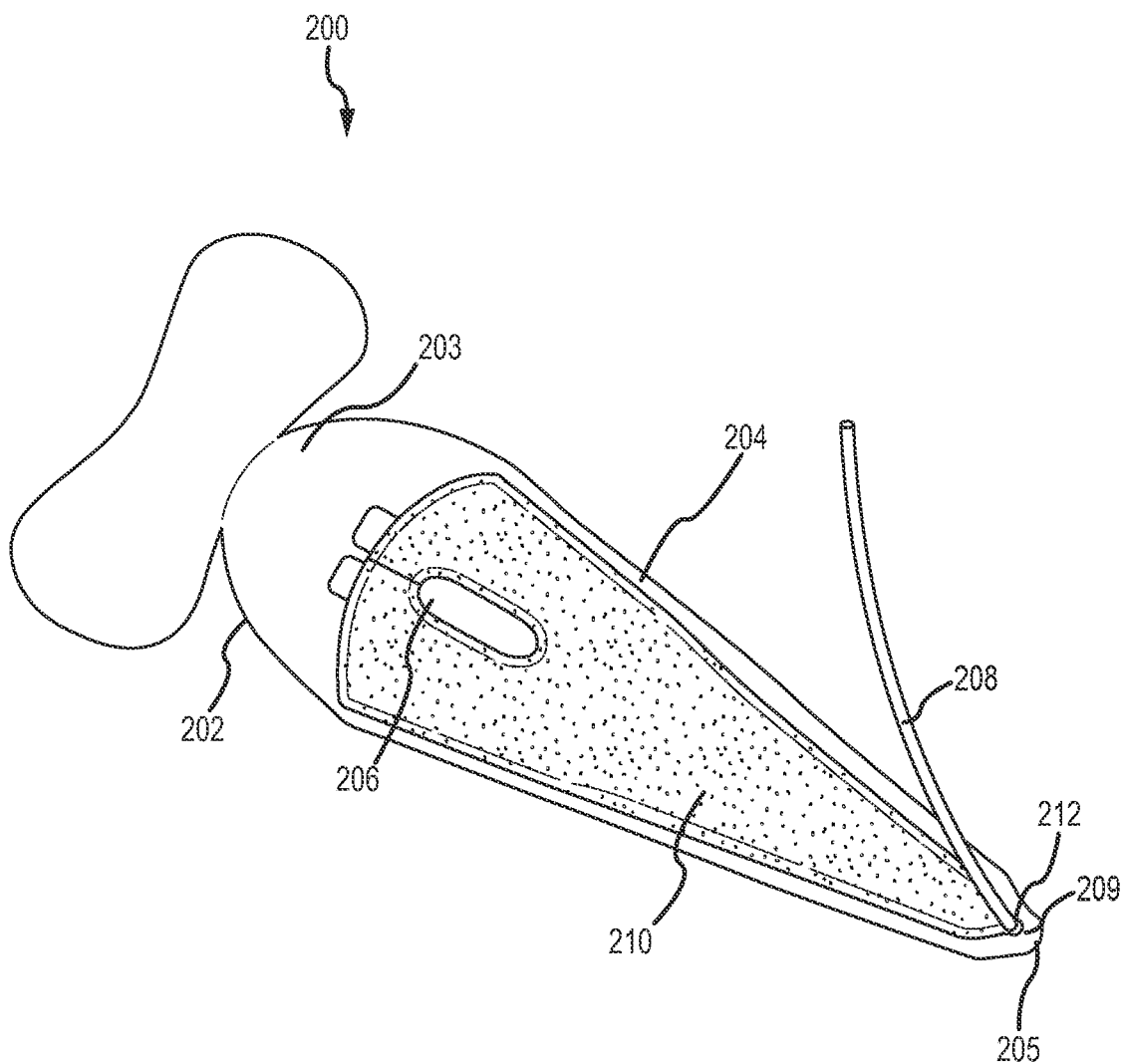
FIG. 2A is a front isometric view of a male urine collection device, according to an embodiment.

FIG. 2A is a front view of a male urine collection device 200, according to an embodiment. The urine collection device 200 includes a fluid impermeable barrier 202 at least partially defining an opening 206 and a chamber 204 within the fluid collection device in fluid communication with the opening 206. In some embodiments, a bottom portion of the fluid impermeable barrier 202 may define the opening 206 and an opposite or a top portion of the fluid impermeable bather 202 may define an aperture 212. The fluid impermeable barrier 202 includes a proximal end region 203 and a distal end region 205. The opening 206 may be positioned proximate or closer to the proximal end region 203 than the distal end region 205 of the fluid impermeable barrier 202, and the aperture 212 may be positioned proximate or closer to the distal end region 205 than the proximal end region 203. In some embodiments, the fluid impermeable barrier 202 narrows between the proximal end region 203 and the distal end region 205. For example, the fluid impermeable barrier 202 (and the chamber 204) may include a substantially triangular front profile, with the distal end region 205 being at the narrow end or tip of the triangular profile. The fluid impermeable bather 202 may include a shape substantially complementary to the chamber 204, such as a substantially triangular front profile. The fluid impermeable barrier 202 may include a substantially flexible fluid impermeable material, such as a fluid impermeable polymer (e.g., silicone, polypropylene, polyethylene, polyethylene terephthalate, a polycarbonate, etc.), polyurethane films, thermoplastic elastomer, oil, another suitable material, or combinations thereof. In some embodiments, the fluid impermeable barrier includes a paper-like or bag-like fluid impermeable material and/or a fluid impermeable fabric.

The urine collection device 200 also includes a fluid permeable body 210 positioned within the chamber 204 and extending at least partially between the distal end region 205 and the proximal end region 203. The fluid permeable body 210 may be shaped generally complementary to the shape of the chamber of the fluid impermeable barrier 202. In some embodiments, the fluid permeable body 210 is spaced from the edges of the fluid impermeable barrier 202 that extend at least partially between the distal end region 205 and the proximal end region 203. In some embodiments, the fluid permeable body 210 is positioned to abut the edges of the fluid impermeable barrier 202 such that fluid impermeable barrier 202 retains fluid in the fluid permeable body 210 from the opening 206 to the sump 209.

The fluid permeable body 210 can be configured to wick and/or allow transport of fluid away from the opening 206, thereby preventing the fluid from escaping the chamber 204. The fluid permeable body 210 also can wick and/or allow transport of the fluid generally towards the sump 209. The fluid permeable body 210 can include any material that can wick and/or allow transport of the fluid. The permeable properties referred to herein can be wicking, capillary action, diffusion, or other similar properties or processes, and are referred to herein as "permeable" and/or "wicking." Such "wicking" or other physical properties may exclude absorption into the fluid permeable body 210, such as not include adsorption of the bodily fluids into the fluid permeable body 210. Put another way, substantially no absorption or solubility of the bodily fluids into the material may take place after the material is exposed to the bodily fluids and removed from the bodily fluids for a time. While no absorption or solubility is desired, the term "substantially no absorption" may allow for nominal amounts of absorption and/or solubility of the bodily fluids into the fluid permeable body 210 (e.g., absorbency), such as less than about 30 wt % of the dry weight of the wicking material, less than about 20 wt %, less than about 10 wt %, less than about 7 wt %, less than about 5 wt %, less than about 3 wt %, less than about 2 wt %, less than about 1 wt %, or less than about 0.5 wt % of the dry weight of the fluid permeable body 210. In an embodiment, the fluid permeable body 210 may include at least one absorbent or adsorbent material.

The fluid permeable body 210 can include a one-way fluid movement fabric. As such, the fluid permeable body 210 can remove fluid from the area around the penis, thereby leaving the area and urethra dry. The fluid permeable body 210 can enable the fluid to flow generally towards the sump 209 and the tube 208 within the chamber 204. The fluid permeable body 210 can include a porous or fibrous material, such as hydrophilic polyolefin. In some embodiments, the fluid permeable body 210 consists of or consists essentially of a porous or fibrous material, such as hydrophilic polyolefin. Examples of polyolefin that can be used in the fluid permeable body 210 include, but are not limited to, polyethylene, polypropylene, polyisobutylene, ethylene propylene rubber, ethylene propylene diene monomer, or combinations thereof. Moreover, the fluid permeable body 210 can be manufactured according to various manufacturing methods, such as molding, extrusion, or sintering. The fluid permeable body 210 can include varying densities or dimensions.

In some embodiments, the fluid permeable body 210 can include two or more layers of fluid permeable materials. For example, the fluid permeable body 210 can include a fluid permeable membrane covering or wrapped around a fluid permeable support, with both the fluid permeable membrane and the fluid permeable support being disposed in the chamber 204. The fluid permeable membrane can cover or extend across at least a portion (e.g., all) of at least the side of the fluid permeable support facing the penis of the user. The fluid permeable membrane and the fluid permeable support can be configured to wick any fluid away from the opening 206, thereby preventing the fluid from escaping the chamber 204 and promoting removal of the fluid through the tube 208. The permeable properties referred to herein can be wicking, capillary action, diffusion, or other similar properties or processes, and are referred to herein as "permeable" and/or "wicking."

The fluid permeable membrane and the fluid permeable support also can wick the fluid generally towards an interior of the chamber 204, such as the sump 209. The fluid permeable membrane can include any material that can wick the fluid. For example, the fluid permeable membrane can include fabric, such as a gauze (e.g., a silk, linen, polymer based materials such as polyester, or cotton gauze), nylon (such as a spun nylon fibers), another soft fabric (e.g., jersey knit fabric or the like), or another smooth fabric (e.g., rayon, satin, or the like). Forming the fluid permeable membrane from gauze, soft fabric, and/or smooth fabric can reduce chaffing caused by the urine collection device 200. Other embodiments of fluid permeable membranes and fluid permeable supports are disclosed in U.S. patent application Ser. No. 15/612,325 filed on Jun. 2, 2017; U.S. patent application Ser. No. 15/260,103 filed on Sep. 8, 2016; U.S. patent application Ser. No. 15/611,587 filed on Jun. 1, 2017; PCT Patent Application No. PCT/US19/29608, filed on Apr. 29, 2019, the disclosure of each of which is incorporated herein, in its entirety, by this reference. In many embodiments, the fluid permeable body 210 includes a fluid permeable support including a porous spun nylon fiber structure and a fluid permeable wicking membrane including gauze at least partially enclosing the spun nylon fiber structure.

Figure 2B:
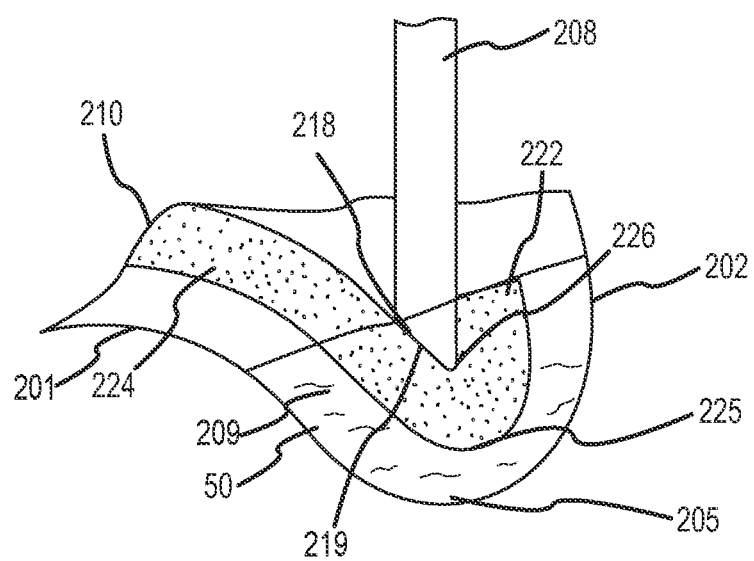
FIG. 2B is a cross-sectional view of distal end region of a male fluid collection device, according to an embodiment.

The urine collection device 200 also includes a tube 208 extending into the chamber 204 and having an end 218 positioned proximate to the distal end region 205 of the fluid impermeable barrier 202. As shown in FIG. 2B, the tube 208 includes a tube opening 219 proximate to the end 218 of the tube 208. Returning to FIG. 2A, a sump 209 may be defined as the region or area between the tube opening 219 and the distal end region 205 of the fluid impermeable barrier 202. At least some of the fluid permeable body 210 may extend into the sump 209. Fluid discharged on the fluid permeable body 210 may flow to and pool in the sump 209 for removal when a vacuum is applied on the tube 208. The tube 208 may extend through an aperture 212 in a top portion of the fluid impermeable barrier 202 and into the chamber 204. In some embodiments, a first portion of the tube 208 including the end 218 and the tube opening 219 may be fixedly connected to the fluid impermeable barrier proximate to the aperture 212 and a second portion of the tube 208 may removably secured or connected to the fluid collection device 200 proximate to the aperture 212. The aperture 212 may be positioned proximate to the distal end region 205 of fluid impermeable barrier 202. In some embodiments, the end 218 of the tube 208 and/or the tube opening 219 are positioned between the distal end region 205 and the aperture 212. In some embodiments, the aperture 212 is absent, and the tube 208 may exit the chamber 204 through the opening 206. U.S. Provisional Patent 63/067,542 describes embodiments of male external catheter urine collection devices, aspects of which may be used in any of the embodiments disclosed herein, the disclosure of which are incorporated in their entirety by this reference.

Turning to FIG. 2B, which is a side view of a distal end of the urine collection device 200. As urine is discharged onto the fluid permeable body 210, the urine may flow to the lowest point to form a pool 50 of urine at the distal end region 205 of the fluid impermeable barrier 202. The end 218 of the tube 208 and the tube opening 219 are spaced from the distal end region 205 of the fluid impermeable barrier 202 such that a sump 209 for the pool 50 of urine is defined between the tube opening 219 and/or the end 218 of the tube 208.

In some embodiments, at least a portion of the fluid permeable body 210 is positioned between the tube opening 219 (and/or the end 218 of the tube 208) and the distal end region 205 of the fluid impermeable barrier 202. The tube opening 219 may be oriented to face at least the portion of the fluid permeable body 210, which may be positioned between the tube opening 219 and the distal end region 205 of the fluid impermeable barrier 202. In some embodiments, the fluid permeable body 210 may cover the tube opening 219. As used herein, covering of the tube opening 219 by the fluid permeable body 210 includes extending at least partially (e.g., entirely) across the tube opening 219, even if the tube opening 219 is oriented downward. That is, the fluid permeable body 210 may over the tube opening 219 below the tube opening 219. The fluid permeable body 210 may include a recess 226 proximate to the distal end region 205 and the tube opening 219 may be positioned at least partially (e.g., entirely) within the recess 226 with a distal portion or tip 225 of the fluid permeable body 210 between the tube opening 219 and the distal end region 205 of the fluid impermeable bather 202. Accordingly, the tube opening 219 may be embedded within the fluid permeable body 210. In some embodiments, the fluid permeable body 210 includes a bottom portion 224 extending from the distal end region 205 towards the proximal end region 203. The bottom portion 224 of the fluid permeable body 210 may interface a bottom portion 201 of the fluid impermeable barrier 202, which rests or is positioned on a user. The bottom portion 224 of the fluid permeable body 210 may be substantially planar. The fluid permeable body 210 also may include a lip 222 positioned proximate to the distal end region 205 fluid impermeable barrier 202. The recess 226 may be at least partially defined by the fluid permeable body 210 between the lip 222 and the bottom portion 224 of the fluid permeable body 210.

In some embodiments, the distal portion 225 of the fluid permeable body 210 is shaped substantially complementary to the distal end region 205. The distal portion 225 of the fluid permeable body 210 may be spaced from the distal end region 205 of the fluid impermeable barrier 202, such that a portion of the sump 209 is devoid of the fluid permeable body 210. In some embodiments, the distal portion 225 of the fluid permeable body 210 interfaces at least a portion (e.g., all) of the fluid impermeable barrier 202 at the distal end region 205.

In some embodiments, the end 218 of the tube 208 includes a beveled end 218 with the tube opening 219 positioned at the beveled end 218. Whereas the end of a conventional tube is typically perpendicular to the sidewall of the conventional tube, the beveled end 218 of the tube 208 is at an acute or obtuse angle relative to the sidewall of the tube 208. With the beveled end 218 being angled relative to the sidewall of the tube 208, when the beveled end 218 and the tube opening 219 are generally horizontal, the tube 208 may angle relative to the bottom portion 224 of the fluid permeable body 210 and/or the bottom portion 201 of the fluid impermeable barrier 202. For example, the tube 208 may angle from the beveled end 218 towards the aperture 212 and out of the chamber 204, similar to the embodiment shown in FIG. 3A.

Embodiments having a beveled end 218 may be used when the urine collection device 200 is positioned generally horizontal on a user. In operation, when a vacuum is applied to the tube 208, the tube 208 draws fluid from the sump 209 into the tube 208 through the tube opening 219. The fluid permeable body 210 provides connections for molecular bonding of fluid (e.g., urine) in the chamber 204. The urine being drawn into the tube 208 through the tube opening 219, then, also may draw urine in the fluid permeable body 210 to the sump 209 via the molecular bonding of the water in the urine. The configuration of the sump 209 within the urine collection device 200 may prevent a loss of vacuum on fluid being drawn from the urine collection device 200, thereby improving fluid capture from the fluid collection device. In some embodiments, the distal end region 205 of the fluid impermeable barrier 202 may be the low point of the urine collection device 200 during use, and the tube 208 may include an end that is generally perpendicular to the sidewall of the tube 208.

Figure 3A:
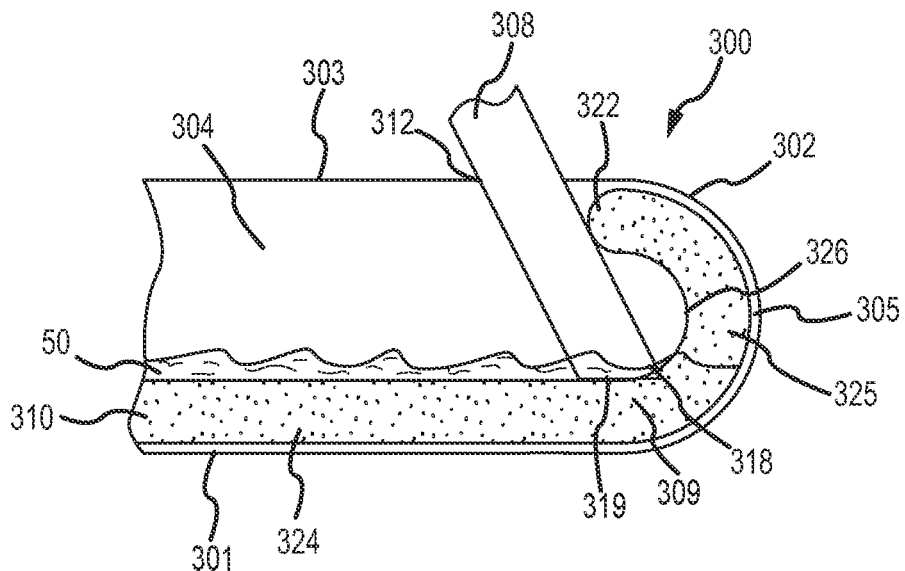
FIG. 3A is a cross-sectional view of a distal end region of a fluid collection device, according to an embodiment.

FIG. 3A shows a distal end region 305 of a urine collection device 300 in a substantially horizontal position during use. Although only the distal end region 305 of the fluid collection device 300 is shown, unless otherwise noted, the fluid collection device 300 may include any aspect of the fluid collection device 200. For example, the fluid collection device 300 may include a fluid impermeable barrier 302 defining an opening (not shown) on a bottom portion 301 of the fluid impermeable barrier 302 and an aperture 312 on a top portion 303 of the fluid impermeable barrier 302 having a distal end region 305, a chamber 304, a fluid permeable body 310, and a tube 308 having an end 318 and a tube opening 319 that, unless otherwise noted, include any aspect of the fluid impermeable barrier 202 defining the opening 206 and the aperture 212, the chamber 204, the fluid permeable body 210, and the tube 208 having the end 218 and the opening 219 of the urine collection device 200. The fluid impermeable barrier 302 may include a bottom portion 301 and a top portion 303, with the chamber 304 defined between the bottom portion 301 and the top portion 303. The bottom portion 301 may be positioned on the user and may define the opening (not shown), and the top portion 303 may define the aperture 312 positioned proximate to the distal end region 305 of the fluid impermeable barrier 302.

The fluid permeable body 310 may include bottom portion 324 positioned on at least a portion of the bottom portion 301 of the fluid impermeable barrier 302. The fluid permeable body 310 may include a recess 326 proximate to the distal end region 305 of the fluid impermeable barrier 302 and the tube opening 319 may be positioned at least partially within the recess 326. The fluid permeable body 310 also may include a lip 322 positioned proximate to the distal end region 305 of the fluid impermeable barrier 302. The lip 322 may interface or be positioned against part of the top portion 303 of the fluid impermeable barrier 302. The recess 326 may be at least partially defined by the distal portion 325 of the fluid permeable body 310 between the lip 322 and the bottom portion 324 of the fluid permeable body 310. In some embodiments, the fluid permeable body 310 curls from the bottom portion 324 to the lip 322. The lip 322 and the distal portion 325 of the fluid permeable body 310 may be shaped complementary to and interface with the distal end region 305 of the fluid impermeable barrier 302.

At least a portion of the fluid permeable body 310 is positioned between the tube opening 319 and the fluid impermeable barrier 302. The tube opening 319 may be oriented to face at least the portion of the fluid permeable body 310 that may be positioned between the tube opening 319 and distal end region 305 of the fluid impermeable barrier 302. For example, the bottom portion 324 and/or the distal portion 325 of the fluid permeable body 310 may be positioned between tube opening 319 and the fluid impermeable barrier 302. In some embodiments, the urine collection device 300 may be used in a generally horizontal position with the bottom portion 324 of the fluid permeable body 310 and the bottom portion 301 of the fluid impermeable barrier 302 substantially horizontal, as shown in FIG. 3A. In the generally horizontal position, the beveled end 318 of the tube 308 may be substantially horizontal and at least partially positioned in the recess 326. The tube 308 may angle from the beveled end 318 to the aperture 312 at an acute angle relative to the bottom portion 324 of the fluid permeable body 310 and/or the bottom portion 301 of the fluid impermeable barrier 302. When in a generally horizontal position, the sump 309 of the urine collection device 300 may be positioned at least partially in the chamber 304 at the distal end region 305 of between the tube opening 319 and the bottom portion 301 of the fluid impermeable barrier 302, with the bottom portion 324 of the fluid permeable body 310 positioned therebetween. In some embodiments, the bottom portion 324 of the fluid permeable body 310 may interface or be adjacent to the tube opening 319. For example, part of the bottom portion 324 of the fluid permeable body may cover or extend across at least a portion (e.g., all) of the tube opening 319. The beveled end 318 of the tube 308 and the positioning of the sump 309 between the beveled end 309 and the fluid impermeable barrier 302 allows urine 50 to be drawn through the fluid permeable body 310 to the sump 309, and drawn into the tube 308 through the tube opening 319 when a vacuum is applied to the tube 308. The end 318 of the tube 308 may be positioned proximate to the lateral margin or distal end of the sump 309. In some embodiments, only the distal portion 325 of the fluid permeable body 310 is positioned in the chamber 304 between the end 318 of the tube 308 and the distal end region 305 of the fluid impermeable barrier 302.

In some embodiments, the urine collection device 300 may be configured for use with the distal end region 305 of the fluid impermeable barrier 302 at a low point of the urine collection device 300 during use. When the distal end region 305 is at the low point of the urine collection device 300 during use, a tube having an end generally perpendicular to the sidewalls of the tube may be used to draw urine 50 from the urine collection device 300. For example, the end of the tube may be inserted into the recess 326 with the distal portion 325 of the fluid permeable body 310 positioned in the chamber 304 between the end of the tube and the distal end region 305 of the fluid impermeable barrier 302. When the distal end region 305 is at the low point of the urine collection device 300 during use, the sump 309 may be positioned in the chamber 304 between the end of the tube and the distal end region 305 of the fluid impermeable barrier 302. In some embodiments of the fluid collection device in a horizontal position, the sump 309 includes a region of the fluid permeable body 310 between the opening in the fluid impermeable barrier and the tube opening 319. The sump 309 may further extend in the fluid permeable body 310 to the end of the lip 322. The fluid permeable body 310 may promote molecular bonding of the fluid held in the fluid permeable body 310, and the tube opening 319 may abut and/or be adjacent to the fluid permeable body 310 such that molecular bonds are not broken by a space of air between the tube opening 319 and the fluid 50.

Figure 3B:
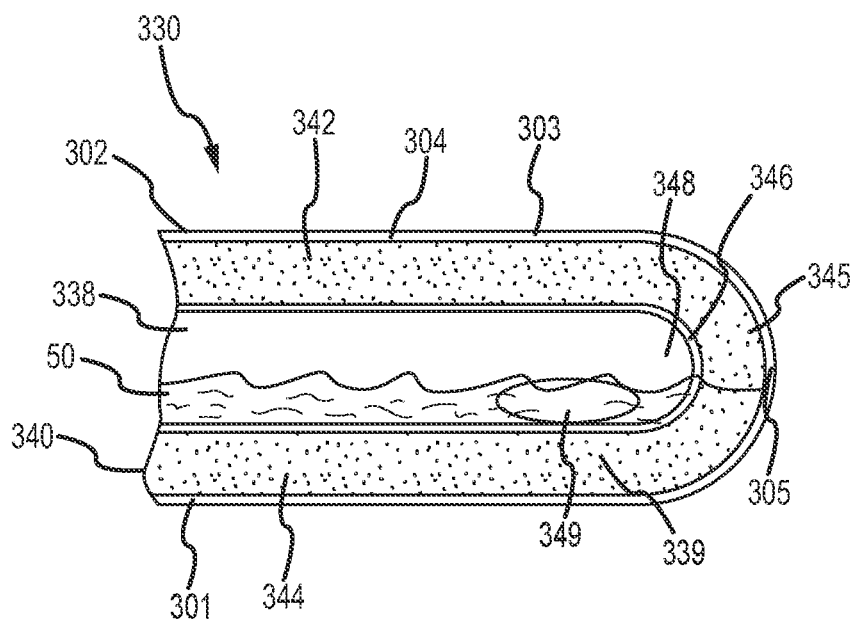
FIG. 3B is a cross-sectional view of a distal end region of a fluid collection device, according to an embodiment.

FIG. 3B shows a distal end region 305 of a urine collection device 330 in a substantially horizontal position during use. Although only the distal end region 305 of the fluid collection device 330 is shown, unless otherwise noted, the fluid collection device 330 may include any aspect of the fluid collection devices 200, 300. For example, the fluid collection device 330 may include a fluid impermeable barrier 302 having a bottom portion 301 and a top portion 303. The fluid impermeable barrier 302 may include the distal end region 305 and define an opening (not shown) and a chamber 304.

The urine collection device 330 may include a fluid permeable body 340. The fluid permeable body 340 may include any aspect of the fluid permeable bodies 210, 310, such as the materials of the fluid permeable body 210. The fluid permeable body 340 may include bottom portion 344 positioned on at least a portion of the bottom portion 301 of the fluid impermeable barrier 302, and a top portion 342 positioned adjacent to or interfacing at least a portion of the top portion 303 of the fluid impermeable barrier 302. A distal portion 345 of the fluid permeable body may connect the top portion 342 and the bottom portion 344 of the fluid permeable body 340. The fluid permeable body 340 may include tubular channel 346 extending between the top portion 342 and the bottom portion 344 of the fluid permeable body 340. The tubular channel 326 may extend into the fluid permeable body 340 to the distal portion 345 of the fluid permeable body 340. The fluid permeable body 340 may be shaped complementary to and interface with the distal end region 305 of the fluid impermeable barrier 302.

The urine collection device 330 also may include a tube 338 having a tube opening 349 spaced from an end 348 of the tube 338. In some embodiments, the end 348 of the tube 338 is capped, closed, or covered such that fluid communication through the end 348 of the tube 338 is absent. Rather than being positioned at the end 348 of the tube 338, the tube opening 349 may be defined and/or positioned in a sidewall of the tube 338. With the tube opening 349 in the sidewall of the tube 348, the tube opening 349 may be oriented towards the bottom portion 301 of the fluid impermeable barrier 302 and/or the bottom portion 344 of the fluid permeable body 340.

At least a portion of the fluid permeable body 340 is positioned between the tube opening 349 and the fluid impermeable barrier 302. The tube opening 349 may be oriented to face at least the portion of the fluid permeable body 340 that may be positioned in the chamber 304 between the tube opening 349 and distal end region 305 of the fluid impermeable barrier 302. For example, the bottom portion 344 may be positioned between tube opening 349 and the fluid impermeable barrier 302. In some embodiments, the urine collection device 330 may be used in a generally horizontal position with the bottom portion 344 of the fluid permeable body 340 and the bottom portion 301 of the fluid impermeable barrier 302 substantially horizontal, as shown in FIG. 3B. In the generally horizontal position, the covered or capped end 348 of the tube 338 may abut or interface the distal portion 345 of the fluid permeable body 340 in the tubular channel 346. The tube opening 349 in the sidewall of the tube 338 may be oriented downwards to the bottom portion 344 of the fluid permeable body 340 and the bottom portion 301 of the fluid impermeable barrier 302. The tube 338 may be substantially horizontal within at least the distal region of the tubular channel 348 as the tubular channel 348 approaches the distal end region 305 of the fluid impermeable barrier 302. In some embodiments, the tube 338 exits the chamber 304 through the opening (next to the penis).

When in a generally horizontal position, the sump 339 of the urine collection device 330 may be positioned at least partially in the chamber 304 proximate to the distal end region 305 between the tube opening 349 and the bottom portion 301 of the fluid impermeable barrier 302, with the bottom portion 344 of the fluid permeable body 340 positioned therebetween. The sump 339 may continue through the distal portion 345 of the fluid permeable body 340 as the fluid permeable body 330 wraps around the end 348 of the tube 338. In some embodiments, the bottom portion 344 of the fluid permeable body 340 may interface or be adjacent to the tube opening 349. For example, part of the bottom portion 344 of the fluid permeable body 340 may cover or extend at least partially (e.g., entirely) across the tube opening 349. The orientation of the tube opening 349 towards the bottom portion 301 of the fluid impermeable barrier 302 allows urine 50 to be drawn through the fluid permeable body 310 to the sump 339, and drawn into the tube 338 through the tube opening 349 when a vacuum is applied to the tube 338.

Figure 3C:
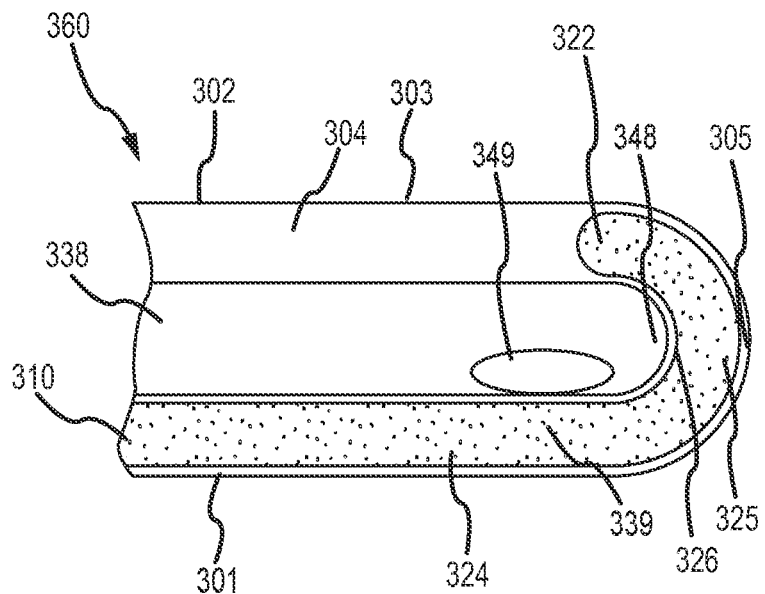
FIG. 3C is a cross-sectional view of a distal end region of a fluid collection device, according to an embodiment.

FIG. 3C shows a distal end region 305 of a urine collection device 360 in a substantially horizontal position during use. The urine collection device 360 may include the fluid permeable body 310 of the urine collection device 300, and the fluid impermeable barrier 302 and the tube 338 of the urine collection device 330. The capped or covered end 348 of the tube 338 may be positioned in the recess 326 of the fluid permeable body 310. A sump 369 may be positioned between the tube opening 349 and the bottom portion 301 of the fluid impermeable barrier 302, similar to the sump 339. Urine may be withdrawn from the urine collection device 360 when the urine collection device 360 is in the horizontal position, similar to the withdrawal of urine from the urine collection device 330, described above.

Figure 3D:
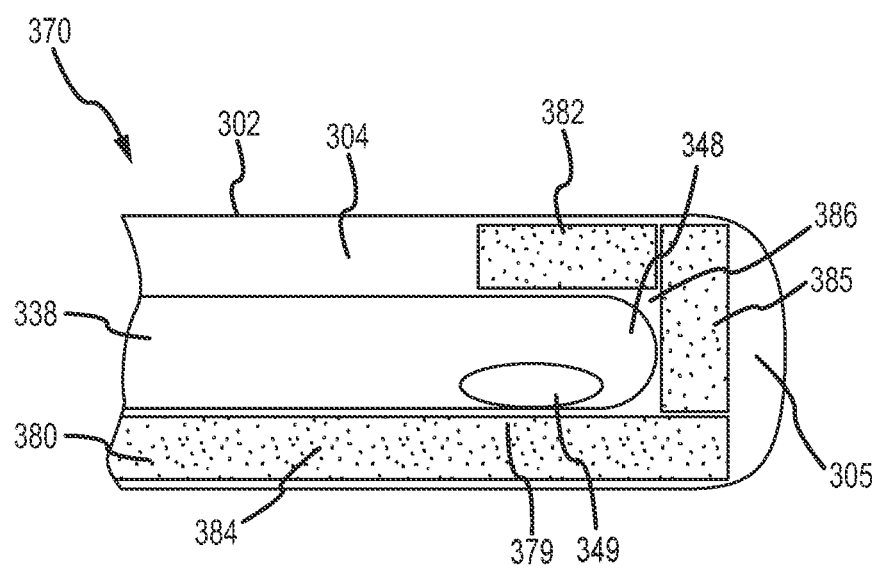
FIG. 3D is a cross-sectional view of a distal end region of a fluid collection device, according to an embodiment.

FIG. 3D shows a distal end region 305 of a urine collection device 370 in a substantially horizontal position during use. Although only the distal end region 305 of the fluid collection device 370 is shown, unless otherwise noted, the fluid collection device 370 may include any aspect of the fluid collection devices 200, 300, 330, 360. For example, the fluid collection device 370 may include a fluid impermeable barrier 302 having a bottom portion 301 and a top portion 302. The fluid impermeable barrier 302 may include the distal end region 305 and define an opening (not shown) and a chamber 304.

The urine collection device 370 may include a fluid permeable body 380. The fluid permeable body 380 may include any aspect of the fluid permeable bodies 210, 310, such as the materials of the fluid permeable body 210. The fluid permeable body 380 may include a bottom portion 384 positioned on at least a portion of the bottom portion 301 of the fluid impermeable barrier 302. The fluid permeable body 310 may include a recess 386 proximate to the distal end region 305 of the fluid impermeable barrier 302. The fluid permeable body 380 also may include a lip 382 positioned proximate to the distal end region 305 of the fluid impermeable barrier 302. The lip 382 may interface or be positioned against part of the top portion 303 of the fluid impermeable barrier 302. The recess 326 may be at least partially defined by the distal portion 385, the top portion 382, and the bottom portion 384 of the fluid permeable body 380. In some embodiments, the bottom portion 384, the distal portion 385, and the top portion 382 are three separate pieces or elements positioned within the chamber 304.

The urine collection device 370 also may include the tube 338 having the tube opening 349 spaced from the end 348 of the tube 338. The tube opening 349 may be oriented towards the bottom portion 301 of the fluid impermeable barrier 302 and/or the bottom portion 344 of the fluid permeable body 340. The bottom portion 384 may be positioned between tube opening 349 and the fluid impermeable barrier 302. In some embodiments, the urine collection device 370 may be used in a generally horizontal position with the bottom portion 384 of the fluid permeable body 380 and the bottom portion 301 of the fluid impermeable barrier 302 substantially horizontal, as shown in FIG. 3D. In the generally horizontal position, the covered or capped end 348 of the tube 338 may abut or interface the distal portion 385 of the fluid permeable body in the recess 386. The tube opening 349 in the sidewall of the tube 338 may be oriented downwards to the bottom portion 384 of the fluid permeable body 380 and the bottom portion 301 of the fluid impermeable barrier 302. The tube 338 may be substantially horizontal and may exit the chamber 304 through the opening (next to the penis).

A sump 379 may be positioned between the tube opening 349 and the bottom portion 301 of the fluid impermeable barrier 302, similar to the sumps 339, 369. Urine may be withdrawn from the urine collection device 370 when the urine collection device 370 is in the horizontal position, similar to the withdrawal of urine from the urine collection devices 330, 360, described above.

Figure 4:
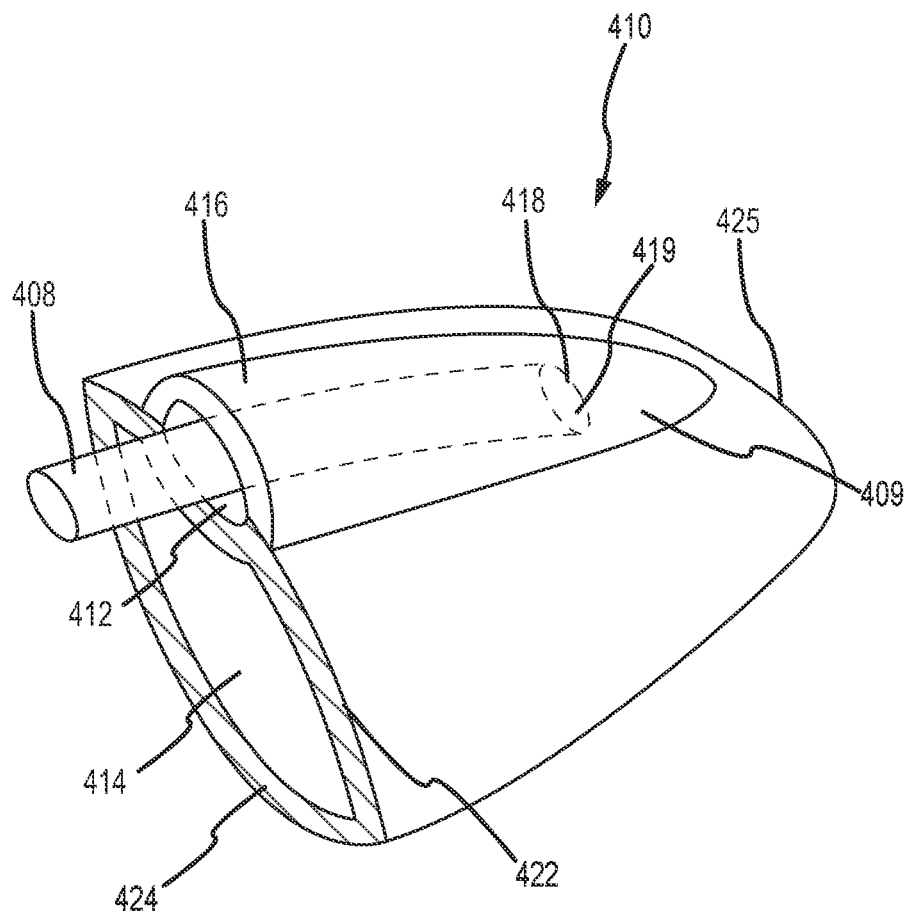
FIG. 4 is a front isometric view of a distal end region of a fluid permeable body, according to an embodiment.

FIG. 4 shows a distal end of fluid permeable body 410 that may be used in a male urine collection device. For example, the fluid permeable body 410 may be positioned within the chambers 204, 304 of the fluid impermeable bathers 202, 302. The fluid permeable body 410 may include any of the materials described above in relation to the fluid permeable body 210. In some embodiments, the fluid permeable body 410 includes a first portion 422 and a second portion 424. The first portion 422 may be positioned proximate or adjacent to a bottom portion of the fluid impermeable barrier and the second portion 424 may be positioned proximate or adjacent to a top portion of the fluid impermeable barrier. Alternatively, the first portion 422 may be positioned proximate or adjacent to the top portion of the fluid impermeable barrier and the second portion 424 may be positioned proximate or adjacent to the bottom portion of the fluid impermeable barrier. An open region 414 may be positioned between the first portion 422 and the second portion 424 of the fluid permeable body 420. In some embodiments, the second portion 424 of the fluid permeable body 410 is absent, and the first portion 422 of the fluid permeable body 410 may be positioned adjacent the bottom portion of the fluid impermeable barrier with a channel wall 416 positioned proximate or adjacent to the top portion of the fluid impermeable barrier. In some embodiments, the fluid permeable body 410 may be used with the channel wall 416 proximate to the bottom portion of the fluid impermeable barrier.

The fluid permeable body 410 also may include a channel 412 sized to receive at least a portion of a tube 408. The channel 412 may be at least partially defined by the first portion 422 of the fluid permeable body 410. In some embodiments, the channel 412 may be defined by the top portion 422 of the fluid permeable body 410 and a channel wall 416. The channel 412 may be generally tubular. The channel wall 416 may include any of the materials of the fluid permeable body 210. In some embodiments, the channel wall 416 is integrally formed with the first portion 422 of the fluid permeable body 410 with the channel 412 between the first portion 422 and the channel wall 416. The channel 412 may extend from proximate to a distal end 425 of the fluid permeable body 410 towards the opening in the fluid impermeable barrier.

A urine collection device having the fluid permeable body 410 also may include a tube 408 configured to provide fluid communication between the sump 409 and chamber of the urine collection device and a vacuum source. The tube 408 may include any aspect of the tubes 208, 308 described herein. In some embodiments, the tube 408 includes an opening 419 at an end 418 of the tube 408 that is generally perpendicular to the sidewall of the tube 408 (e.g., a beveled end may be absent from the tube 408). When the fluid permeable body 410 and the tube 408 are positioned within a chamber of a fluid impermeable barrier, a sump 409 may be formed at least partially in the fluid permeable body 410 between the tube opening 419 and the a distal end of the fluid impermeable barrier. The channel 412 may form a pocket for the tube 408 that directs or biases the end 418 and the tube opening 419 to stay in contact with the fluid permeable body 410. The channel 412 also may end or terminate spaced or distanced from the distal portion 425 of the fluid permeable body 410 such that the tube opening 419 is kept spaced from the fluid impermeable barrier. In use, the fluid permeable body 410 may direct urine to the tube opening 419, similar to the fluid permeable body 210 described above in relation to the urine collection device 200.

Figure 5:
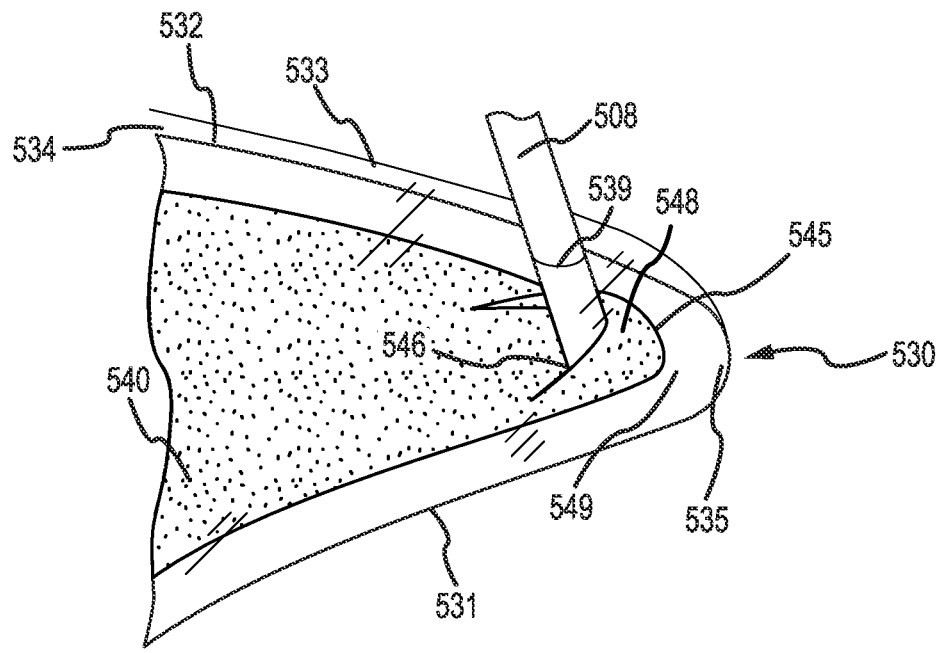
FIG. 5 is a front isometric view of a distal end region of a fluid collection device, according to an embodiment.

FIG. 5 is a front isometric view of the distal end of fluid collection device 530. Although only the distal end of the fluid collection device 530 is shown, unless otherwise noted, the fluid collection device 530 may include any aspect of the fluid collection device 200. In some embodiments, the fluid collection device 530 includes a fluid impermeable barrier 532 having a distal end region 535, a bottom portion 531, and a top portion 533. A chamber 534 and an aperture 539 may be at least partially defined by the fluid impermeable barrier 532.

The fluid collection device 530 also includes a fluid permeable body 540. Unless otherwise noted, the fluid permeable body 540 may include any aspect of the fluid permeable body 210, such as the materials and layers described in relation to the fluid permeable body 210. The fluid permeable body 540 may include a crescent-shaped protrusion 548 at least partially defining a pocket 546 between a portion of the crescent-shaped protrusion 548 and the distal portion 545 of the fluid permeable body 540. The pocket 546 may be sized to receive the end and at least a portion of the tube 508.

The tube 508 may extend through the aperture 539 in the top portion 533 of the fluid impermeable barrier 532 and into the pocket 546. The tube 508 may include flat end or a beveled end similar or the same as the beveled end of the tubes 208, 308. The end of the tube 508 may be positioned within the pocket 546 such that the tube opening at the end of the tube 508 is enveloped by the fluid permeable body 540 within the pocket 546. With the end of the tube 508 positioned in the pocket 546 and spaced from the distal end region 535 of the fluid impermeable barrier 532 and the bottom portion 531 of the fluid impermeable barrier 532, a sump 549 may be defined between the end of the tube 508 and the fluid impermeable barrier 532 in the distal end region 535 of the fluid impermeable barrier 532. Urine may be drawn into the tube 508 similar to other urine collection devices, such as the urine collection device 200.

In some embodiments of urine or fluid collection devices 200, 300, 330, 360, 370, 400, and 500, the fluid impermeable barrier defining of the chamber may include a silicone shell configured to retain its shape at the distal end region. In some embodiments of urine or fluid collection devices 200, 300, 330, 360, 370, 400, and 500, at least one of a wire coil or plastic may be positioned proximate the distal end of the fluid impermeable barrier and configured to inhibit collapse of the chamber proximate to the distal end region. In some embodiments of urine or fluid collection devices 200, 300, 330, 360, 370, 400, and 500, the chamber may include a filler material in a portion of the chamber proximate to the distal end region of the fluid impermeable barrier. The filler material may include at least one of netting, beads, or straws that inhibit collapse of the chamber proximate to the distal end region.

Aspects of fluid permeable bodies and the sumps of the urine or fluid collection devices 200, 300, 330, 360, 370, 400, and 500 may be applied to other urine collection devices. For example, PCT International Application No. PCT/US2019/029616, U.S. patent application Ser. No. 15/260,103, U.S. patent application Ser. No. 16/433,773, and U.S. Provisional Patent Application No. 63/067,542 describe various embodiments of both male and female fluid collection devices, including fluid permeable and fluid impermeable materials, that may be used in any of the embodiments disclosed herein, the disclosure of which are incorporated in their entirety by this reference. In some embodiments, the fluid collection device may include a female urine collection device having a substantially tubular fluid impermeable barrier defining an aperture at the proximal end of the fluid impermeable barrier and an opening positioned between the distal end region and the proximal end region of the fluid impermeable barrier. The fluid permeable body in the female urine collection device may include a substantially cylindrical portion extending across at least a portion (e.g. all) of the opening. The fluid permeable body also may include a distal portion defining a recess to receive the end of a tube therein, similar to the fluid permeable bodies 340, 350.

Figure 6:
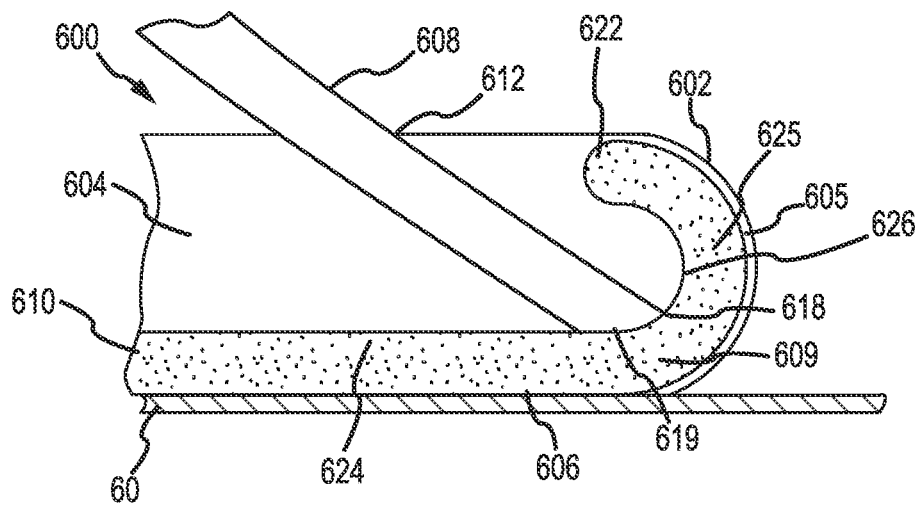
FIG. 6 is a cross-sectional view of a distal end region of a fluid collection device, according to an embodiment.

In some embodiments, a fluid collection device may be used to remove fluid from a wound or other regions of the body (besides the urethra) where fluids may collect or be discharged. FIG. 6 is a partial side view of a fluid collection device 600. The fluid collection device 600 may, for example, be used in removing wound drainage from a wound. The fluid collection device 600 may include a fluid impermeable barrier 602 defining an opening 606 and an aperture 612. The opening 606 may be positioned on a side of the fluid collection device 600 that is to be disposed on or at least proximate to the skin 60 of the user. The aperture 612 may be positioned substantially opposite to the opening 606. The fluid impermeable barrier 602 may include a distal end region 605 and may at least partially define a chamber 604 within the fluid collection device 600.

The fluid collection device 600 also includes a fluid permeable body 610. The fluid permeable body may include any aspect of the fluid permeable body 210, such as the materials of the fluid permeable body 210. The fluid permeable body 610 may include bottom portion 624 extending across at least a portion (e.g., all) of the opening 606 such that the bottom portion 624 of the fluid permeable body 610 may be positioned at least proximate to the skin 60. For example, a fluid permeable membrane of the fluid permeable body 610 may be disposed on the skin 60. The fluid permeable body 610 may include a recess 626 proximate to the distal end region 605 of the fluid impermeable barrier 602 and a tube opening 619 of a tube 608 may be positioned at least partially within the recess 626. The fluid permeable body 610 also may include a lip 622 positioned proximate to the distal end region 605 of the fluid impermeable barrier 602. The lip 622 may interface or be positioned against part of a top portion of the fluid impermeable barrier 602 and/or a portion of the fluid impermeable barrier 602 defining the distal end region 605 of the fluid impermeable barrier 602. The recess 626 may be at least partially defined by the distal portion 625 of the fluid permeable body 610 between the lip 622 and the bottom portion 624 of the fluid permeable body 610. In some embodiments, the fluid permeable body 610 curls from the bottom portion 624 to the lip 622. The lip 622 and the distal portion 625 of the fluid permeable body 610 may be shaped complementary to and interface with the distal end region 605 of the fluid impermeable barrier 602.

The tube 608 may extend through the aperture 612 into the chamber 604 and may include a beveled end 618. In some embodiments, a conduit including the end and the tube opening is fixedly formed in the chamber 604 extending from the top portion of the fluid impermeable barrier 602, and the tube 608 may be detachable secured to connected to the fluid collection device 600 proximate to the aperture 612. The tube opening 619 may be positioned at the beveled end 618 of the tube 608. The beveled end 618 of the tube 608 is at an acute or obtuse angle relative to the sidewall of the tube 608. With the beveled end 618 being angled relative to the sidewall of the tube 608, when the beveled end 618 and the tube opening 619 are generally horizontal and/or parallel with the bottom portion 624 of the fluid permeable body 610, the tube 608 may angle relative to the bottom portion 624 of the fluid permeable body 610. For example, the tube 608 may angle from the beveled end 618 towards the aperture 612 and out of the chamber 604.

Embodiments having the tube 608 with the beveled end 618 may be used when the fluid collection device 600 is positioned generally horizontal on a user. In operation, when a vacuum is applied to the tube 608, the tube 608 draws fluid from the sump 609 into the tube 608 through the tube opening 619. The fluid permeable body 610 provides connections for molecular bonding of fluids in the wound and/or in the chamber 604. The fluids being drawn into the tube 608 through the tube opening 619, then, also may draw fluid in the fluid permeable body 610 to the sump 609 via the molecular bonding of the water in the fluids. The configuration of the sump 609 within the urine collection device 600 may prevent a loss of vacuum on fluid being drawn from the fluid collection device 600 and/or the fluid permeable body 610 may promote molecular bonding of fluid in the sump 609 between the fluid permeable body 610 and the tube opening 619, thereby improving fluid capture from the fluid collection device 600.

In some embodiments, the tube 608 may be positioned generally horizontally within the chamber 604. For example, the tube 608 may include a tube opening spaced from an end of the tube 608, similar to or the same as the tube 338. The tube opening may be oriented towards the 606 and/or the bottom portion 624 of the fluid permeable body 610.

Figure 7:
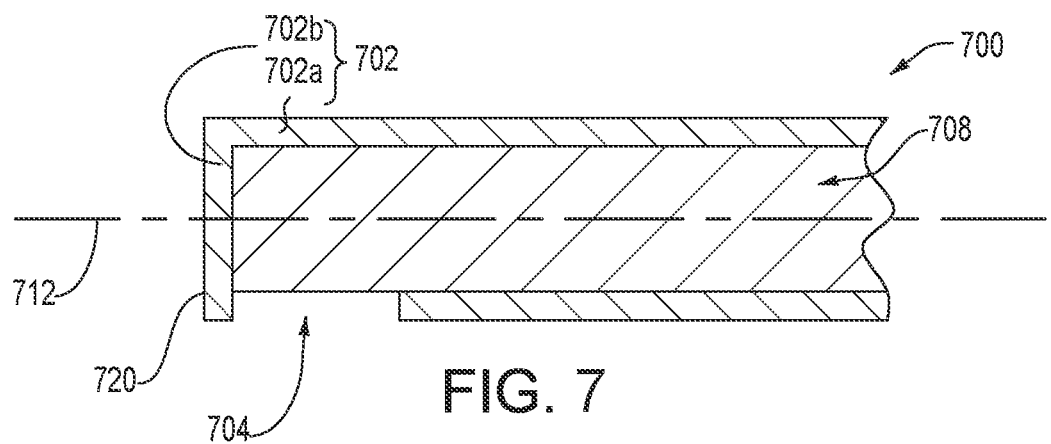
FIG. 7 is a schematic cross-sectional view of a portion of an embodiment of a tube, according to an embodiment.

As noted above, some embodiments of a fluid collection device may include a tube having a tube opening offset from the end of the tube and/or on a sidewall of the tube (rather than defined at the terminating end of the tube). FIG. 7 is a schematic cross-sectional view of a portion of an embodiment of a tube 700, according to an embodiment. The tube 700 may be used in any of the fluid collection device described herein. Except as otherwise disclosed herein, the tube 700 may be the same or substantially similar to any of the tubes disclosed herein. For instance, the tube 700 may include at least one wall 702 defining an inlet 704 (or tube opening), an outlet (not shown), and a passageway 708 extending from the inlet 704 to the outlet. The tube 700 also includes at least one tube porous material 710 disposed in the passageway 708. It is noted that, while the inlet 704 of the tube 700 is illustrated and discussed, the same principles discussed herein with regards to FIG. 7 also applies to the outlet.

The wall 702 includes a laterally extending portion 702a and a terminal portion 702b. The laterally extending portion 702a extending generally parallel to a longitudinal axis 712 of the tube 700. The terminal portion 702b extends from the laterally extending portion 702a and forms a terminal end 720 of the tube 700. For example, the terminal portion 702b may extend from the laterally extending portion 702a in a direction that is obliquely angled or perpendicular to the longitudinal axis 712 of the tube 700.

The wall 702 may define the inlet 704. However, the inlet 704 is not at the terminal end 720 of the tube 700. Instead, the inlet 704 may be adjacent to (as shown) or spaced from the terminal end 720. The inlet 704 is defined by the laterally extending portion 702a of the wall 702 and, when the inlet 704 is adjacent to the terminal end 720, by the terminal portion 702b of the wall 702. It is noted that, in some embodiments, the tube porous material 710 may be omitted from the tube 700.

In some embodiments, the dimensions and/or cross-sectional shapes of some of the tubes disclosed herein may be different than the inlets and outlets of devices to which the tubes are configured to be attached. The different dimensions and/or cross-sectional shapes of the tubes relative to the inlets and outlets of the devices may prevent direct attachment of such tubes to the inlets and outlets of the devices. Further, the wall of some of the tubes disclosed here may exhibit a relatively small Young's modulus and/or a relatively small thickness which may inhibit forming an interference fit with the devices. As such, directly attaching such tubes to the devices may be difficult. Thus, the tubes disclosed herein may include one or more adaptors that are configured to facilitate attachment between the tubes disclosed herein and the inlets and/or outlets of the devices.

Figure 8A:
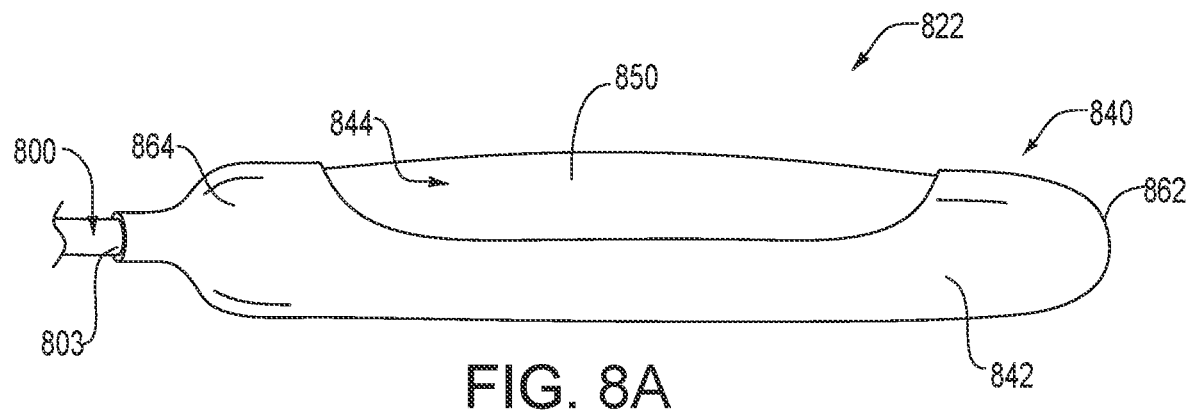
FIG. 8A is a side view of a female fluid collection assembly, according to an embodiment.

As noted above, aspects of the fluid collection devices described herein may be included in a female urine collection device, such as a female external catheter. FIG. 8A is a side view of a fluid collection system 822 in fluid communication with a fluid collection assembly 840. The fluid collection assembly 840 may include a female external catheter having a substantially tubular fluid impermeable barrier 842 having a proximal end region 864 and a distal end region 862. The fluid impermeable barrier 842 may define at least one opening 844, a chamber within the fluid collection assembly 840, and an aperture 803 at the proximal end region 864. The fluid collection assembly 840 also includes at least one fluid permeable body 850 disposed in the chamber.

Figure 8B:
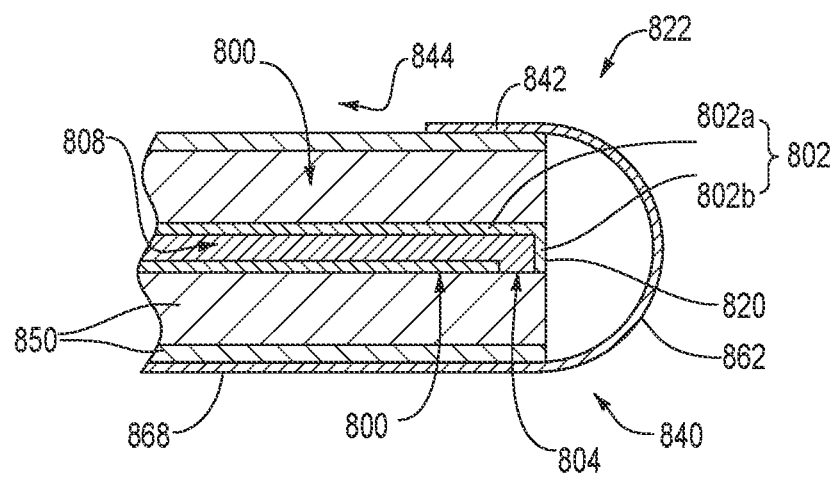
FIG. 8B is a cross-sectional schematic of a distal end region of the fluid collection assembly of FIG. 8A.

FIG. 8B is a cross-sectional schematic of a distal end region 862 of the fluid collection system 822, according to an embodiment. The tube 800 may include at least one wall 802 defining an inlet 804 and a passageway 808 and a tube porous material 810 disposed in the passageway 808. Except as otherwise disclosed herein, the fluid collection assembly 840 is the same or substantially similar to any of the fluid collection assemblies disclosed herein. The tube 800 may be substantially similar to the tube 700 illustrated in FIG. 7. For example, the inlet 804 of the tube 800 is not at the terminal end 820 of the tube 800. Instead, the wall 802 includes a laterally extending portion 802a and a terminal portion 802b extending from the laterally extending portion 802a. The terminal portion 802b of the wall 802 defines the terminal end 820 of the tube 800. The laterally extending portion 802a at least partially defines the inlet 804 of the tube 800. The inlet 804 is adjacent to the assembly porous material 850 which prevents the need to offset the inlet 804 relative to a terminal end 866 of the assembly porous material 850. Further, over-insertion of the tube 800 into the fluid collection assembly 840 will result in the terminal portion 802b of the wall 802 contacting the fluid impermeable barrier 842 instead of the fluid impermeable barrier 842 obstructing the inlet 804.

In some embodiments, the fluid collection assembly 840 may be generally horizontally oriented. The fluid collection assembly 840 may be generally horizontally oriented when the distal end region 862 is not the gravimetric low point of the chamber 846. Instead, at least a portion of a back side 868 of the fluid impermeable barrier 842 (e.g., a side of the fluid impermeable barrier 842 generally opposite the opening 844) or an intersection between the back side 868 and the distal end region 862 is the gravimetric low point of the chamber 846. The fluid collection assembly 840 may be generally horizontal when the patient is sitting or standing. The bodily fluids may generally collect in a portion of the chamber 846 along the back side 868 of the fluid impermeable barrier 842 when the fluid collection assembly 840 is generally horizontally oriented. The inlet 804 of the tube 800 may be oriented to generally face the back side 868 of the fluid impermeable barrier 842. In some embodiments, the inlet 804 of the tube 800 may be oriented to generally face the front side of the fluid impermeable barrier 842 that at least partially defines the opening 844. The inlet 804 may remove bodily fluids from the chamber 846 sooner and more efficiently from the chamber 846 than conventional tubes when the fluid collection assembly 840 is generally horizontally oriented since the inlet 804 generally faces towards the pooling bodily fluids.

Figure 9:
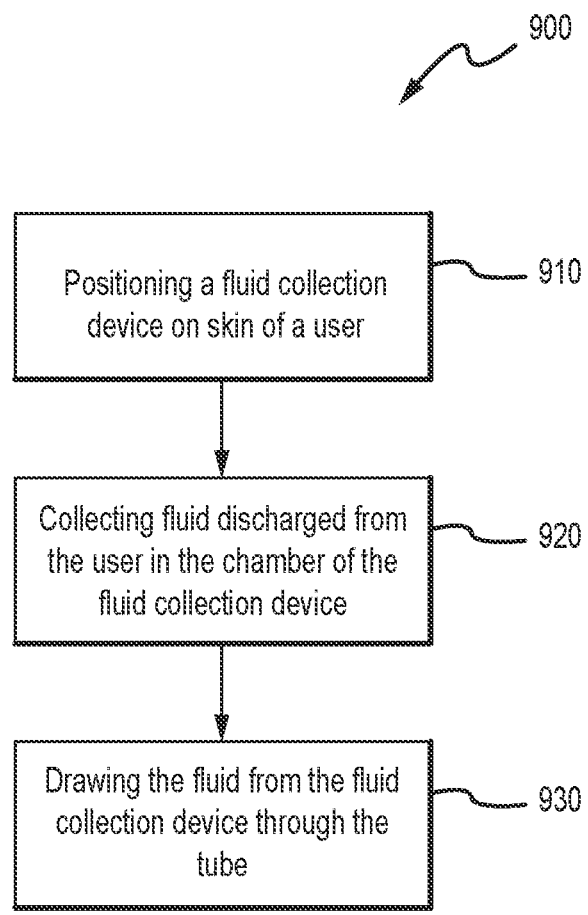
FIG. 9 is a flow diagram of a method for collecting fluid with a fluid collection device, according to an embodiment.

FIG. 9 is a flow diagram of a method 900 for collecting fluid from a user, according to an embodiment. The method 900 includes an act 910 of positioning a fluid collection device on skin of a user. The method 900 also includes an act 920 of collecting fluid discharged from the user in the chamber of the fluid collection device. The method also includes an act 930 of drawing the fluid from the fluid collection device through the tube.

Any of the fluid (including urine) collection devices described herein may be used in the method 900. In some embodiments, the fluid collection device of the method 900 includes a fluid impermeable barrier at least partially defining an opening and a chamber within the fluid collection device in fluid communication with the chamber, the fluid impermeable barrier having a proximal end region and a distal end region. The fluid collection device of the method 900 may include a fluid permeable body positioned within the chamber and extending at least partially between the distal end region and the proximal end region. The fluid collection device of the method 900 may include a tube extending into the chamber and having an end positioned proximate to the distal end. The tube may include a tube opening proximate to the end of the tube and oriented to face at least a portion of the fluid permeable body that may be positioned in the chamber between the distal end region of the fluid impermeable barrier and the end of the tube.

In some embodiments, the method 900 includes an act of covering the tube opening with the fluid permeable body and/or embedding the tube opening at least partially in the fluid permeable body. In some embodiments, the method 900 includes an act of inserting the tube at least partially through a channel in the fluid permeable body. In some embodiments, the method 900 includes inserting the tube opening in a recess in the fluid permeable body with the tube opening oriented to face a portion of the fluid permeable body that may be positioned between the tube opening and the distal end of the fluid impermeable barrier.

In some embodiments, the method 900 includes an act of inserting a penis of the user in the opening in the fluid impermeable barrier. The act 910 of positioning a fluid collection device on skin of a user may include positioning a bottom portion of the fluid impermeable barrier having a bottom portion to interface the user such that the bottom portion of the fluid impermeable barrier and a bottom portion of the fluid permeable body are substantially horizontal when the user is in a supine position. In some embodiments, the end of the tube may be capped or covered and the tube may include a sidewall defining the tube opening, with the tube opening being oriented towards the bottom portion of the fluid impermeable barrier and the tube being generally horizontal. In some embodiments, the fluid impermeable barrier defines an aperture positioned between the opening and the distal end, with the tube extending through the aperture into the chamber. In some embodiments, the end of the tube positioned in the chamber may include a beveled end with the tube opening positioned at the beveled end, and the tube may relative to the bottom portion of the fluid permeable body from the beveled end towards the aperture and out of the chamber.

In some embodiments, the act 910 of positioning a fluid collection device on skin of a user may include positioning the fluid collection device on a wound on the skin of the user with the opening in the fluid impermeable barrier over the wound and a bottom portion of the fluid permeable body disposed on the wound.

The acts of the method 900 described above are for illustrative purposes. For example, the acts of the method 900 can be performed in different orders, split into multiple acts, modified, supplemented, or combined. In an embodiment, one or more of the act of the method 900 can be omitted from the method 900. Any of the acts of the method 900 can include using any of the urine collection devices disclosed herein.

As used herein, the term "about" or "substantially" refers to an allowable variance of the term modified by "about" or "substantially" by ±10% or ±5%. Further, the terms "less than," "or less," "greater than," "more than," or "or more" include, as an endpoint, the value that is modified by the terms "less than," "or less," "greater than," "more than," or "or more."

While various aspects and embodiments have been disclosed herein, other aspects and embodiments are contemplated. The various aspects and embodiments disclosed herein are for purposes of illustration and are not intended to be limiting.

What is claimed is:

1. A urine collection device, comprising:
   a fluid impermeable barrier at least partially defining a chamber within the fluid collection device, the fluid impermeable barrier having a proximal end region and a distal end region, the fluid impermeable barrier at least partially defining an opening configured to allow at least one of fluid or at least a portion of a penis to enter the chamber;
   a fluid permeable body positioned at least partially within the chamber and extending at least partially between the distal end region and the proximal end region; and
   a tube extending into the chamber and having an end positioned proximate to the distal end region of the chamber, wherein the tube includes a tube opening at least proximate to the end of the tube and oriented to face at least a portion of the fluid permeable body.

2. The urine collection device of claim 1, wherein the opening defined by the fluid impermeable barrier exhibits a size to receive at least a portion of a penis.

3. The urine collection device of claim 1, wherein the opening defined by the fluid impermeable barrier is positioned between the distal end region and the proximal end region.

4. The urine collection device of claim 1, wherein the chamber narrows from the proximal end region to a tip at the distal end region, a bottom portion of the fluid impermeable barrier positioned to interface a user and defining the opening defined by the fluid impermeable barrier that is sized to receive at least a portion of the penis of the user therethrough, the opening defined by the fluid impermeable barrier being positioned between the distal end region and the proximal end region.

5. The urine collection device of claim 1, wherein the tube extends through the opening defined by the fluid impermeable barrier and into the chamber.

6. The urine collection device of claim 1, wherein the fluid impermeable barrier defines an aperture positioned between the opening defined by the fluid impermeable barrier and the distal end region of the fluid impermeable barrier, the tube extending through the aperture into the chamber.

7. The urine collection device of claim 1, further comprising at least one of a wire coil or plastic positioned proximate to the distal end region of the fluid impermeable barrier and configured to inhibit collapse of the chamber proximate to the distal end region.

8. The urine collection device of claim 1, wherein the chamber includes a filler material proximate to the distal end region including at least one of netting, beads, spun plastic, or straws that inhibit collapse of the chamber proximate to the distal end region.

9. The urine collection device of claim 1, wherein the fluid permeable body includes a top portion positioned proximate the top portion of the fluid impermeable barrier, a bottom portion positioned proximate to the bottom portion of the fluid impermeable barrier, and a channel positioned between the top portion of the fluid permeable body and the bottom portion of the fluid permeable body, and wherein the tube extends at least partially through the channel.

10. The urine collection device of claim 1, wherein the fluid permeable body includes a recess proximate to the distal end region of the fluid impermeable barrier and the tube opening is positioned within the recess with a portion of the fluid permeable body being positioned between the tube opening and the distal end region of the fluid impermeable barrier.

11. The urine collection device of claim 1, wherein the fluid permeable body covers the tube opening.

12. The urine collection device of claim 1, wherein the tube opening is oriented to face at least a portion of the fluid permeable body that is positioned between the distal end region of the fluid impermeable barrier and the opening defined by the fluid impermeable barrier.

13. The urine collection device of claim 1, wherein the tube opening is spaced from the distal end region of the fluid impermeable barrier.

14. The urine collection device of claim 1, wherein the tube opening is between the distal end region and the opening defined by the fluid impermeable barrier.

15. The urine collection device of claim 1, wherein the end of the tube is capped and the tube includes a side wall defining the tube opening.

16. The urine collection device of claim 1, wherein the tube opening being oriented towards a bottom portion of the fluid impermeable barrier, wherein the bottom portion at least partially defines the opening defined by the fluid impermeable barrier.

17. The urine collection device of claim 1, wherein the end of the tube includes a beveled end with the tube opening positioned at the beveled end.

18. The urine collection device of claim 17, wherein the tube angles relative to a bottom portion of the fluid permeable body from the beveled end towards the aperture and out of the chamber, wherein the bottom portion at least partially defines the opening defined by the fluid impermeable barrier.

19. A method of collecting fluid from a user, the method comprising:
    positioning a urine collection device on a user, the urine collection device including:

a fluid impermeable barrier, the fluid impermeable barrier at least partially defining a chamber within the fluid collection device, the fluid impermeable barrier at least partially defining an opening that allows fluid or a penis to enter the chamber, the fluid impermeable barrier having a proximal end region and a distal end region, wherein positioning the urine collection device on the user includes positioning the opening adjacent to a urethral opening defined by the user or inserting at least a portion of a penis of the user through the section;

a fluid permeable body positioned within the chamber and extending at least partially between the distal end region and the proximal end region; and a tube extending into the chamber and having an end positioned proximate to the distal end region of the chamber, wherein the tube includes a tube opening at least proximate to the end of the tube and oriented to face at least a portion of the fluid permeable body;

collecting fluid discharged from the user in the chamber of the fluid collection device; and drawing the fluid from the fluid collection device through the tube.

20. The method of claim 19, wherein positioning the urine collection device on the user includes inserting at least a portion of a penis of the user through the section.

\* \* \* \* \*